US008410056B2

(12) United States Patent
Ralph et al.

(10) Patent No.: US 8,410,056 B2
(45) Date of Patent: Apr. 2, 2013

(54) PRO-OXIDANT ANTI-CANCER COMPOUNDS

(76) Inventors: Stephen John Ralph, Mermaid Waters (AU); Jiri Neuzil, Runaway Bay (AU)

( * ) Notice: Subject to any disclaimer, the term of this patent is extended or adjusted under 35 U.S.C. 154(b) by 434 days.

(21) Appl. No.: 12/441,487

(22) PCT Filed: Sep. 17, 2007

(86) PCT No.: PCT/AU2007/001371
§ 371 (c)(1),
(2), (4) Date: May 20, 2009

(87) PCT Pub. No.: WO2008/031171
PCT Pub. Date: Mar. 20, 2008

(65) Prior Publication Data
US 2011/0059898 A1    Mar. 10, 2011

(30) Foreign Application Priority Data

Sep. 15, 2006  (AU) ................................ 2006905109

(51) Int. Cl.
*A61P 43/00* (2006.01)
(52) U.S. Cl. ...................................................... 514/18.9
(58) Field of Classification Search ........................ None
See application file for complete search history.

(56) References Cited

U.S. PATENT DOCUMENTS

| 6,716,873 | B1 | 4/2004 | Keramidas et al. |
| 2004/0175415 | A1 | 9/2004 | Chan et al. |
| 2004/0266835 | A1 | 12/2004 | Omura et al. |

FOREIGN PATENT DOCUMENTS

| WO | WO 99/24417 A1 | 5/1999 |
| WO | WO00/15120 | 3/2000 |
| WO | WO00/59488 | 10/2000 |
| WO | WO0005488 | 10/2000 |
| WO | WO2006/015120 | 2/2006 |

OTHER PUBLICATIONS

Fariss et al., Enhanced Antioxidant and Cytoprotective Abilities of Vitamin E Succinate is Associated with a rapid uptake advantage in rat hepatocytes and mitochondria, Free Radical Biology & Medicine, vol. 31, No. 4, pp. 530341, (2001).*
Birringer et. al. Vitamin E Analogues as Inducers of apoptosis: structure function relation, British Journal of Cancer (88) 1948-1955, 2003.*
Neuzil et. al. Vitamin E succinate and cancer treatment: a vitamin E prototype for selective antitumor activity, British Journal of Cancer (89) 1822-1826, 2003.*
Birringer et. al. (Vitamin E analogues as Inducers of apoptosis: structure function relation, British Journal of Cancer (88) 1822-1826, 2003.*
He, D.Y., et al, "Protein ubiquinone interaction. Synthesis and biological properties of 5-alkyl ubiquinone derivatives," J. Biol. Chem., Nov. 11;269(45): 27885-27888 (1994).
Hosomi, A. et al., "Affinity for alpha-tocopherol transfer protein as a determinant of the biological activities of vitamin E analogs," FEBS Lett 409: 105-108 (1997).
Huang, L.S., et al., "3-nitropropionic acid is a suicide inhibitor of mitochondrial respiration that, upon oxidation by complex II, forms a covalent adduct with a catalytic base arginine in the active site of the enzyme," J. Biol Chem., 281: 5965-5972 (2006).
James, A.M., et al., "Interactions of mitochondria-targeted and untargeted ubiquinones with the mitochondrial respiratory chian and reactive oxygen speies. Implications for the use of exogenous ubiquinones as therapies and experimental tools," J. Biol. Chem., 280: 21295-212312 (2005).
Kelso, G.F., et al., "Selective targeting of a redox-active ubiquinone to mitochondria within cells: antioxidant and antiapoptotic properties," J. Biol. Chem., 276: 4588-4596 (2001).
Kim, R., et al., "Potential roles of antisense therapy in the molecular targeting of genes involved in cancer," Int. J. Oncol., 24: 5-17 (2004).
King, A., et al., "Succinate dehydrogenase and fumarate hydratase: linking mitochondrial dysfunction and cancer," Oncogene, Aug. 7;25(34):4675-4682 (2006).
King, T.E., "Preparation of succinate dehydrogenase and reconstruction of succinate oxidase," Methods in Enzymology, 10:322-331 (1967).
King, T.S., "Preparation of succinate-cytochrome c reductase and the cytochrome b-c1 particle, and the reconstruction of succinate-cytochrome c reductase,"Methods in Enzymology, 10:216-225 (1967).
Ko, Y.H., et al., "Advanced cancers:eradication in all cases using 3-bromopyruvate therapy to deplete ATP," Biochem Biophys Res Commun, 324: 269-275 (2004).
Kogure, K., et al., "Structural characteristic of terminal dicarboxylic moiety required for apoptogenic activity of alpha-tocopheryl ester," Biochem Biophys Acta, 1672: 93-99 (2004).
Kunisaki, M., et al., "Vitamin E prevents diabetes-induced abnormal retinal blood flow via the diacylglycerol-protein kinase C pathway," Am. J. Physiol, 269: E239-246 (1995).
Maehara, Y., et al., "Sodium succinate enhances the colorimetric reaction of the vitro chemosensitivity test: MTT assay," Oncology, 5:434-436 (1988).
Makishima, M., et al., "Induction of differentiation in acute promyelocytic leukemia cells by 9-cis retinoic acid alpha tocopherol ester (9-cis tretinoin tocoferil)," Blood, 91: 4715-4726 (1998).
Malafa, M.P., et al., "Vitamin E inhibits melanoma growth in mice," Surgery, 131: 85-91 (2002).

(Continued)

Primary Examiner — Christina Bradley
Assistant Examiner — Jeanette Lieb
(74) Attorney, Agent, or Firm — Thomas E. Jurgensen; Gint Silins

(57) ABSTRACT

This invention relates to anti-cancer compounds and to methods for treating or preventing cancer. In particular, the invention concerns pro-oxidant anti-cancer compounds, such as pro-oxidant forms of vitamin E that selectively interact with complex II of the mitochondrial respiratory chain of cancerous cells, generate reactive oxygen species and induce apoptosis of those cells.

3 Claims, 18 Drawing Sheets

OTHER PUBLICATIONS

Malafa, M.P. and Neitzel, L.T., "Vitamin E succinate promotes breast cancer tumor dormancy," J. Surg. Res., 93: 163-170 (2000).

Martin-Nizard, F., et al., "alpha-tocopherol but not beta-tocopheril inhibits trombin-induced PKC activation and endothelin secretuin in endotherlial cells," J. Cardiovas. Risk, 5:339-345 (1998).

Modica-Napolitano, J.S., and Singh, K.K., "Mitochondria as targets for detection and treatment of cancer," Expert Rev Mol Med., Apr. 11;4(9):1-19 (2002).

Morris, G.M., et al., "Automated docking using a Lamarckiam genetic algorithim and empirical binding free energy function," J Comp Chem, 19: 1639-1662 (1998).

Morton, L.W., et al., "Evidence for the nitration of gamma-tocopherol in vivo: 5-nitro-tocopherol is elevated in the plasma of subjects with coronary heart disease," Biochem. J., Jun. 15; 364(Pt 3):625-628 (2002).

Muteanu, A., et al., "A Modulation of cell proliferation and gene expression by alpha tocopherol phosphates: relevance to antherosclerosis and inflammation,"Biochem Biophys Res COmmun, 318:311-316 (2004).

Negis, Y., et al., "On the existence of cellular tocopherol phosphate, its synthesis, degradation, and cellular roles: a hypothesis," IUBMB Life, 57:23-25 (2005).

Nesaretnam, K., et al., "Tocotrienols inhibit the growth of human breast cancer cells irrespective of estrogen receptor status," Lipids, 33:461-469 (1998).

Neuzil, J., et al., "Vitamin E analogues as a novel group of mitocans: Anti-cancer agents that act by targeting mitochondria," Moi Aspects Med., Feb. 23 (2007).

Neuzil, J., and Massa, H., "Hepatic processing determines dual activity of vitamin E succinate," Biochem Biophys Res Commun, 327: 1024-1027 (2005).

Neuzil, J., et al., "Vitamin E analogs, a novel group of 'mitocans,' as anticancer agents: the importance of being redox-silent," Mol., Pharmacol., May; 71(5): 1185-1199 (2007).

Neuzil, J., et al., "Selective cancer cell killing by alpha-tocopherol succinate," British Journal of Cancer, 84 (1); 87-89 (2000).

Nishikawa, K., "alpha tocopherolyloxybutyric acid enhances necrotic cell death in breast cancer cells treated with chemotherapy agent," Cancer Lett, 201: 51-56 (2003).

Oostveen, F.G., et al., "A Chinese hamster mutant cell line with a defect in the integral membrane protein CII-3 of complex II of the mitochondria electron transport chain," J Biol Chem., Nov., 3;270(44): 26104-26108 (1995).

Osaki, M., et al., "PI3K—Akt pathway:its functions and alterations in human cancer," Apoptosis, 9:667-676 (2004).

Pham, D.Q. and Plakogiannis, R., Vitamin E supplementaion in cardiovascular disease and cancer prevention: Part 1. Ann. Pharmacother. 39:1870-1878 (2005).

Pollard, P.J., et al., "Accumulation of Krebs cycle intermediates and over-expression of HIF1alpha in tumors which result from germline FH and SDH mutations,"Hum. Mol. Genet., Aug. 1;14(15):2231-2239 (2005).

Quin, J., et al., "Vitamin E Succinate decreases lung cancer tumor growth in mice," J. Surg Res. 127:139-143 (2005).

Qureshi, A.A., et al., "Isolation and identification of novel tocotrienols from rice bran with hypocholesterolemic, antioxidant, and antimumor properties," J. Agric Food Chem, 48:3130-3140 (2000).

Ralph, S.J., et al., "Mitocans: mitochondria targeted anti-cancer drugs as improved therapies and related patents," Recent Pat Anticancer Drug Discov., 1:305-326 (2006).

Ricciarelli, R., et al., "Vitamin E reduces the uptake of oxidized LDL inhibiting CD36 scavenger receptor expression in cultures aortic smooth muscle cells," Circulation, 102: 82-87 (2000).

Safford, S.E., et al., "Suppression of fibrosarcoma metastasis by elevated expression of maganese superoxide dimutase," CAncer Res.., 64: 4261-4265 (1994).

Sanborn, B.M., et al., "The inactivation of succinate dehydorgenase by bromopyruvate," Biochem Biophy Acta, 227: 219-231 (1971).

Sanner, M.F., "Python: a programming language for software integration and development," J. Mol. Graphic Mod., 17: 57-61 (1999).

Scallett, A.C., et al., "3-nitropropionic acid inhibition of succinate dehydrogenase (complex II) activity in cultured Chinese hamster ovary cells: antagonism by L-carnitine," Ann. NY Acad Sci., 993: 305-312 (2003).

Scheffler, I.E., et al., "Molecular genetics of complex I-deficient Chinese Hamster cell lines," Biochem Biophys Acta, Dec. 6;1659(2-3):160-171 (2004).

Seo, B.B., et al., Proc Natl Acad. Sci., 95, 9167-9171 (1998).

Shah, S.J. and Sylvester, P.W., "γ-tocotrienol inhibits neoplastic mammary epithelial cell proliferation by decreasing AKt and nuclear factor kB activity," Exp. Biol. Med. 230: 235-241 (2005).

Shiau, S.J., et al., "alpha-tocopheryl succinate induces apoptosis in prostate cancer cells in part through inhibition of Bcl-xL/Bcl-2 function," J. Biol. Chem., 281: 11819-11825 (2006).

Shun, M.C., et al., "Pro-apoptotic mechanisms of action of a novel vitamin E analog (alpha-TEA) and a naturally occuring from vitamin E (gamma-tocotrienol) in MDA-MB-435 human breast cancer cells," Nutr. Cancer, 48: 95-105 (2004).

Slamon, D.J., et al., "Studies of the HER-2/neu proto-oncogene in human breast and ovarian cancer," Science, 244: 707-712 (1989).

Sugawar, M., et al., "Transport of valganciclovir, a ganciclovir prodrug, via peptide transporters PEPT1 and PEPT2," J. Pharm Sci., 89: 781-789 (2000).

Sun, F., et al., "Crystal structure of mitochondrial respiratory membrane protein complex II," Cell, 121: 1043-1057 ().

Szewczyk, A. and Wojtczak, L., "Mitochondria as a pharmacological target," Pharmacol. Rev., Mar;54(1):101-127 (2002).

Takeuchi, H., et al., "X-Linked inhibitor of apoptosis protein expression level in colorectal cancer is regulated by hepatocyte growth factor/ C-met pathway via Akt signaling," Clin. cancer Res., 11:7621-7628 (2005).

Wang, X.-F. et al. "Vitamin E analogs trigger apoptosis in HER2/erbB2-overexpressing breast cancer cells by signalling via the mitochondrial pathway" Biochem. Biophys. Res. Comm. 2005, vol. 326 pp. 282-289.

Swettenham, E. et al. "α-Tocopheryl succinate selectively induces apoptosis in neuroblastoma cells: potential therapy of malignancies of the nervous system?" Journal of Neurochemistry, 2005, vol. 94 pp. 1448-1456.

Tomic-Vatic, A. et al. "Vitamin E amides, a new class of vitamin E analogues with enhanced proapoptotic activity" Int. J. Cancer. 2005, vol. 117, No. 2 pp. 188-193.

Neuzil, J. et al. "Vitamin E Analogues: A New Class of Inducers of Apoptosis with Selective Anti-Cancer Effects" Current Cancer Drug Targets. 2004, vol. 4 pp. 355-372.

Anderson, K. et al. "Differential Response of Human Ovarian Cancer Cells to Induction of Apoptosis by Vitamin E Succinate and Vitamin E Analogue, α-TEA" Cancer REsearch. 2004. vol. 64 pp. 4263-4269.

Birringer, M. et al. "Vitamin E analogues as inducers of apoptosis: structure-function relation" Br. J. Cancer 2003, vol. 88, No. 12 pp. 1948-1955.

Kogure, K. et al. "Cytotoxicity of α-Tocopheryl Succinate, Malonate and Oxalate in Normal and Cancer Cells In Vitro and Their Anti-Cancer Effects on Mouse Melanoma In Vivo" J. Nutr. Sci. Vinaminol. 2004, vol. 51, pp. 392-397.

Stapelberg, M. et al. "α-Tocopheryl Succinate Inhibits Malignant Mesothelioma by Disrupting the Fibroblast Growth Factor Autocrine Loop" J. Bio. Chem. 2005, vol. 280, No. 27 pp. 25369-25375.

Tomasetti, M. et al. "α-Tocopheryl succinate and TRAIL selectively synergise in induction of apoptosis in human malignant mesothelioma cells" Br. J. Cancer. 2004, vol. 90, No. 8 pp. 1644-1653.

Neuzil, J. et al. "Induction of cancer cell apotosis by α-tocopheryl succinate: molecular pathways and structural requirements" FASEB J. 2001 vol. 15 pp. 403-415.

Neuzil, J. et al. "Vitamin E analogues as inducers of apoptosis: implications for their potential antineoplastic role" Redox Report. 2001, vol. 6, No. 3 pp. 143-151.

Neuzil, J. et al. "Selective cancer cell killing by α-tocopherol succinate" British Journal of Cancer. 2000, vol. 84, No. 1 pp. 87-89.

NCBI PubChem Database [URL:http://pubchem.ncbi.nlm.nih.gov/]. PubChem compound Nos. 778472, 1484380, 1051, 173846, 644168, 1963561, 1963562, 4542447, 4362036, 4362035, 4187415, 179273, 5280346, 21307, 5601.

Shadidi, M. and Sioud, M. "Identification of novel carrier peptides for hte specific delivery of therapeutics into cancer cells" FASEB J. 2003, vol. 17 pp. 256-258.

Tan, A.K., et al., "Comparison of the structures of the quinone-binding sites in beef heart mitochondria," J. Biol. Chem., Sep. 15; 268(26): 19328-19333 (1993).

Tasinato, A., et al., "Delta alpha-Tocopherol inhibition of vascular smooth muscle cell proliferation occurs at physical concentrations, correlates with protein kinase C inhibition, and is independent of its antioxidant properties," Proc Natl Acad Sci., 92: 12190-12194 (1995).

Teague, S.J., et al., "The Deign of Leadlike Combinational Libraries," Angrew Chem. Int. Ed. Engl., 38; 3743-3748 (1999).

Tomasetti. M., et al., "alpja-tocopheryl succinate and Trail selectively synergise in induction of apoptosis in human malignant mesothelioma cells," Br. J. Cancer, 90(8) 1644-1653 (2004).

Tomasetti, M., et al., "A vitamin E analogue suppresses malignant mesothelioma in pre-clinical model: A prototype of a future drug against a fatal neoplastic disease?" Int. J. Cancer, 109: 641-642 (2004).

Van Nederveen, F.H., et al., "Somatic SDHB mutation in an extraadrenal pheochromocytoma," N Engl. J. Med., Jul. 19; 357(3): 306-308 (2007).

Vraka, P.S., et al., "Synthesis and study of the cancer cell growth inhibitory properties of alpha, gamma-tocopheryl and gamma-tocotrienyl 2-phenyselenyl succinates," Bioorg Med. Chem., 14: 2684-2696 (2006).

Wallace, A.C., et al., "LIGPLOT: a program to generate schematic diagrams of protein-ligand interactions," Protein Eng., 8, 127-134 (1995).

Wang, X.F., et al., "alpha-tocopheryl succinate induces apoptosis in HER2/erB2-overexpressing breast cancer cells by signalling via the mitochondrial pathway," Biochem Biophys Res Commun., 326: 282-289 (2005).

Wang, X.F., et al., "A peptide conjugate of vitamin E succinate targets breast cancer cells with high ErB2 expression," Cancer Res., Apr. 1; 67(7): 3337-3344 (2007).

Weber, T., et al., "Mitochondria play a central role in apoptosis induced by alpha-tocopheryl succinate, an agent with anticancer activity. Comparison with receptor-mediated pro-apoptotic signaling," Biochemistry, 42: 4277-4291 (2003).

Weber, T., "Vitamin E succinate is a potent novel anti-neoplastic agent with high tumor selectivity and cooperativity with tumor necrosis factor-related apoptosis-inducing ligand (TRAIL, Apo2L) in vivo," Clin. Cancer Res. 8:863-869 (2002).

West, K.A., et al., "Activation of the P13K/Akt pathway and chemotherapeutic resistance," Drug Resist Updat, 5: 234-248 (2002).

Wu, Y., et al., "Cellular and molecular effects of alpha-tocopheryloxybutyrate: lessons for the design of vitamin E analog for cancer prevention," Anticancer Res., 24: 3795-3802 (2004).

Xu, R.H., et al., "Inhibition of glycolysis in cancer cells: a novel strategy to overcome drug resistance associated with mitochondrial respiratory defect and hypoxia," Cancer Res. 65: 613-621 (2005).

Yabunaka, H., et al., "Hybrid ubiquinone: novel inhibitor of mitochondrial complex I," Biochem Biophys Acta, Dec. 2; 1556(2-3): 106-112 (2002).

Yamauchi, J., et al., "Tocopherol-associated protein is a ligand dependent transcriptional activator," Biochem Biophys Res Commun, 285: 295-299 (2001).

Yang, F., et al., "Protein-ubiquinone interaction in bovine heart mitochondrial succinate-cytochrome c reductase. Synthesis and biological properties of fluorine substituted ubiquinone derivatives," J. Biol. Chem., Nov. 5;266 (31):20863-20869 (1991).

Yano, Y., et al., "Induction of cytotoxicity in human lung adenocarcinoma cells by 6-o-carboxy-propyl-alpha-tocotrienol," Int. J. Cancer, 115: 839-846 (2005).

Yoeli-Lerner, M., et al., "Akt blocks breast cancer cell motility and invasion through the transcription factor NFAT," Mol. Cell 20:539-550 (2005).

Youk, H.J., et al., "Enhanced anticancer efficacy of alpha-tocopheryl succinate by conjugation with polyethylene glycol," J. Control Release, 107: 43-52 (2005).

Zhang, J.G., et al., "Vitamin E succinate protects hepatocytes against the toxic effect of reactive oxygen species generated at mitochondrial complexes I and III by alkylating agents," Chem Biol. Interact., 138: 267-284 (2001).

Zhang, J.G., et al., "Mitochondrial electron transport inhibitors cause lipid peroxidation-dependent and independent cell death: protective role of antioxidants," arch Biochem Biophys, 393: 87-96 (2001).

Zhao, S., et al., "Inhibition of phosphatidylinositol 3-kinase dephophorylates BAD and promotes apoptosis in myloid leukemias," Leukemia 18: 267-270 (2004).

Zhao, S., et al., "Alpha tocopheryl succinate-induced apoptosis in human gastric cancer cells is modulated by ERK1/2 and c-Jun N-terminal kinase in a biphasic manner," Cancer Letters, 247(2); 345-352 (2007).

Nelson, K., "3-Bromopyruvate kills cancer cells in animals," Lancet Oncology, 3 ; 524 (2002).

Neuzil, J., Vitamin E succinate and cancer treatment: a vitamin E prototype for selective antitumour activity, British Journal of Cancer, 89 (10); 1822-1826 (2003).

Fariss, M.W., et al., "Enhanced antioxidant and cytoprotectuve abilities of vitamin E succinate is associated with a rapid uptake advantage in rat hepatocytes and mitochondria," Free Radic Biol Med, 31: 530-541 (2001).

Fresno Vara J.A., et alo., "P13K/Akt signalling pathway and cancer," Cancer Treat Rev, 30: 193-204 (2004).

Galli F., et al.,"The effect of alpha and γ-tocopherol and their carboxyethyl hydroxychroman metabolites on prostate cancer cell proliferation," Arch Biochem Biophys, 423: 97-102 (2004).

Geschwind J.F., et al, "Novel therapy for liver cancer: direct intaarterial injection of a potent inhibitor of ATP production," Cancer Res, 62:3909-3913 (2002).

Gottlieb E., et al., "Mitochondrial tumor suppressors: a genetic and biochemical update," Nat Rev Cancer, Nov; 5 (11): 857-866 (2005).

Grandage V.L., "P13-kinase/Akt is constitutively active in primary acute myeloid leukaemia cells and regulates survival and chemoresistance via NF-kB, MAP kinase and p53 pathways," Leukemia 19:588-594 (2005).

Gu, L.Q., et al., "Effect of substituents of the benzoquinone ring on electron-transfer activities o fubiquinon derivatives," Biochem Biophys Acta, Feb. 22;1015(3):482-492 (1990).

Guthrie, N., et al., "Inhibition of proliferation of estrogen receptor-negative MDA-MB-435 and -positive MCF-7 human breast cancer cells by palm oil tocotrienols and tamoxifen, alone and in combination," J Nutr, 127: 544S-548S (1997).

Guy, C.T., et al., "Expression of the neu protooncogene in the mammary epithelium of transgenic mice induces metastatic disease," Proc Natl Acad Sci, 89:10578-10582 (1992).

Hail, N. Jr., "Mitochondria: A novel target for the chemoprevention of cancer," Apoptosis, Aug; 10(4):687-705 (2005).

Hiroko, M., et al., "Atpenins, potent and specific inhibitors of mitochondrial complex II (succinate-ubiquinone oxidoreductase)," Proc Natl Acad Sci, 100(2): 437-477 (2003).

Horsefield, R., et al., "Structural and computational analysis of the quinone-binding of complex II (succinate-uiquinone oxidoreductase): a mechanism of electron transfer and proton conduction during ubiquinone reduction," The Journal of biological chemistry, Mar. 281(11): 7309-7316 (2006).

Hartshorn, M.J., "AstexViewer: An aid for structure-based drug design," J Computer Aided Mol Des, 16:871-881 (2002).

He L., et al., "Isoprenoids suppress the growth of murine B16 melanomas in vitro and in vivo," J Nutr, 127: 668-674 (1997).

Database Genbank [online] XP003021708 Retrieved from NCBI Database accession No. (R23584)(1995).

Albayrak, T., et al., "The tumor suppressor cybL, a component of the respiratory chain, mediates apoptosis induction," Mol. Biol. Cell, Aug., 14(8): 3082-3096 (2003).

Allen, F.H., "The Cambridge Structural Database: a quarter of a million crystal structures and rising," Acta Crystallogr B., 58(Pt 3 Pt1):380-388 (2002).

Allen, R. G. & Balin, A.K., "Effects of oxygen on the antioxidant responses of normal and transformed cells," Exp. Cell Res., 289:307-316 (2003).

Alleva, R., et al., "Coensyme Q blocks chemical but not receptor-mediated apoptosis by increasing mitochondrial antooxidant protection," FEBS Lett., 503: 46-50 (2001).

Aratri, E., et al., "Modulation of alpha-tropomyosin expression by alpha-tocopherol in rat vascular smooth muscle cells," FEBS Lett. 447: 91-94 (1999).

Armstrong, J.S., "Mitochondria: a target for cancer therapy," Br. J. Pharmacol. 147: 239-248 (2006).

Arya P., et al., "Design and synthesis of analogues of vitamin E: antoproliferative activity against human breast adenocarcinoma cells," Bioorg Med. chem. Lett. 8: 2433-2438 (1998).

Astuti D., et al., "Genetic analysis of mitochondrial complex II subunits SDHD, SDHB and SDHC in paraganglioma and phaeochromocytoma susceptability," Clin. Endocrinol. (Oxf.) Dec.; 59(6):728-733 (2003).

Asumendi A., et al., "Implication of mitochondria-derived ROS and cardiolipin peroxidation in N-(4-hydroxyphenyl) retinamide-induced apoptosis," Br. J. Cancer, Jun. 17;86(12): 1951-1956 (2002).

Azzi, A., et al., "Non-antioxidant molecular functions of alpha-tocopherol (vitamin E)," FEBS Lett. 519: 8-10 (2002).

Barnett, K. T., et al., "Vitamin E succinate inhibits colon cancer liver metastases," J. Surg. Res., 106: 292-298 (2002).

Bayley, J.P., et al., "Mutation analysis of SDHB and SDHC: novel germline mutations in sporadic head and neck paraganglioma and familial paraganglioma and/or pheochromocytoma," BMC Med. Genet., Jan. 11; 7:1 (2006).

Berridge, M.V., et al., "Tetrazolium dyes as tools in cell biology: new insights into their cellular reduction," Biotechnol. annu. Rev., 11: 127-152 (2005).

Berridge, M. V. & Tan, A.S., "Characterization of the cellular reduction of 3-(4,5-dimethylthiazol-2-yl)-2,5-diphenyltetrazolium bromide (MTT): subcellular localization, substrate dependence, and involvment of mitochondrial electron transport in MTT reduction," Arch. Biochem. Biophys., 303: 474-478 (1993).

Birringer, M., et al., "Tocopherols are metabolized in HepG2 cells by side chain W-oxidation and consecutive beta-oxidation," Free Radic. Biol. Med., 31:226-232 (2001).

Birringer, M., et al., "Identities and differences in the metabolism of tocotrienols and tocopherols in Hep G2 ceills," J. Nutr., 132: 3113-3118 (2002).

Boersma, A. W., et al., "Quantification of apoptotic cells with fluorescein isothiocyanate-labeled annexin V in Chinese hamster ovary cell cultures with cisplatin," Cytometry, 24: 123-130 (1996).

Breen, G. A. & Scheffler, I. E., Respiration-deficient Chinese hamster cell mutants: biochemical characterization, Somatic Cell Genet., Jul; 5(4):441-451 (1979).

Briere, J.J., et al., "Quinone analogues regulate mitochondrial substrate competitive oxidation," Biochem. Biophys. Res. Commun., Apr. 16; 316(4): 1138-1142 (2004).

Burstein, H.J., "THe distinctive nature of HER2-positive breast cancers," N. Engl. J. Med., 353: 1652-1654 (2005).

Burnell, J.N., et al., "The reversibility of active sulphate transport in membrane vesicles of Paracoccus denitrificans," Biochem. J., 150: 527-536 (1975).

Cardone, M.H., et al., "Regulation of celi death protease caspase-9 by phosphorylation," Science, 282: 1318-1321 (1998).

Cheeseman, K. H., et al., "Biokinetics in humnas of RRR-alpha-tocopherol: the free phenol, acetate ester, and succinate ester forms of vitamin E," Free Radic. Biol. Med., 19:591-598 (1995).

Choudhry, Z.M., et al., "Pyridoxal phosphate-induced dissociation of the succinate: ubiquinone reductases," FEBS Lett., Mar. 11; 182(1): 171-5 (1985).

Choudhry, Z. M., et al., "Studies on the succinate dehydrogenating system. Interaction of the mitochondrial succinate-ubiquinone reductase with pyridoxal phosphate," Biochim. Biophys. Acta., Jun. 10; 850(1): 131-138 (1986).

Christen, S., et al., "Gamma-tocopherol traps mutagenic electrophiles such as NO(X) and complements alpha-tocopheral: physiological Implications," Pro. Natl. Acad. Sci., Apr. 1;94(7):3217-3222 (1997).

Church, S. L., et al., "Increased manganese superoxide dismutase expression supresses the malignant phenotype of human melanoma cells," Proc. Natl. Acad. Sci., 90:3113-3117 (1993).

Costantini, P., et al., "Mitochondrion as a novel target of anticancer chemotherapy," J. Natl. Cancer Inst., Jul. 5;92 (13): 1042-1053 (2000).

Debatin K. M., et al., "Chemotherapy: targeting the mitochondrial cell death pathway," Oncogene, 21(57): 8786-8803 (2002).

DeFrancesco, L., et al., "A respiration-deficient Chinese hamster cell line with defect in NADH-coenzyme Q reductase," J. Biol. CHem., Aug. 10; 251(15): 4588-4595 (1976).

Devaraj, S., et al., "Alpha Tocopherol decreases CD36 expression in human monocyte-derived macrophages," J. Lipid Res., 42:521-527 (2001).

Dias, N. & Bailly C., "Drugs targeting mitochondrial functions to control tumor cell growth," Biochem. Pharmacol., Jul. 1;70(1):1-12 (2005).

Don, A.S. & Hogg, P.J., "Mitochondria as cancer drug targets," Trends Mol. Med. 10:372-378 (2004).

Dong L.F., et al., "Vitamin E analogues as anti-cancer agents: the role of modulation of apoptosis signalling pathways," Cancer Therapy, 4:35-46 (2006).

Esposti, M. D., et al., "The interaction of Q analogs, particularly hydroxydecyl benzoquinone (idebenone), with the respiratory complexes of heart mitochondria," Arch. Biochem. Biophys., Jun. 15;330(2):395-400 (1996).

* cited by examiner

Cut-away view comparing UbQ head group and alpha-TOS bound into the $Q_P$ binding pocket of Complex II

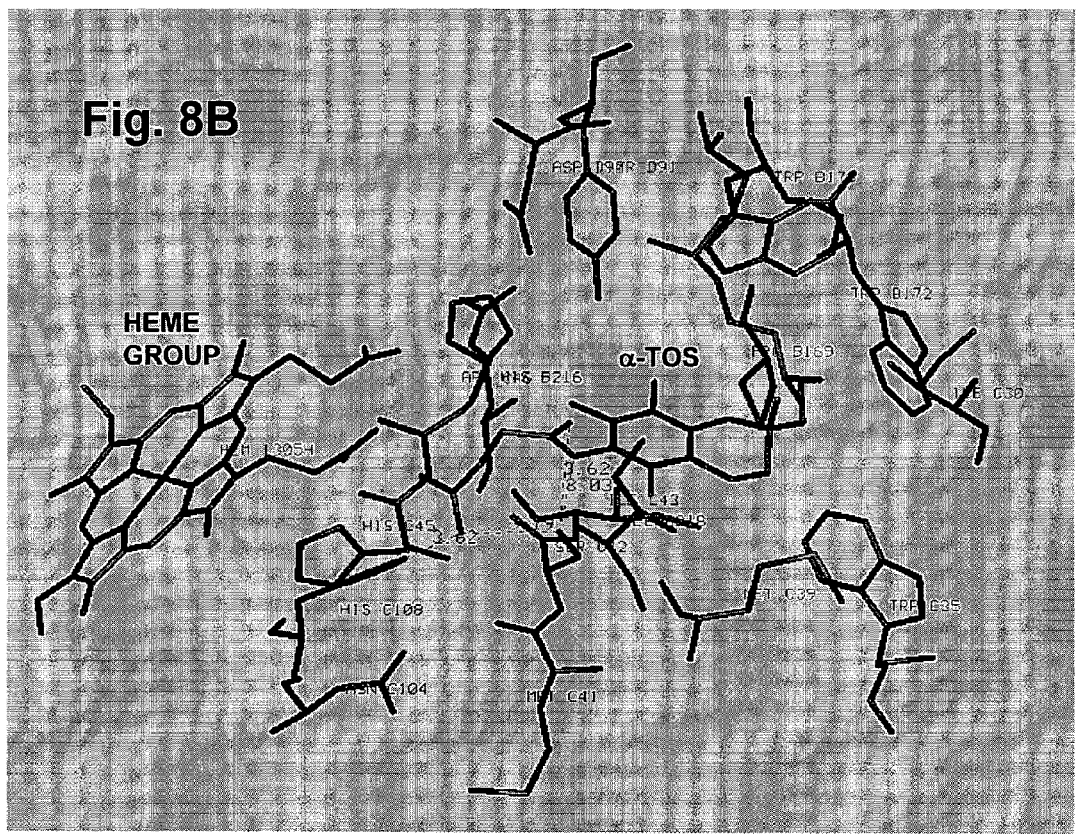

Stereo images of alpha-TOS binding into the Qp pocket in Complex II enabling visualization of 3-D structural arrangement of essential side groups involved in the binding interactions.

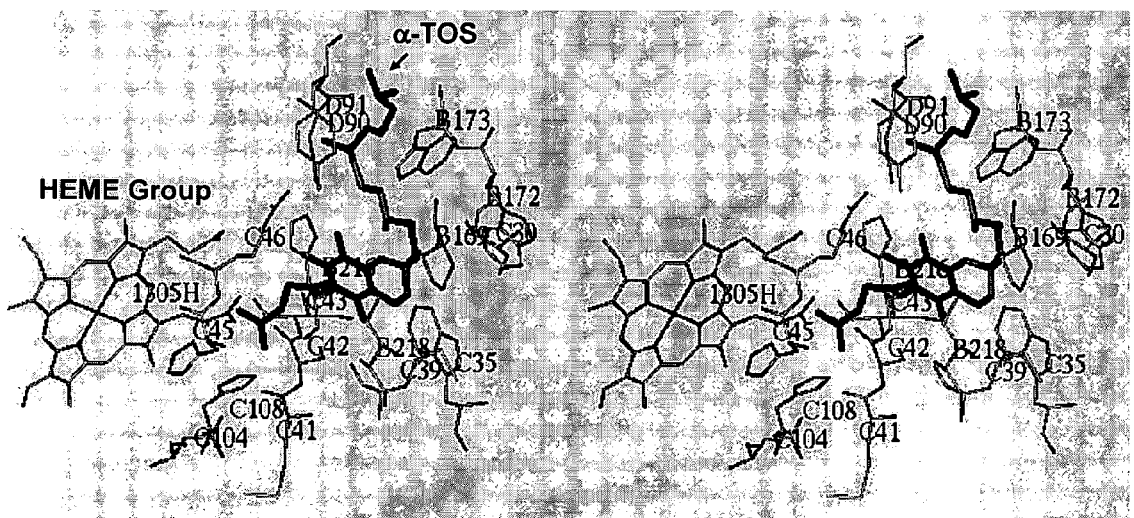

C42 represents the conserved Serine amino acid residue 42 of the human CybL chain subunit of Complex II involved in the binding of the succinyl group of alpha-TOS, strengthening the specificity of binding via hydrogen bonding.

Fig. 8C

Ligand binding interactions of alpha-TOS with the Qp site of complex II

Spatial distribution of critical amino acid residues involved in the binding interaction of alpha-TOS in the Qp pocket of complex II.

Note: the hydrogen bonding (dotted lines) between the succinyl group of TOS and the Serine residue C42 of the complex II SDHC subunit Image comparing UbQ head group and alpha-TOS bound into the $Q_D$ binding pocket of Complex II Binding of alpha-TOS compared to UbQ wrapped around inside the pocket, showing a bridge (in translucent format) formed by part of Complex II extending across the front of the pocket.

Ligand binding interactions of alpha-TOS with the Qd site of complex II

Spatial distribution of critical amino acid residues involved in the binding interaction of alpha-TOS in the Qd pocket of complex II.

Note: the hydrogen bonding (dotted lines) between the succinyl group of TOS and the Lysine residues D128, D135 of the complex II SDHD subunit

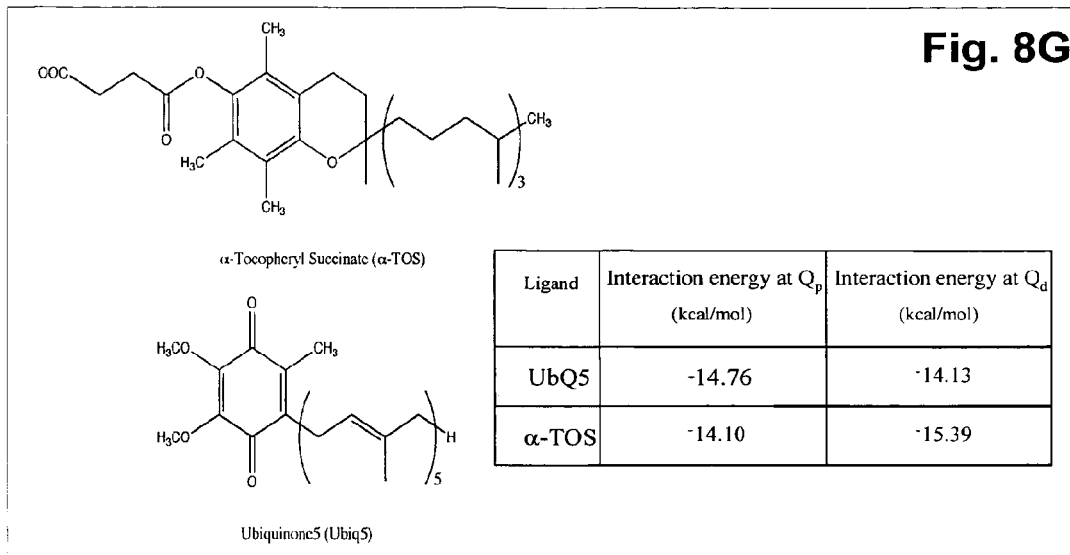
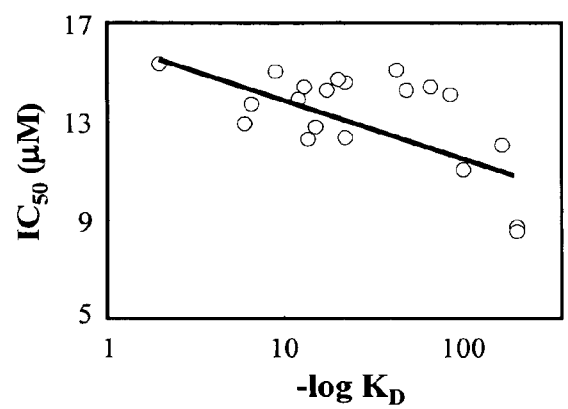
(low -> high binding affinity)
FIG. 9

FIG.10 (cont.)

start 0 size 500 select distinct s.sub_id from substance s, protomer p, catalog_item ci, catalog c , qury q where s.sub_id = ci.sub_id_fk and ci.cat_id_fk = c.cat_id and c.free=1 and p.sub_id_fk = s.sub_id and q.qury_id = 238521 and q.sub_id = s.sub_id limit 0,500

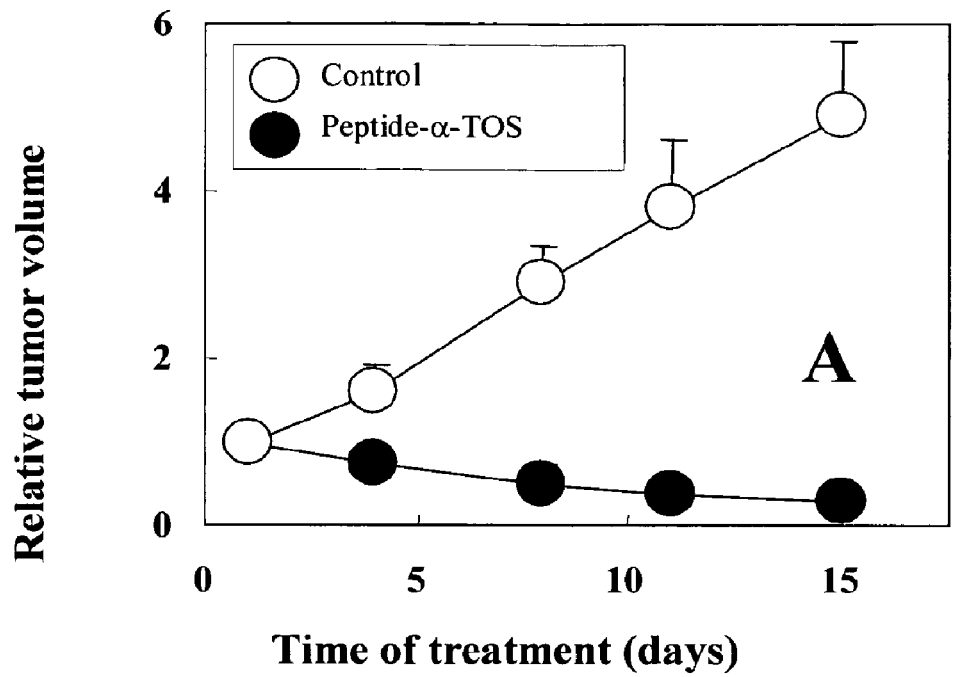
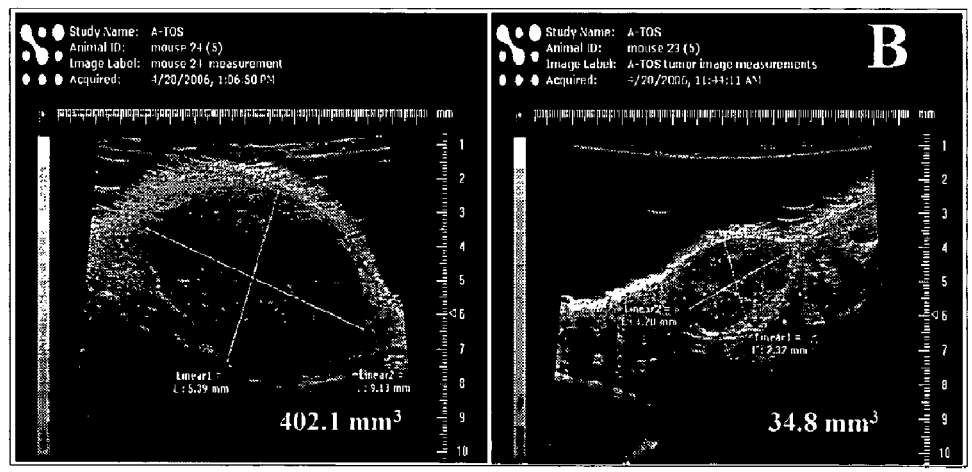
untreated    α- TOS treated
Fig. 11

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: Synthesized

<400> SEQUENCE: 1

Leu Thr Val Ser Pro Trp Tyr
1               5

<210> SEQ ID NO 2
<211> LENGTH: 21
<212> TYPE: DNA
<213> ORGANISM: Artificial Sequence
<220> FEATURE:
<223> OTHER INFORMATION: Synthesized

<400> SEQUENCE: 2
cctgcccttc tacaaccagg a                                                    21

<210> SEQ ID NO 3
<211> LENGTH: 19
<212> TYPE: RNA
<213> ORGANISM: Artificial Sequence
<220> FEATURE:
<223> OTHER INFORMATION: Synthesized

<400> SEQUENCE: 3
ugcccuucua caaccagga                                                       19

<210> SEQ ID NO 4
<211> LENGTH: 19
<212> TYPE: RNA
<213> ORGANISM: Artificial Sequence
<220> FEATURE:
```

```
<223> OTHER INFORMATION: Synthesized

<400> SEQUENCE: 4
uccugguugu agaagggca                                                19
```

PRO-OXIDANT ANTI-CANCER COMPOUNDS

CROSS-REFERENCES

This application is a U.S. National Stage Application under 35 U.S.C. 371 of international application no. PCT/AU2007/001371 filed on Sep. 17, 2007 which claims priority from Australian patent application no. AU 2006905109 filed on Sep. 15, 2006. All references noted herein are hereby incorporated by reference.

TECHNICAL FIELD

This invention relates, inter alia, to anti-cancer compounds and to methods for treating or preventing cancer. In particular, the invention concerns pro-oxidant anti-cancer compounds, such as pro-oxidant forms of vitamin E that selectively interact with complex II of the mitochondrial respiratory chain of cancerous cells, generate reactive oxygen species and induce apoptosis of those cells.

BACKGROUND OF THE INVENTION

An ideal anti-cancer drug would be one that is active only when inside cancer cells and that targets essential components or disrupts essential processes of those cells. Mitochondria, supplying much of the cellular energy and key regulators of apoptosis, are emerging as effective targets that may provide the cell selectivity desired for anti-cancer therapy (Don and Hogg, 2004, Armstrong, 2006).

Cytotoxic drugs that act by selectively affecting mitochondria in cancer cells, 'mitocans', are proving to be highly attractive for the treatment of cancer since these compounds can work as potent anti-cancer agents with little or no side effects, as reported in animal studies (Ko et al, 2004). Mitocans disrupt the energy producing systems of cancer cell mitochondria, leading to increased reactive oxygen species (ROS) and activation of the mitochondrial dependent cell death signaling pathways inside cancer cells.

Mitocans include drugs affecting the following mitochondrial associated activities: hexokinase inhibitors; electron transport/respiratory chain blockers; activators of the mitochondrial membrane permeability transition pore targeting constituent protein subunits, either the voltage dependent anion-selective channel (VDAC) or adenine nucleotide transporter (ANT); inhibitors of Bcl-2 anti-apoptotic family proteins and Bax/Bid pro-apoptotic mimetics. Two prime examples of mitocans with little or no side effects are 3-bromopyruvate (3-BP) and α-tocopheryl succinate (α-TOS), both of which induce apoptosis in cancer cells with much greater efficacy than in normal cells (Ko et al, 2004, Geschwind et al, 2002, Xu et al, 2005, Neuzil et al, 2001, 2004).

One group of mitocans includes pro-oxidant analogues of vitamin E (Wang et al 2006). The great promise of pro-oxidant vitamin E analogues, epitomized by α-TOS, as anti-cancer drugs stems from studies with experimentally contrived cancers, such as human xenografts growing in nude mice, where they have been shown to suppress malignancy (reviewed in Neuzil et al, 2004). Such studies include colorectal (Neuzil et al, 2001, Weber et al, 2002) and lung carcinomas (Quin et al, 2005), melanomas (Malafa et al, 2002), as well as mesotheliomas (Tomasetti et al, 2004, Stapelberg et al, 2005). α-TOS has also been shown to promote breast cancer dormancy (Malafa et al, 2000) and suppress colon cancer metastases into the liver (Barnett et al, 2002).

Although vitamin E (α-tocopherol, α-TOH) acts as a potent anti-oxidant in cells, α-TOS, an esterified, redox-silent and pro-oxidant analogue of vitamin E, has distinctive properties. In contrast to α-TOH, α-TOS acts as a strong cell stressor, causing rapid production of ROS in a range of different cancer cell lines (Neuzil et al, 2004, Weber et al, 2003, Wang et al, 2005, Swettenham et al, 2005, Stapelberg et al, 2005). α-TOS also has the ability to bind to and inhibit Bcl-2/Bcl-xL (Done et al, 2006). Evidence to date suggests that the cancer cell-specific nature of α-TOS and the lack of toxic effect on normal cells occurs because normal cells are endowed with greater anti-oxidant defenses (Allen and Balin, 2003, Safford et al, 1994, Church et al, 1993) and/or contain high levels of esterases that inactivate α-TOS by releasing the succinate moiety, thereby producing the redox-active, non-apoptogenic α-TOH (Fariss et al, 2001, Neuzil et al, 2004, Neuzil and Massa, 2005).

Naturally occurring vitamin E consists of a mixture of eight compounds which differ by the methylation patterns of the chromanol ring (α-, β-, γ-, δ-tocopherol) and the number of double bonds of the phytyl side-chain (α-, β-, γ-, δ-tocotrienol). The role of these molecules as lipophilic anti-oxidants in vitro and in vivo is widely accepted. In addition, the non-anti-oxidant properties of members of the VE family have also been investigated (Azzi et al, 2002).

The vitamin E molecule can be divided into three different domains. The Functional Domain (1) arises from the substitution pattern at position C6 of the chromanol ring. This position determines whether the molecule behaves as redox-active or redox-silent, since a free hydroxyl group is essential for vitamin E to function as an anti-oxidant. The well documented anti-oxidant properties of the four tocopherol isomers resulted in their application in cancer clinical trials. None of these studies showed a positive outcome concerning the use of free tocopherols in cancer prevention (Pham and Plakogiannis, 2005). However, certain chemical modifications at C6 led to ethers (RO—), esters (RCOO—) and amides (RCONH—) that proved to be potent anti-neoplastic agents. See Table 1 below.

TABLE 1

Anti-proliferative activity of vitamin E analogues.
Compounds are sorted by the Signaling Domain.

| Nr | Functional Domain I (R1) | Signalling Domain II | Hydrophobic Domain III (R2) | $IC_{50}$ [μM] | Cell type | Ref |
|---|---|---|---|---|---|---|
| 1 | $^-O_2CCH_2CH_2COO-$ | $CH_3$ | | 43 | Jurkat, HBT11, MCF7, MCF7-C3 | Birringer et al, 2003 |

TABLE 1-continued

Anti-proliferative activity of vitamin E analogues.
Compounds are sorted by the Signaling Domain.

| Nr | Functional Domain I (R1) | Signalling Domain II | Hydrophobic Domain III (R2) | IC$_{50}$ [μM] | Cell type | Ref |
|----|---|---|---|---|---|---|
| 2  | CH$_3$COO— | | | $a$ | | |
| 3  | $^-$O$_2$CCH=CHCOO— | | | 22 | | |
| 4  | $^-$O$_2$CCH$_2$CH(CH$_3$)COO— | | | $b$ | | |
| 5  | $^-$O$_2$CCH$_2$(CH$_2$)$_2$COO— | | | $b$ | | |
| 6  | $^-$O$_2$CCH$_2$CH(CH$_3$)CH$_2$COO— | | | $b$ | | |
| 7  | $^-$O$_2$CCH$_2$C(CH$_3$)$_2$CH$_2$COO— | | | $b$ | | |
| 8  | $^-$O$_2$CC(CH$_3$)$_2$CH$_2$COO— | | | $b$ | | |
| 9  | H$_3$COOCCH$_2$CH$_2$COO— | | | | | |
| 10 | $^-$O$_2$CCOO— | | | $c$ | B16-F1/ nude mice | Kogure et a., 2005 |
| 11 | $^-$O$_2$CCH$_2$COO— | | | | | |
| 12 | $^-$O$_2$CCH$_2$CH$_2$CONH— | | | 13 | Jurkat, U937, Meso-2 | Tomic-Vatic et al, 2005 |
| 13 | $^-$O$_2$CCH=CHCONH— | | | 2 | | |
| 14 | H$_3$COOCCH$_2$CH$_2$CONH— | | | >100 | | |
| 15 | $^+$NH$_3$—CH$_2$COO— | | | $a$ | MCF7 | Arya et al, 1995 |
| 16 | $^+$NH$_3$Lys(NH$_3$)COO— | | | 12 | | |
| 17 | Lys-Lys(Lys)COO— | | | $a$ | | |
| 18 | CH$_3$O— | | | $a$ | Jurkat | Neuzil et al, 2001b |
| 19 | CH$_3$CH$_2$COO— | | | $d$ | A549 | Yano et al, 2005 |
| 20 | $^-$O$_2$CCH$_2$CH$_2$CH$_2$O— | | | $e$ | LNCaP, PC-3 MDA-MB-453 | Wu et al, 2004; Nishikawa et al, 2003 |
| 21 | $^-$O$_2$CCH$_2$O— | | | $f$ | MDA-MB-435, MCF7 | Shun et al, 2004 |
| 22 | $^-$O$_2$CCH$_2$— | | | 15-20$^g$ | MCF7 | Shiau et al, 2006 |
| 23 | (PET)O$_2$CCH$_2$CH$_2$COO— | | | $h$ | lung carcinoma cells/ nude mice | Youk et al, 2005 |
| 24 | $^-$O$_2$C(CH$_2$)$_5$COO— | | | $a$ | C1271 | Kogure et al, 2004 |
| 25 | C$_2$H$_5$OOCCH$_2$CH$_2$COO— | | | $a$ | | |
| 26 | nicotinic acid | | | $a$ | | |
| 27 | $^-$O$_2$CCH$_2$CH(SePh)COO— | | | ? | prostate | Vraka et al, 2006 |
| 28 | all-trans retinoic acid | | | 0.1-1 | NB4, HT93 | Makishima et al, 1996, 1998 |
| 29 | 9-cis retinoic acid | | | $b$ | | |
| 30 | HOPO$_2$O— | | | $b$ | RASMC, THP-1 | Munteanu et al, 2004 |
| 31 | Toc-OPO$_2$O— | | | $b$ | | |
| 32 | $^-$O$_2$CCH$_2$CH$_2$COO— | ![structure with R1 on ring, CH$_3$ groups at 5,7,8 positions, R2 and CH$_3$ on chromanol] | | 50% of α-TOS | Jurkat, HVT11, MCF7, MCF7-C3, U937, Meso-2 | Birringer et al, 2003; Tomic-Vatic et al, 2005 |
| 33 | $^-$O$_2$CCH$_2$CH$_2$COO— | ![structure with R1, H$_3$C at 7, CH$_3$ at 8, R2 and CH$_3$ on chromanol] | | $b$ | Jurkat, HBT11, MCF7, MCF7-C3 | Birringer et al, 2003; Vraka et al, 2006 |
| 34 | $^-$O$_2$CCH$_2$CH(SePh)COO— | | | $b$ | prostate | Vraka et al, 2006 |

TABLE 1-continued

Anti-proliferative activity of vitamin E analogues.
Compounds are sorted by the Signaling Domain.

| Nr | Functional Domain I (R1) | Signalling Domain II | Hydrophobic Domain III (R2) | IC$_{50}$ [μM] | Cell type | Ref |
|---|---|---|---|---|---|---|
| 35 | $^-O_2CCH_2CH_2COO-$ | chroman ring with R1 at 6-position, CH$_3$ at 8-position, R2 and CH$_3$ at 2-position | | 66 | Jurkat, HBT11, MCF7, MCF7-C3 | Birringer et al, 2003; Tomic-Vatic et al, 2005 |
| 36 | $^-O_2CCH=CHCOO-$ | | | 49 | Jurkat, U937, Meso-2 | Tomic-Vatic et al, 2005 |
| 37 | $^-O_2CCH_2CH_2CONH-$ | | | 20 | | |
| 38 | $^-O_2CCH=CHCONH-$ | | | 9 | | |
| 39 | $H_3COOCCH_2CH_2COO-$ | | | $a$ | | Birringer et al, 2003 |
| 40 | HO— | | | $b$ | PC-3 | Galli et al, 2004 |

$^a$No effect;
$^b$inhibition of cell proliferation;
$^c$much more cytotoxic than α-TOS;
$^d$less effective than 54;
$^e$the ether analogue is less effective than a-TOS itself;
$^f$comparable to α-TOS;
$^g$EC$_{50}$ [μg/ml];
$^h$more efficient than α-TOS.

TABLE 2

Anti-proliferative activity of vitamin E analogues with a modified Hydrophobic Domain.

| Nr | Functional Domain I (R1) | Signalling Domain II | Hydrophobic Domain III (R2) | IC$_{50}$ [μM] | Cell type | Ref |
|---|---|---|---|---|---|---|
| 41 | $^-O_2CCH_2CH_2COO-$ | chroman with R1 at 6, CH$_3$ at 5, H$_3$C at 7, CH$_3$ at 8, R2 and CH$_3$ at 2 | COO$^-$ | | Jurkat, HBT11, MCF7, MCF7-C3 | Birringer et al, 2003 |
| 42 | HO— | | isoprenoid chain (n=2) | $a$ | LNCaP, PC-3 | Shiau et al, 2006 |
| 43 | $^-O_2CCH_2CH_2COO-$ | | | 4-9 | | |
| 44 | $^-O_2CCH_2CH_2O-$ | | | 4-8 | | |
| 45 | $^-O_2CCH_2CH_2COO-$ | | isoprenoid chain (n=1) | 8-19 | | |
| 46 | | | CH$_3$ | >100 | | |
| 47 | $^+NH_3Lys(NH_3)COO-$ | | CH$_2$—OH | 194 | MCF7 | Arya et al, 1995 |
| 48 | | | CH$_2$—O-nC$_5$H$_{11}$ | 22 | | |
| 49 | | | CH$_2$—OC(O)nC$_4$H$_9$ | 15 | | |
| 50 | | | CH$_2$—O-cholic acid | 4 | | |
| 51 | HO— | | CH$_2$CH$_2$COO$^-$ | $b$ | PC-3 | Galli et al, 2004 |

TABLE 2-continued

Anti-proliferative activity of vitamin E analogues with a modified Hydrophobic Domain.

| Nr. | Functional Domain I (R1) | Signalling Domain II | Hydrophobic Domain III (R2) | $IC_{50}$ [μM] | Cell type | Ref |
|---|---|---|---|---|---|---|
| 52 | HO— | 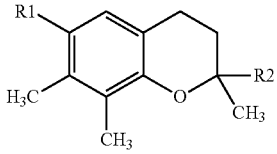 | $CH_2CH_2COO^-$ | c | | |

[a] No effect;
[b] weak inhibition at 50 μM;
[c] 82% inhibition at 10 μM.

TABLE 3

Anti-proliferative activity of vitamin E analogues. Compounds are sorted by the Signaling Domain.

| Nr. | Functional Domain I (R1) | Signalling Domain II | Hydrophobic Domain III (R2) | $IC_{50}$ [μM] | Cell type | Ref. |
|---|---|---|---|---|---|---|
| 53 | HO— | 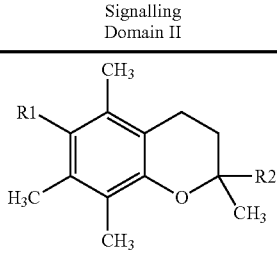 | 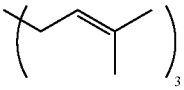 | 210 | MDA-MB-435 | Guthrie et al, 1997 |
| | | | | 14 | MCF7 | He et al, 1997 |
| | | | | 110 | B16(F10) | |
| 54 | $CH_3CH_2COO$— | | | a | A549 | Yano et al, 2005 |
| 55 | HO— | | 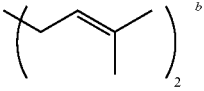 | b | Jurkat, HBT11, MCF7, MCF7-C3 | Birringer et al, 2003 |
| 56 | HO— | 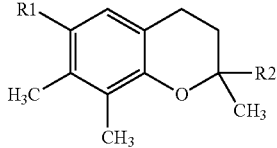 | 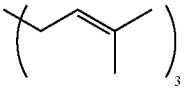 | 4 | neoplastic + SA mammary epithelial cells | Shah and Sylvester, 2005 |
| | | | | 15[c] | MCF7 | He et al, 1997 |
| | | | | d | Jurkat, HBt11, MCF7, MCF7-C3 | Birringer et al, 2003 |
| | | | | 20 | B16(F10) | He et al, 1997 |
| 57 | $^-O_2CCH_2CH_2COO$— | | | e | Jurkat, HBT11, MCF7, MCF7-C3 | Birringer et al, 2003 |
| | | | | f | prostate | Vraka et al, 2006 |
| 58 | $^-O_2CCH_2CH(SePh)COO$— | | | f | prostate | Vraka et al, 2006 |

TABLE 3-continued

Anti-proliferative activity of vitamin E analogues. Compounds are sorted by the Signaling Domain.

| Functional Nr. Domain I (R1) | Signalling Domain II | Hydrophobic Domain III (R2) | $IC_{50}$ [µM] | Cell type | Ref. |
|---|---|---|---|---|---|
| 59 HO— | R1 chromanol structure with two CH3 groups, R2 | | 10 | B16(F10) | He et al, 1997 |
| | | | $b$ | MDA-MB-435, MCF7 | Shun et al, 2004 |
| | | | $15^c$ | MCF7 | Nesaretnam et al, 1996 |
| 60 HO— | R1 chromanol structure with one CH3 group, R2 | | 0.9 | B16(F10) | He et al, 1997 |

$^a$Cytotoxic in 0-40 µM range;
$^b$very potent;
$^c$complete inhibition;
$^d$comparable to α-TOS;
$^e$2-fold more potent than γ- tocotrienol;
$^f$inhibition of cell proliferation.

The second domain, termed the Signaling Domain (II), exhibits some activities that are independent of the anti-oxidant properties of the tocopherols. These properties derive from the methylation pattern of the aromatic ring. For example, α-tocopherol has been reported to inhibit protein kinase C (PKC) by decreasing diacylglycerol (DAG) levels, while other tocopherols with similar anti-oxidant capabilities (e.g., β-tocopherol) do not inhibit PKC. Thus, the PKC inhibitory activity of α-tocopherol is independent of its anti-oxidant capacity (Tasinato et al, 1995; Kunisaki et al, 1995). In some cases, however, the biological activity of the various tocopherols is influenced by structural differences in the Signaling Domain, which do indeed have a profound impact on their anti-oxidant activity against certain species. γ-Tocopherol, for example, is a much better scavenger of reactive nitrogen oxide species (e.g., peroxynitrite) than α-tocopherol. Hence, the γ-molecule, which lacks a methyl group at C5, is readily nitrated at that site (Morton et al, 2002; Christen et al, 1997).

The lipophilic side chain of vitamin E isomers distinguishes between tocopherols with saturated isoprenyl units and tocotrienols with unsaturated isoprenyl units. The Hydrophobic Domain (III) determines whether the molecule can bind to lipoproteins and membranes respectively, or be degraded by phase 1 enzymes (Birringer et al, 2002; Neuzil and Massa, 2005).

Many tocopherol derivatives with a modified hydroxyl group have been tested for their pro-apoptotic activity (Table 1). The most prominent derivative tested has been α-TOS (entry 1) bearing a succinylester at position C6 of the chromanol ring. Due to its low $pK_a$ (<6), α-TOS is fully deprotonated under physiological conditions, leading to a detergent-like molecule which destabilizes mitochondrial membranes and has an effect on complex II. Dicarboxylic esters of tocopherols present the best studied compounds for structure-activity relationship (SAR). Strong apoptogens included α-tocopherol succinate (1), oxalate (10), and malonate (11), the latter two inducing non-selective cytotoxicity in mice inoculated with B16-F1 melanoma cells (Kogure et al, 2005). Even greater pro-apoptotic activity has been observed for unsaturated dicarboxylic acids like α-tocopheryl maleate (3) (Birringer et al., 2003) and α-tocopheryl fumarate. Increasing the chain length of the dicarboxylic acid led to decreased activity as shown for glutaric acid (5), methylated glutaric acids (6, 7, 8) (Birringer et al, 2003) with the pimelic acid (24) (Kogure et al, 2004) exhibiting no activity at all.

It has been established that the whole α-TOS molecule is necessary for its full apoptosis inducing activity (Birringer et al, 2003). Esterification of the free carboxyl group leads to non-charged derivatives without pro-apoptotic activity (9, 25). Aliphatic carboxylic acid esters, such as tocopheryl acetate and propionate (19), respectively, were inactive as was the methyl ether (18). Oral administration of α-TOS is not effective since the compound is cleaved by intestinal esterases (Wu et al, 2004b; Cheeseman et al, 1995). To overcome the problem of ester bond cleavage, compounds (20, 21) and a side chain-truncated derivative (42) have been synthesized, replacing the ester bond with an ether bond, since the latter is resistant to hydrolysis (Wu et al, 2004b; Nishikawa et al, 2003; Shun et al, 2004; Shiau et al, 2006). It should be noted that the replacement of the ether bond by a methylene group is sufficient to accelerate apoptosis (22) (Sanders et al, 2001).

When the ester bond is replaced by an amide bond, further enhancement of pro-apoptotic activity was observed (12, 13, 37, 38) (Tomic-Vatic et al, 2005). Again the unsaturated amides (13, 38) were superior to the saturated amides. The rationale for introducing an amide bond in place of the ester was based on the well-established fact that anilinic amides are much less prone to hydrolysis than the corresponding phenolic esters. Enhancing the stability of these tocopheryl ester derivatives would protect these molecules in viva, allowing them to stay intact longer, thereby increasing their bioavailability. The isosteric replacement of the esters by amides makes that linkage less prone to enzymatic hydrolysis as well. Several nonspecific esterases exist in the intestinal mucosal cells and in the blood. In contrast, peptidases exhibit a much narrower specificity. For example, prodrugs with an amino acid in an amide linkage are more stable in the intestine and blood than their corresponding ester analogues (Sugawara et at 2000).

The last group of compounds consisted of a series of lysine α-tocopheryl esters with a positively charged N-terminus (15-17). The hydrophilic ammonium functionality exerted similar pro-apoptotic effects to its carboxylate counterpart, suggesting a general motif is required for activity that consists of a lipophilic side chain and a hydrophilic head group. However, succinyl esters of long chain aliphatic alcohols (e.g., phytol and oleol) did not show any activity (Birringer et al, 2003).

A general SAR can be drawn from the data shown in Table 1:

1. To gain profound pro-oxidant and pro-apoptotic activity, modifications of the Functional Domain I required a hydrophilic head group consisting of a dissociated acid or a charged ammonium group.
2. The chain length and the degree of unsaturation of the Functional Domain determined the apoptogenic activity. Conformational restrictions appeared to potentiate the activity.
3. The chemical linkage of the Functional Domain is not limited to esters, and other functionalities prevented enzymatic degradation of the derivatives.

The substitution pattern of the chromanol ring is often not merely related to the anti-oxidant properties of the tocopherols (Azzi et al, 2002). Different biochemical observations emphasize the role of α-tocopherol in signaling and metabolic processes. Thus, α-tocopherol is selectively recognized in the liver by α-tocopherol transfer protein (α-TTP), a 32 kDa protein with a high affinity for α-tocopherol relative to the other tocopherols and tocotrienols. The relative affinities for α-TTP decrease with the loss of methylation of the chromanol ring (α-tocopherol 100%, β-tocopherol 38%, γ-tocopherol 9% and δ-tocopherol 2%) (Hosomi et al, 1997). The recently discovered tocopherol associated proteins (TAPs) show similar preferences in tocopherol binding (Yamauchi et al, 2001). In endothelial cells, thrombin-induced PKC activation and endothelin secretion are inhibited by α-tocopherol but not by β-tocopherol (Martin-Nizard et al, 1998). At the transcriptional level α-tocopherol causes up-regulation of α-tropomyosin expression (Aratri et al, 1999) and down regulation of LDL scavenger receptors SR-A and CD36, whereas β-tocopherol is ineffective (Ricciarelli et al, 2000; Devaraj et al, 2001). In addition, the substitution pattern is likely responsible for the rate of side chain degradation because in cell culture, γ- and δ-tocopherol are degraded much faster than α- or β-tocopherol (Birringer et al, 2001). Succinylation of the four tocopherol isomers produces the compounds 1, 32, 33 and 35. It is not surprising that of these, α-TOS (1) possesses the highest apoptogenic activity tested, followed by β-TOS (32), γ-TOS (33) and δ-TOS (35) as the least effective (Birringer et al, 2001). In general, the more highly methylated members of the tocopherol family are the most potent, but this trend is reversed for the tocotrienols (see below).

Succinylation of Trolox, a water soluble vitamin E derivative with a shortened side chain, resulted in the complete loss of pro-apoptotic activity. SAR experiments of various tocopherol succinates bearing truncated phytol side chains (Table 2, 43, 44, 45) revealed the highest level of apoptogenic activity in prostate cancer cells was obtained with derivatives where the side chain length was two isoprenyl units (43, 44). Computer assisted molecular modeling and co-immunoprecipitation experiments showed that the binding of Bak BH3 peptide to Bcl-$x_L$ and Bcl-2 was inhibited by the tocopherol analogues (Shiau et al, 2006). Central requirements for anti-neoplastic activity were succinylation of the chromanol ring and a minimum chain length of one isoprenyl unit (42, 46). A series of tocopheryl lysine esters with ether/ester linked Domain III side chains also showed a negative correlation between chain length and $IC_{50}$ (47-50) (Arya et al., 1998).

Tocotrienols are efficient anti-cancer agents and their pro-apoptotic property may be related to the inactivation of the Ras family of proteins. Tocotrienols exhibit their pro-apoptotic activity without modifications of the Functional Domain. The hierarchy in the Signaling Domain is also reversed, making δ-tocotrienol (59) the most potent agent in the murine B16-F10 melanoma cell model, followed by γ- (56) and α-tocotrienol (53) (Table 3; He et al, 1997). Interestingly, desmethyl tocotrienol (60), lacking all aromatic methyl groups, shows even higher activity with an $IC_{50}$ of 0.9 μM. This compound has been isolated from rice bran (Qureshi et al, 2000). A direct inhibitory action of tocotrienols has been proposed because the membrane anchoring cysteine residue of Ras proteins is modified by a common structural element, a farnesyl chain. Thus, Ras farnesylation and RhoA prenylation was inhibited by tocotrienols in A549 cells, a human lung adenocarcinoma cell line containing an activating ms mutation (Yano et al, 2005). To expand the short in vivo half life of tocotrienols, functional domains have been introduced. These modifications also enhanced the antiproliferative activity of the molecules (54, 57, 58). Truncation of the side chain also improved activity, similar to that found for compound 55.

A number of compounds where modifications have been made to the Functional Domain exhibit anti-proliferative activity and provide additional specialized properties. For example, α-Tocopheryl polyethylene glycol succinate (23) has been used as a vehicle for drug delivery systems. This compound was shown to possess anti-cancer activity against human lung carcinoma cells implanted in nude mice. The apoptosis inducing efficacy of the compound was not due to its increased uptake into cells, but rather due to an increased ability to generate reactive oxygen species (Youk et al, 2005). α-Tocopheryl phosphate (30) is believed to result from metabolism occurring during tocopherol-associated signaling (Negis et al, 2005). Mixtures of 30 and di-α-tocopheryl phosphate (31) inhibited proliferation in rat aortic smooth muscle cells and in human THP-1 monocytic leukaemia cells (Munteanu et al, 2004). The authors proposed that tocopheryl succinate and tocopheryl maleate may act in cancer cells by mimicking and substituting for tocopheryl phosphate and thereby cause the permanent activation of cellular signals.

Two experimental α-tocopheryl esters of all-trans retinoic acid (28) and 9-cis retinoic acid (29), respectively, have been used to reduce proliferation of acute promyelocytic leukaemia cells (Makishima et al, 1998). Trans-activation experiments with retinoid receptor responsive reporter constructs revealed that both of these compounds acted as agonists for retinoic acid receptors (RARs), γ-Carboxyethyl hydroxychroman (52), a degradation product of γ-tocopherol often found secreted in the urine, is able to reduce cell proliferation of PC-3 prostate cancer cells by inhibiting cyclin D1 expression (Galli et al, 2004).

SUMMARY OF THE INVENTION

The present inventors have found, inter alia, that selectively disrupting the transfer of electrons along the mitochondrial respiratory chain of cancerous cells, by way of targeting complex II (succinate-ubiquinone oxidoreductase) of the respiratory chain, can result in the generation of ROS and the death of those cells. In particular, the inventors have found that pro-oxidant forms of vitamin E may be effective anti-cancer compounds in that they are capable of selectively displacing ubiquinone from the ubiquinone-binding site of complex II of cancerous cells and blocking the normal transfer of electrons therefrom.

DETAILED DESCRIPTION OF THE INVENTION

According to a first aspect of the present invention, there is provided a pro-oxidant compound for selectively inducing the death of a cancerous cell, wherein said compound is capable of interacting with complex II (succinate-ubiquinone oxidoreductase) of a mitochondrial respiratory chain of the cancerous cell to generate reactive oxygen species within the cell.

According to a second aspect of the present invention, there is provided a pro-oxidan, compound for preventing or treating cancer, wherein said compound is capable of selectively interacting with mitochondrial complex II of a cancerous cell to generate reactive oxygen species within the cell.

According to a third aspect of the present invention, there is provided a method for inducing the death of a cancerous cell in a subject, said method comprising the step of administering to the subject a therapeutically effective amount of a pro-oxidant compound capable of selectively interacting with mitochondrial complex II of a cancerous cell to generate reactive oxygen species within the cell.

According to a fourth aspect of the present invention, there is provided a method for preventing or treating cancer in a subject, said method comprising the step of administering to the subject a therapeutically effective amount of a pro-oxidant compound capable of selectively interacting with mitochondrial complex II of a cancerous cell to generate reactive oxygen species within the cell.

According to a fifth aspect of the present invention, there is provided the use of a pro-oxidant compound in the preparation of a medicament for selectively inducing the death of a cancerous cell, wherein said compound is capable of interacting with mitochondrial complex II of a cancerous cell to generate reactive oxygen species within the cell.

According to a sixth aspect of the present invention, there is provided the use of a pro-oxidant compound in the preparation of a medicament for the prevention or treatment of cancer, wherein said compound is capable of selectively interacting with mitochondrial complex II of a cancerous cell to generate reactive oxygen species within the cell.

According to a seventh aspect of the present invention, there is provided a pro-oxidant compound for both detecting the presence of a cancerous cell and for selectively inducing the death of the cancerous cell, wherein said compound is capable of interacting with mitochondrial complex II of the cancerous cell to generate reactive oxygen species within the cell, and said compound has a detectable moiety enabling detection of the compound within the cancerous cell.

According to an eighth aspect of the present invention, there is provided a method for both detecting the presence of a cancerous cell and for selectively inducing the death of the cancerous cell in a subject, said method comprising the step of administering to the subject a therapeutically effective amount of a pro-oxidant compound capable of interacting with mitochondrial complex II of the cancerous cell to generate reactive oxygen species within the cell, and said compound has a detectable moiety enabling detection of the compound within the cancerous cell.

Any suitable type of pro-oxidant compound may be used and the compound may interact with mitochondrial complex II in any suitable way. Preferably, the compound binds to a ubiquinone-binding site of complex II and can readily displace the natural substrate ubiquinone, ubisemiquinone or ubiquinol (coenzyme Qs) or other quinones or related compounds preferentially interacting with complex II. Such substrates are specified, for example, in Briere et al, 2004, Tan et al, 1993, and Esposti et al, 1996.

According to a ninth aspect of the present invention, there is provided a pro-oxidant compound for selectively inducing the death of a cancerous cell, wherein said compound is capable of binding to a ubiquinone-binding site of complex II of a mitochondrial respiratory chain of the cancerous cell to generate reactive oxygen species within the cell.

According to a tenth aspect of the present invention, there is provided a pro-oxidant compound for preventing or treating cancer, wherein said compound is capable of binding to a ubiquinone-binding site of complex II of a mitochondrial respiratory chain of the cancerous cell to generate reactive oxygen species within the cell.

According to an eleventh aspect of the present invention, there is provided a method for inducing the death of a cancerous cell in a subject, said method comprising the step of administering to the subject a therapeutically effective amount of a pro-oxidant compound capable of binding to a ubiquinone-binding site of complex II of a mitochondrial respiratory chain of the cancerous cell to generate reactive oxygen species within the cell.

According to a twelfth aspect of the present invention, there is provided a method for preventing or treating cancer in a subject, said method comprising the step of administering to the subject a therapeutically effective amount of a pro-oxidant compound capable of binding to a ubiquinone-binding site of complex II of a mitochondrial respiratory chain of the cancerous cell to generate reactive oxygen species within the cell.

According to a thirteenth aspect of the present invention, there is provided the use of a pro-oxidant compound in the preparation of a medicament for selectively inducing the death of a cancerous cell, wherein said compound is capable of binding to a ubiquinone-binding site of complex II of a mitochondrial respiratory chain of the cancerous cell to generate reactive oxygen species within the cell.

According to a fourteenth aspect of the present invention, there is provided the use of a pro-oxidant compound in the preparation of a medicament for the prevention or treatment of cancer, wherein said compound is capable of binding to a ubiquinone-binding site of complex II of a mitochondrial respiratory chain of the cancerous cell to generate reactive oxygen species within the cell.

According to a fifteenth aspect of the present invention, there is provided a pharmaceutical or veterinary composition comprising the pro-oxidant compound according to the first, second, ninth or tenth aspect of the present invention, or a physiologically acceptable salt thereof, and a physiologically acceptable carrier.

Apoptosis may occur solely as a result of the increased levels of reactive oxygen species in the mitochondria of the cancerous cell, or the compound may be further pro-apoptotic by way of activating mitochondrial dependent cell death signaling pathways within the cell. Preferably, the compound generates reactive oxygen species by way of binding to complex II and is further pro-apoptotic by way of activating mitochondrial dependent cell death signaling pathways.

Preferably, the pro-oxidant compound is cleaved, processed or otherwise metabolized in non-cancerous cells to a harmless form lacking pro-oxidant activity.

Preferably, the compound is a pro-oxidant vitamin E analogue. The present inventors have found that pro-oxidant vitamin E analogues can bind to complex II and disrupt electron transfer to ubiquinone. The inventors have also found pro-oxidant vitamin E analogues to be pro-apoptotic. The present inventors have further found that pro-oxidant vitamin E analogues can be processed to harmless anti-oxidant forms in non-cancerous cells.

In contrast, thenoyltrifluoroacetone (TTFA), which also binds to complex II (Sun et al, 2005), is toxic to all cells (Zhang et al, 2001b). Although 3-BP also binds to complex II, it has not been characterized as having pro-oxidant activity.

A "pro-oxidant vitamin E analogue" is defined herein as a vitamin E analogue that, when located in mitochondria of a cancerous cell, is redox-silent and is capable of binding to a ubiquinone binding site of complex II and trigger the production of oxygen by-products of metabolism that can cause damage to the cell. An example of a pro-oxidant vitamin E analogue is α-tocopheryl succinate (α-TOS).

An "anti-oxidant vitamin E analogue", on the other hand, is a vitamin E analogue that has anti-oxidant (redox) activity when located in mitochondria of a cancerous cell, egg. α-tocopherol (α-TOH). Hence, the biological activities of pro-oxidant vitamin E analogue and anti-oxidant vitamin E analogue are directly opposed.

Examples of particularly preferred pro-oxidant vitamin E analogues are shown in Tables 1-3 above, Tables 4 and 5 below, and are discussed in the background section of this specification.

Alternatively, the compound may be selected from the group consisting of:

[(N'-amidinohydrazino)-(4-methoxyphenyl)-methyl]phosphinic acid;
N-(4-methoxy-6-methyl-pyrimidin-2-yl)benzenesulfonamide;
4,6-dimethyl-3-methylsulfonyl-2-propylsulfonyl-pyridine;
(4-formyl-5-hydroxy-6-methyl-3-pyridyl)methoxyphosphonic acid (pyridoxal phosphate);
3-(5-propoxy-2-sulfo-phenyl)propanoic acid;
3-[hydroxy-[(methyl-methylsulfonyl-amino)methyl]phosphoryl]propanoic acid;
(ethoxycarbonyl-(2-ethoxycarbonylethyl)amino)methylphosphinic acid;
1-[2-(3,7-dimethyl-2,6-dioxo-purin-1-yl)ethylideneamino]guanidine;
8-sulfoquinoline-2,4-dicarboxylic acid;
2-(2-carboxyethyl-hydroxy-phosphoryl)-3-(2-furyl)propanoic acid;
3-[2S,4S,5R)-5,6-dichloro-2,4-dimethyl-1-oxohexyl]-4-hydroxy-5,6-dimethoxy-2(H)-pyridinone (Atpenin A5);
2,3-dimethoxy-5-geranyl-6-methyl-1,4-benzoquinone (Ubiquinone-2);
2-(1-methylhexyl)-4,6-dinitrophenol (Dinitrophenol-17);
5,6-dihydro-2-methyl-1,4-oxathiin-3-carboxanilide (Carboxin);
4,4,4-trifluoro-1-(2-thienyl)-1,3-butanedione (2-Thenoyitrifluoroacetone); and
ubiquinone derivatives as described in Gu L Q et al, 1990; He D Y et al, 1994, Yang F et al, 1991, Yankovskaya et al, 1996, and Yabunaka et al, 2002, the entire contents of which are incorporated herein by way of cross-reference.

The compound may be used to induce the death of any type of cancerous cell in a subject, eg. lung, liver, kidney, brain, prostate, breast, ovary, lymphoid, skin, eye, colon, gastric, oral squamous, and hematopoietic systems.

Surprisingly, the compound α-TOS has been found by the present inventors to efficiently kill erbB2-low or -high cancer cells. The compound α-TOS has also been found by the inventors to treat mesothelioma.

Surprisingly, the compound α-TOS has been found by the present inventors to induce the death of both normoxic and hypoxic cancerous cells. Thus, the compound has the advantage that it may be used to induce the death of both early and late stage tumors in a subject.

The subject for treatment may be a human, mammal or animal. Preferably, the subject is a human or other type of mammal.

The compound may be included in the composition as pharmaceutically or veterinarially acceptable derivatives thereof. As used herein "derivatives" of the compound includes salts, coordination complexes with metal ions such as $Mn^{2+}$ and $Zn^{2+}$, esters such as in vivo hydrolysable esters, free acids or bases, hydrates, or pro-drugs. Compounds having acidic groups such as phosphates or sulfates can form salts with alkaline or alkaline earth metals such as Na, K, Mg and Ca, and with organic amines such as triethylamine and Tris (2-hydroxyethyl) amine. Salts can also be formed between compounds with basic groups, such as amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques that will be well known to those of skill in the art.

The composition may be administered to the subject in either a prophylactically effective or a therapeutically effective amount as necessary for the particular situation under consideration. The actual amount of the compound in the composition and rate and time-course of administration of the composition, will depend on the nature and severity of the cancer being treated or the prophylaxis required. Prescription of treatment such as decisions on dosage and the like will be within the skill of the medical practitioner or veterinarian responsible for the care of the subject. Typically however, compositions for administration to a human subject will include between about 0.01 and 100 mg of the compound per kg of body weight and more preferably between about 0.1 and 10 mg/kg of body weight. When α-tocopheryl succinate or other analogue is applied transdermally to a human subject, the serum level of the compound is preferably in the vicinity of its $IC_{50}$ value, approximately 40-50 µM.

The composition may be administered to the subject in any suitable way, including: parenterally, topically, orally, by inhalation spray, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The carrier may comprise any suitable diluent, adjuvant, excipient, buffer, stabilizer, isotonicising agent, preservative or anti-oxidant. It will be appreciated that the carrier should be non-toxic and should not interfere with the efficacy of the compound. The precise nature of the carrier or any other additive to the composition will depend on the route of administration and the type of treatment required. See, for example, Alfonso R. Gennaro. Remington: The Science and Practice of Pharmacy, 20th Edition. Baltimore, Md.: Lippincott Williams & Wilkins, 2000, and Goodman and Gilman's The Pharmaceutical Basis of Therapeutics, Pergamon Press, New York, N.Y., the entire contents of which are incorporated herein by reference. Pharmaceutical compositions may be produced, for instance, by means of conventional mixing, dissolving, granulating, dragee-making, levigating, emulsifying, encapsulating, entrapping or lyophilizing processes.

Sterile injectable forms of the composition may be aqueous or oleaginous suspension. Such forms will be known to those of skill in the art. For intravenous, cutaneous or subcutaneous injection, or injection at a site where treatment is desired, the composition may be in the form of a parenterally acceptable aqueous solution which has suitable pH, isotonicity and stability.

Orally acceptable dosage forms of the composition include capsules, tablets, pills, powders, liposomes, granules, spheres, dragees, liquids, gels, syrups, slurries, suspensions and the like. Suitable oral forms will be known to those of skill in the art. A tablet can include a solid carrier such as gelatine or an adjuvant or an inert diluent. Liquid pharmaceutical compositions generally include a liquid carrier such as water, petroleum, animal or vegetable oils, a mineral oil or a synthetic oil. Physiological saline solution, or glycols such as ethylene glycol, propylene glycol or polyethylene glycol may be included. Such compositions and preparations will generally contain at least 0.1 wt % of the compound and preferably up to about 25 wt %, depending on its solubility in the given carrier.

The composition may be administered topically, especially when the target of treatment includes areas or organs readily accessible by topical application, including cancers of the eye, the skin, or the lower intestinal tract. The composition may be applied in the form of a solution, suspension, emulsion, ointment, cream, lotion, paste, gel, foam, or aerosol. Suitable topical forms will be known to those of skill in the art.

The composition may include a delivery vehicle for delivering the compound to a particular organ, tissue or type of cancer, and/or for ensuring that the compound is able to be, for instance, absorbed through the skin or ingested through the gut without loss of biological efficacy. Delivery vehicles may comprise, for example, lipids, polymers, liposomes, emulsions, antibodies and/or proteins. Liposomes are particularly preferred for delivering the compound through the skin to, say, treat mesothelioma.

The composition may be delivered using a sustained-release system, such as semipermeable matrices of solid hydrophobic polymers containing the compound. Various sustained-release materials are available and well known by those skilled in the art. Sustained-release capsules may, depending on their chemical nature, release the compound for about 1 to 20 weeks.

The compound may be in the form of a pro-drug. The pro-drug may have protective groups such that the activity of the compound is not compromised when the composition is taken, say, orally. The pro-drug may deliver the active compound to a particular organ or cell type. Suitable pro-drug forms and protective groups will be known to those of skill in the art. Preferably, an adduct of α-TOS is linked to the heptapeptide LTVSPWY (SEQ ID NO 1), for targeting cancer cells over-expressing the receptor tyrosine kinase, erbB2.

A subject may be administered the composition comprising the compound together with one or more other actives to achieve an optimal prophylactic or therapeutic effect. The actives may be, for example, alkylating agents, angiogenesis inhibitors, anti-androgens, anti-estrogens, anti-metabolites, apoptosis agents, aromatase inhibitors, cell cycle controlling agents, cell stressor, cytotoxics, cytoprotectant, hormonals, immunotherapy agents, kinase inhibitors, monoclonal antibodies, platinum agents, a respiratory inhibitor, retinoid, signal transduction inhibitors, taxanes and topoisomerase inhibitors. Particularly preferred agents include glycolytic inhibitors such as 2-deoxyglucose and 3-BP. Other particularly preferred agents include TRAIL and Akt1 inhibitors, as well as other mitocans as reviewed in Ralph S J et al, 2006, Neuzil J, Tomasetti et al, 2007, and Neuzil J, Dong et al, 2007, the entire contents of which are incorporated herein by way of cross-reference.

The present inventors have found, for example, that cancer cells are rendered more sensitive to killing by the combination of α-TOS and 3-BP (as well as with other drug combinations) compared with either drug used alone.

Preferably, the composition is administered parenterally or topically. The particularly preferred pro-oxidant vitamin E analogues are α-tocopheryl succinate, α-tocopheryl maleate, tocopheryl maleyl amide, and 2,5,7,8-tetramethyl-2R-(4R, 8R,12-trimethyltridecyl)-chroman-6-yloxyacetic acid (α-tocopheryloxyacetic acid). The preferred carrier for the esters α-tocopheryl succinate, α-tocopheryl maleate and α-tocopheryl maleyl amide is a transdermally applicable cream, such as the liposome-based cream "Lipoderm". The non-hydrolysable ether analogue, α-tocopheryloxyacetic acid, is preferably delivered orally.

Any suitable type of detectable moiety may be used and the compound may be detected in any suitable way. The detectable moiety may be a fluorescent dye (eg. Rhodamine 123) or a radio-labeled cation. Such detectable moieties may allow the simultaneous practice of an additional anti-cancer therapy, eg. photodynamic therapy.

According to a sixteenth aspect of the present invention, there is provided a method of identifying a chemical entity that is capable of inducing the death of a cancerous cell, said method comprising the steps of
  (i) introducing a test compound into mitochondria of a first cancerous cell and introducing a control compound known not to induce cancer cell death to a second cancerous cell; and
  (ii) assaying for the binding of the compounds to mitochondrial complex II and the generation of reactive oxygen species within the mitochondria of the first and second cancerous cells, and assaying for death of those cancerous cells by the test and control compounds,
wherein the complex II binding, the generation of reactive oxygen species and the death of the first cancerous cell by the test compound relative to the control compound indicates that a chemical entity capable of inducing cell death has been identified.

Preferably, the chemical entity is a pro-oxidant vitamin E analogue that binds to a ubiquinone binding site of complex II.

Preferably, high-throughput screening is used such that many test compounds may be screened at the same time.

According to a seventeenth aspect of the present invention, there is provided a chemical entity when identified by the method according to the sixteenth aspect of the invention.

According to an eighteenth aspect of the present invention, there is provided an isolated or purified complex comprising a compound according to the first, second, ninth or tenth aspect of the invention bound to mitochondrial respiratory chain complex II or one or more sub-units thereof.

Preferably, the compound is a pro-oxidant vitamin E analogue such as α-TOS. Preferably, the mitochondrial respiratory chain complex II is mammalian and more preferably of human origin.

According to a nineteenth aspect of the present invention, there is provided a crystal or crystallisable composition comprising a compound according to the first, second, ninth or tenth aspect of the invention bound to mitochondrial respiratory chain complex II or one or more subunits thereof Preferably, the compound is a pro-oxidant vitamin E analogue such as α-TOS. Preferably, the mitochondrial respiratory chain complex II is mammalian and more preferably of human origin.

According to a twentieth aspect of the present invention, there is provided a method for identifying or designing a chemical entity capable of binding to a ubiquinone binding site of mitochondrial respiratory chain complex II, said method comprising the steps of:
  (i) computer modeling the interaction between respiratory chain complex II and at least one vitamin E analogue that binds to complex II and disrupts electron flow to ubiquinone; and
  (ii) using data generated by the computer modeling to identify or design a chemical entity capable of binding to complex II and disrupting electron flow to ubiquinone.

Preferably, the at least one vitamin E analogue has pro-oxidant activity and promotes the generation of reactive oxygen species, such as α-TOS. More preferably, a plurality of vitamin E analogues that bind to complex II and disrupt electron flow to ubiquinone are used in step (i).

Preferably, the mitochondrial respiratory chain complex II is mammalian and more preferably of human origin.

According to a twenty first aspect of the present invention, there is provided a chemical entity when identified or designed according to the twentieth aspect of the present invention.

Preferably, the chemical entity is a pro-oxidant vitamin E analogue having a complex II binding affinity approximately equal to or greater than ubiquinone, or a chemical entity selected from the following:
[(N'-amidinohydrazino)-(4-methoxyphenyl)-methyl]phosphinic acid;
N-(4-methoxy-6-methyl-pyrimidin-2-yl)benzenesulfonamide;
4,6-dimethyl-3-methylsulfonyl-2-propylsulfonyl-pyridine;
(4-formyl-5-hydroxy-6-methyl-3-pyridyl)methoxyphosphonic acid (pyridoxal phosphate);
3-(5-propoxy-2-sulfo-phenyl)propanoic acid;
3-[hydroxy-[(methyl-methylsulfonyl-amino)methyl]phosphoryl]propanoic acid;
(ethoxycarbonyl-(2-ethoxycarbonylethyl)amino)methylphosphinic acid;
1-[2-(3,7-dimethyl-2,6-dioxo-purin-1-yl)ethylideneamino] guanidine;
8-sulfoquinoline-2,4-dicarboxylic acid;
2-(2-carboxyethyl-hydroxy-phosphoryl)-3-(2-furyl)propanoic acid;
3-[2S,4S,5R)-5,6-dichloro-2,4-dimethyl-1-oxohexyl]-4-hydroxy-5,6-dimethoxy-2(1H)-pyridinone (Atpenin A5);
2,3-dimethoxy-5-geranyl-6-methyl-1,4-benzoquinone (Ubiquinone-2);
2-(1-methy)hexyl)-4,6-dinitrophenol (Dinitrophenol-17);
5,6-dihydro-2-methyl-1,4-oxathiin-3-carboxanilide (Carboxin);
4,4,4-trifluoro-1-(2-thienyl)-1,3-butanedione (2-Thenoyltrifluoroacetone); and
ubiquinone derivatives as described in Gu L Q et al, 1990; He D Y et al, 1994, Yang F et al, 1991, Yankovskaya et al, 1996, and Yabunaka et al, 2002.

According to a twenty second aspect of the present invention, there is provided a method of identifying a chemical entity that is capable of inducing the death of a cancerous cell, said method comprising the steps of:
  (i) introducing a test compound into mitochondria of a cancerous cell; and
  (ii) assaying for displacement of a natural ubiquinone substrate of a ubiquinone-binding site of complex H of the mitochondria and assaying for death of the cancerous cell,
wherein the displacement of the natural ubiquinone substrate and the death of the cancerous cell by the test compound indicates that a chemical entity capable of inducing cell death has been identified.

According to a twenty third aspect of the present invention, there is provided a chemical entity when identified according to the twenty second aspect of the present invention.

Studies of particular types of human neuronal malignancies, the pheochromocytomas and paragangliomas as well as leiomyomas and renal-cell carcinomas, provided insight into one protective device whereby cancer cells promote their own survival. This process has become known as "pseudohypoxia" as distinct from the usual pathway for hypoxic development of cancers. This is because these cancers show mutations that make the cells behave as if they were hypoxic, even when normal levels of oxygen are present. Thus, in the pseudohypoxic cancers, somatic mutations occur in either the succinate dehydrogenase (SDH) or fumarate hydratase (FH, or fumarase) enzymes that are part of the tricarboxylic acid (TCA) cycle linking between glucose metabolism in the cytosol and oxidative phosphorylation in the mitochondria. SDHA encodes the enzymatic subunit located on the matrix side of the inner mitochondrial membrane as a membrane bound protein associated with 3 other subunits, SDHB, SDHC and SDHD of the ubiquinone oxidoreductase complex II. Inherited or somatic mutations in SDHB, SDHC or SDHD genes are associated with phaeochromocytomas or paragangliomas, whereas those in the FH gene cause leiomyomas, leiomyosarcomas or renal cell cancers (Gottlieb E and Tomlinson I P, 2005; King A et al, 2006; Astuti D et al, 2003; Bayley J P et al, 2006).

As a consequence of mutation in the genes encoding SDH or FH, metabolic intermediates succinate and fumarate become elevated inside these cancer cells because the enzyme activity of SDH or FH is reduced. As a result of the reduced SDH enzyme activity, such cancers may be more or less sensitive to treatment with pro-oxidant compounds such as α-TOS. Cancers of the types phaeochromocytomas or paragangliomas, leiomyomas, leiomyosarcomas or renal cell cancers that are suspected to contain mutations in genes encoding SDH or FH subunits can be analysed by diagnostic tests for their levels of SDH or FH enzyme activity. The enzyme activity for SDH can be based on standard procedures as described in King, T S, 1967, based on the measurement of reduction of the CII substrate, DCPIP in the presence of cells or liver mitochondrial preparations measured at 600 nm, Reaction mixtures contain 0.5 mM NADH, 5 mM succinate, 10 mM KCN, 50 μM DCPIP and 50 μM PMS. Alternatively, any tetrazolium based dye reduction assay for analyzing complex II SDH activity as outlined for example in Berridge M V and Tan A S, 1993, and as reviewed in Berridge M V et al, 2005.

Alternatively, molecular or immunohistochemical analysis of SDH mutations can be used to detect such abnormalities. Methods include PCR based, DNA sequencing, RFLP analysis, SNP, gene array expression analysis and similar techniques as examples described in van Nederveen F H et al, 2007, Pollard P T et al, 2005, and Bayley J P et al, 2006.

According to a twenty fourth aspect of the present invention, there is provided a method of testing whether a subject having cancer is likely to respond to therapy comprising the administration of a pro-oxidant compound according to the first or second aspects of the invention, said method comprising the steps of:

(i) introducing the pro-oxidant compound into mitochondria of a cancerous cell sourced from said subject; and
(ii) assaying for the binding of the pro-oxidant compound to a ubiquinone-binding site of complex II of the mitochondria and assaying for death of the cancerous cell, wherein the binding of the pro-oxidant compound and the death of the cancerous cell by the pro-oxidant compound indicates that the subject is likely to respond to the therapy.

(F) A Ligplot diagram showing the major interactions between the best docked conformation of α-TOS and the $Q_D$ binding site amino acid residues important for binding. Spatial distribution of critical amino acid residues involved in the binding interaction of α-TOS in the Qd pocket of complex II. Note: the hydrogen bonding (dotted lines) between the succinyl group of TOS and the Lysine residues D128, D135 of the complex II SDHD subunit. (G) Chemical structures of UbQ5 and α-TOS and interaction energies calculated for each of the structures binding to the $Q_P$ and $Q_D$ sites of complex II. NOTE: Panels A and E were prepared using Astex Viewer (Hartshorn, 2002), while Panels D and F were prepared using Ligplot (Wallace et al, 1995).

FIG. 9. Graph showing correlation between the biological activity of the different TOS analogues from Tables 4 and 5 (below) versus their calculated binding affinity for the $Q_P$ site of complex II. IC50: Concentration in micromolar that is needed of a particular drug to induce 50% killing of cancer cells in vitro. –log Kd: inverse log of the particular drug's binding affinity.

Figure 10:
Figure 10:
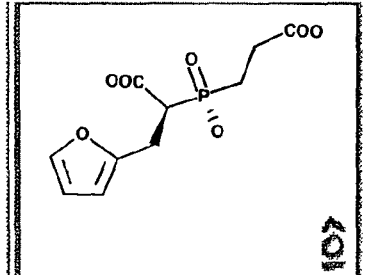

FIG. 10. Molecular modeling—complex II active site and other chemical entities. Details of the ten best ranked chemical entities identified by molecular modeling that potentially bind to the complex II Qp active site of mitochondria.

FIG. 11. Peptide conjugate LTVSPWY-α-TOS (SEQ ID NO 1) suppresses breast carcinomas. FVB/$N_2O_2$ c-neu female mice of >7 months of age with breast carcinomas, as detected by ultrasound imaging (USI), were treated by intraperitoneal injection of the vehicle or 5 μmol per mouse per dose of LTVSPWY-α-TOS (SEQ ID NO 1) solubilised in corn oil/ethanol (100:5, v/v) at times shown. The tumours were visualised and quantified using USI and are expressed relative to their volume at the onset of the treatment (A). Panel B presents representative images of a tumour from a control mouse (left) and a treated animal (5 μmol LTVSPWY-α-TOS (SEQ ID NO 1) per dose per mouse) (right) on day 15 of the experiment, revealing tumour volumes of 402.1 and 34.8 $mm^3$, respectively. The volume was ~40 $mm^3$ at the onset of the experiment for both tumors. Data shown are mean values±SD (n=4-6) and the USI images are representative of tumours from each group.

Figure 12:
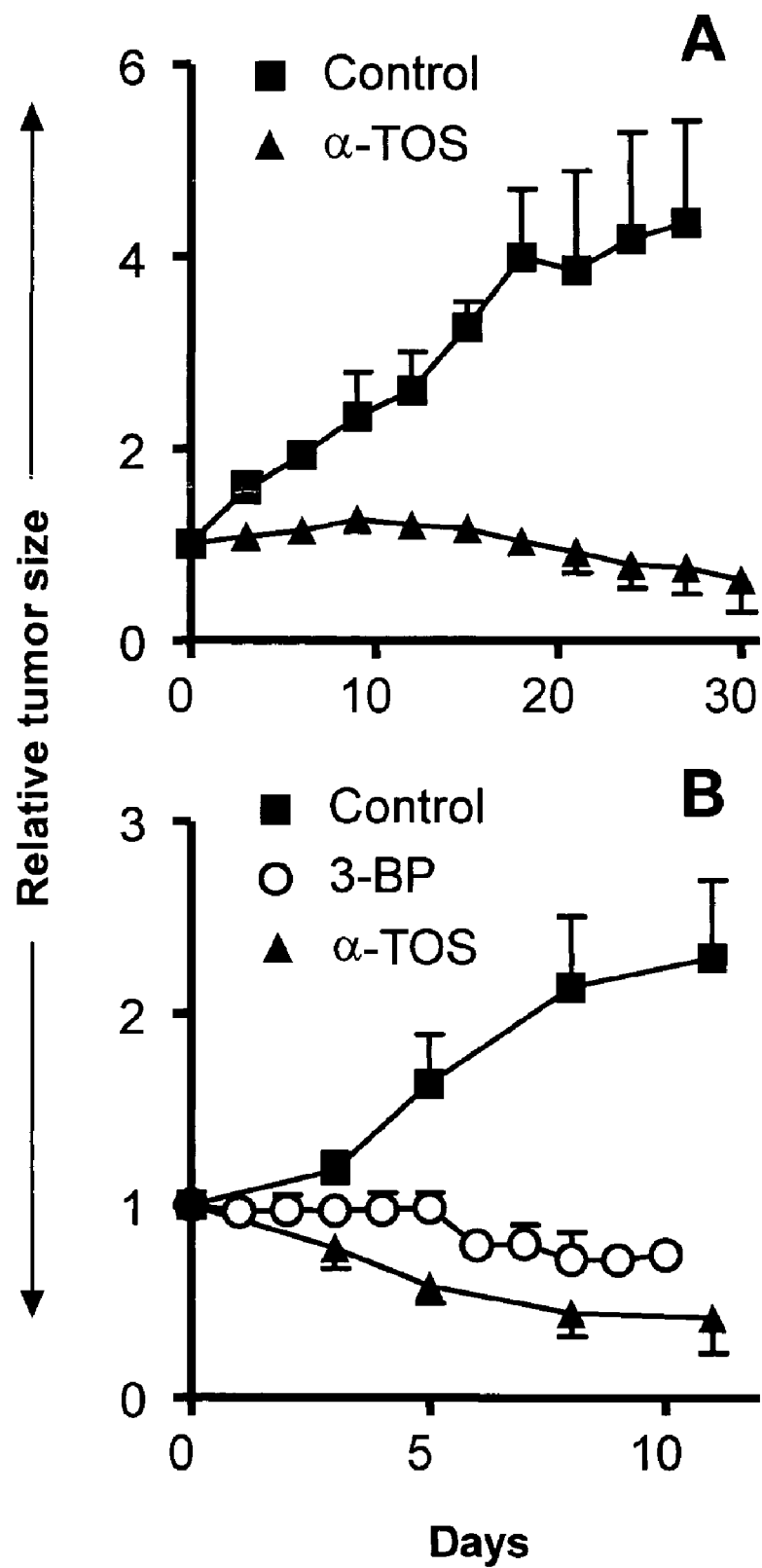

FIG. 12. Inhibition of breast cancer in mouse models by α-TOS. (A) Nude mice were inoculated with MCF-7 cells and, after tumors became established, the animals were treated once every 3 d with 10 μmoles per mouse of α-TOS dissolved in DMSO or with DMSO alone, by intraperitoneal (i.p.) injection. Tumor size was measured using calipers and was correlated to the size of the carcinomas at the onset of the therapy. Four animals were used in each group. The results shown are mean values±S.E. The symbol '*' denotes significant difference ($p<0.05$). (B) Female FVB/N erbB2 mice with palpable tumors (see General Materials and Methods) received either 10 μmoles α-TOS solubilized in corn oil/4% ethanol (n=11) or the corn oil/4% ethanol alone (control, n=9) by i.p. injection once every 3 d, or 0.2 μmoles 3-BP (n=8) in PBS at the tumor site every day. Tumor size was recorded using calipers. Two independent experiments were conducted. Results are represented as mean values±S.E. The symbol '*' denotes significant difference ($p<0.05$) in the analysis of variance between the 3-BP and α-TOS curves.

EXAMPLES

In order that this invention may be better understood, the following examples are set forth. These examples are for the purpose of illustration only and are not to be construed as limiting the scope of the invention in any manner.

General Materials and Methods

Cell culture and treatment. Human breast cancer cell lines MCF-7 with erbB2-low and MDA-MB-453 with erbB2-high level of expression, and a murine breast cancer cell line NeuTL with erbB2-high level of expression derived from the FVB/$N_2O_2$ rat c-neu transgenic mouse strain (Guy et al, 1992) were used in this study. Cells were cultured in DMEM with 10% FCS, 100 U/ml penicillin and 100 μg/ml streptomycin at 37° C. in a humidified atmosphere of 5% $CO_2$. Mitochondrial complex I-deficient (Breen and Scheffler 1979; DeFrancesco et al 1976; Scheffler et al 2004) and complex II-deficient cells (Albayrak et al 2003; Oostveen et al 1995) were grown in DMEM with 10% FCS, 10 g/ml glucose and non-essential amino acids.

At approximately 70% confluency, cells were treated with up to 50 μM α-TOS (Sigma), up to 100 μM 3-BP (Aldrich) or 30 ng/ml of human recombinant tumor necrosis factor-related apoptosis—inducing ligand (TRAIL) (Weber et al, 2002) under normoxic or hypoxic conditions. For hypoxia, cells overlaid with nitrogen-purged medium were placed in a hypoxic chamber pre-flushed extensively with nitrogen. The hypoxic chamber with cells was then placed in the incubator as required. α-TOS was dissolved in ethanol and used such that the final ethanol concentration in cell culture medium was <0.1% (v/v). Stock solutions of 3-BP were prepared in PBS prior to use.

ATP measurement. MDA-MB-453 and NeuTL cells were seeded at $2 \times 10^5$ per ml and MCF-7 cells at $1.2 \times 10^5$ per ml into 96-well tissue culture microtitre plates and allowed to recover overnight before use. Cells were incubated for 6 or 24 h with α-TOS or 3-BP under normoxia or hypoxia as described above. ATP levels were then measured using an ATP bioluminescence assay kit HSII (Roche Applied Science) according to the manufacturer's instructions. Briefly, control or treated cells were transferred into black microtitre plates after incubation for 5 min at room temperature with the cell lysis reagent. Luciferase reagent was added and the signal detected immediately using a Fluorostar Optima plate reader (BMG Labtech). Triplicate wells were read for each condition and data evaluated using a standard calibration curve prepared with known concentrations of ATP.

Assessment of ROS accumulation. Cellular ROS were detected with the probe dihydroethidinium (DHE) (Molecular Probes) by flow cytometry (Weber et al, 2003), or by trapping with 5,5-dimethyl-1-pyrroline N-oxide (DMPO; Sigma) using electron paramagnetic resonance (EPR) spectro-scopy (Weber et al, 2003). In some studies, the cells were pre-treated for 1 h with 2 μM MitoQ (James et al, 2005) or coincubated with SOD (PEG-SOD, 750 units/ml; Sigma).

Apoptosis assessment. Apoptosis was quantified using the annexin V-FITC method, which detects phosphatidyl serine externalized in the early phases of apoptosis (Boersma et al, 1996). Briefly, cells were plated at $10^5$ per well in 24-well plates and, after an overnight recuperation, treated with α-TOS or 3-BP alone or in combination. Floating and attached cells were harvested, washed with PBS, resuspended in 0.2 ml binding buffer (10 mM Hepes, 140 mM NaCl, 5 mM $CaCl_2$, pH 7.4), incubated for 30 min at 4° C. with 2 μl annexin V-FITC (PharMingen), supplemented with 200 μl of 50 μg/ml propidium iodide (PI; Sigma), and analyzed by flow cytometry (FACScalibur, Becton Dickinson) using channel 1 for annexin V-FITC binding and channel 2 for PI staining.

Cell death was quantified as the percentage of cells with increased annexin V binding and PI staining.

RNA interference (RNAi). Short-interfering RNA (siRNA) oligonucleotides with 3'-dTdT overhangs specific for Akt1 were synthesized by Qiagen. The sequences are as follows: target sequence: CCT GCC CTT CTA CAA CCA GGA (SEQ ID NO 2); siRNA duplex sequences: sense—r(UGC CCU UCU ACA ACC AGG A)dTdT (SEQ ID NO 3), antisense—r(UCC UGG UUG UAG AAG GGC A)dTdT (SEQ ID NO 4). The transfection of cultured MDA-MB-453 cells with siRNA was performed using OligofectAmine (Invitrogen) and OptiMEM according to the manufacturer's instructions. Briefly, cells were allowed to reach 50% confluency and supplemented with 60 µM siRNA pre-incubated with OligofectAmine and overlayed with OptiMEM. Cells were washed 24 h later with PBS, overlayed with complete DMEM and treated as required after an additional 24 h.

MTT assay. MTT solutions were prepared immediately before use by dissolving 2.5 mg/ml 3-(4,5-dimethyl-2,5-diphenyl 2H-tetrazolium bromide (MTT) (Sigma) in PBS alone or phenol red-free RPMI medium containing 20 mM succinic acid, pH 7.4. Stock solutions of 3-nitropropionic acid (3NPA) in ethanol, thenoyltrifluoroacetone (TTFA) in DMSO, 3-BP in PBS, α-TOS in DMSO, and MitoQ (Alleva et al, 2003, James et al, 2005) in ethanol were prepared. The drugs were tested on NeuTL cells cultured in exponential growth phase in 96-well microtitre plates using 4-8 replicate wells per dilution assayed. To assess the ability of MitoQ to restore MTT reduction, cells were pre-incubated for 60 min with 2 or 5 µM MitoQ. Final concentrations of ethanol or DMSO in cultures were ≦0.1%. Treated and control cells were allowed to reduce MTT to blue formazan crystals for 2 or 4 h at 37° C. and 5% $CO_2$. After incubation, culture supernatants were removed except for 30 µl, before the formazan crystals were solubilized by addition of 150 µl DMSO, and absorbance values were measured at 570 nm using a Fluorostar Optima plate reader.

Preparation of sub-mitochondrial particles (SMPs) from isolated rat liver. Rat liver mitochondria were prepared by differential centrifugation according to the modified method of Rice and Lindsay, 1997. 2 ml of mitochondrial pellet were resuspended in 15 ml of 20 mM $KH_2PO_4$ pH 7.4 and sonicated at a setting of 80 Watt for 3×15 s. The sonicated solution was then centrifuged at 6,500×g for 7 min. The supernatant fraction was kept on ice and the remaining pellet resuspended and sonicated again. The sonicated solution was centrifuged as before and the supernatant removed from the second centrifugation step combined with that from the first centrifugation. The combined supernatant was recentrifitged at 108,000×g for 1 h. The pellet of SMPs was resuspended in 5 ml of 20 mM $KH_2PO_4$ pH 7.4 and stored frozen at −20° C. until used.

Preparation of membrane vesicles from *Paracoccus denitrificans*. *P. denitrificans* CCM 982 (NCIB 8944) was grown anaerobically at 30° C. in a medium containing 50 mM succinate as the carbon source and 10 mM nitrate as the terminal acceptor. Membranes were prepared from harvested cells by treating with lysozyme according to Burnell et al (1975). After dilution in 0.1 M Na phosphate, pH 7.3, to a final protein concentration of approximately 20 mg/ml, the membranes were stored at −20° C. in 1 ml aliquots until used. The protein concentration was determined using the bicinchoninic acid method and an iEMS plate reader (Labsystem, Finland).

Measurement of mitochondrial complex II and complex I activity. A time course for the reduction of the complex II substrate 2,6-dichlorophenol indophenol (DCIP) by the mitochondrial preparations was followed by measuring the absorbance at 600 nm in 1 cm cuvettes containing a 1 ml reaction volume ($\epsilon_{600}$=21×10$^3$ M$^{-1}$cm$^{-1}$). The reaction components included NADH, 0.5 mM; succinate, 5 mM; KCN, 10 mM; DCIP, 50 µM; PMS, 50 µM. For each assay point, 0.5 mg sample protein was used and α-TOS was added at either 100 or 300 µM as indicated. The change in absorbance of DCIP was measured using a spectrophotometer (UVIKON XL, Secomam) and replicate samples were assayed (n=3). When measuring the complex I (NADH dehydrogenase activity), PMS was omitted. For the control reactions without α-TOS, the diluent DMSO was added so that the final concentration was <0.1% (v/v).

Molecular modeling—complex II and vitamin E analogues. The crystal structure of mitochondrial respiratory membrane protein complex II from porcine heart was obtained from the Brookhaven Protein Databank (code IZOY) (Sun et al, 2005). The complex contains four proteins. Three subunits in this complex, the iron-sulfur protein (Chain B), the large (Chain C) and small (Chain D) trans-membrane proteins are involved in the binding to UbQ. A BLAST search from the NCBI website revealed that the sequence identity between porcine and human complex II is very high, 97% for the iron-sulfur protein, 90% for the large trans-membrane protein and 94% for the small trans-membrane protein.

The protein structure was prepared for docking using AutoDock Tools (Sanner, 1999) with the heteroatoms being removed first. Polar hydrogens were added to the structure and Kollman United Atom charges were used for the protein atoms. UbQ5 was built from the crystal structure coordinates of the bound UbQ (IZOY) using InsightII (Accelrys, 2001), α-TOS was built from the crystal structure MOPHLB01 retrieved from the Cambridge Structural Database (Allen, 2002) by a sub-structure search for the ring system of α-TOS, again using InsightII. Both ligands were then prepared for docking by AutoDock Tools, which included merging non-polar hydrogens, assigning Gasteiger charges and defining the rotatable bonds.

Docking was performed using the Lamarckian Genetic Algorithm as implemented in Autodock 3.0.5. (Morris et al, 1998); two docking grids were prepared. Both were 126×126×126 points with a grid pacing of 0.375 Å, with the first centered on Tyr173 (Chain B) in the $Q_P$ site and the second centered on Trp134 (Chain D) in the $Q_D$ site. Default parameters were used except for the following, which were increased due to the relatively high number of rotatable bonds present in the ligands of interest (UbQ5=16, α-TOS=17):—ga_run=250, ga_pop_size=250, ga_num_evals=10,000,000. Also, the parameter rmstol was increased to 2.5, to produce more manageable clusters during the analysis phase of the calculation. Each docking calculation took just over 49 h using a 2 GHz G5 PowerPC Macintosh. Analysis of results was performed using scripts provided with AutoDock and docked structures were visualized using Astex Viewer (Hartshorn, 2002).

The Autodocking of other vitamin E analogues as shown in Tables 4 and 5 (below) was also performed as described above.

Molecular modeling—complex II Qp site and other chemical entities. A virtual library of 65,000 commercially available compounds was downloaded from the ZINC Database project (http://blaster.docking.org/zinc/). These compounds were filtered from a far larger database based on calculated physical properties, so they most resemble drug lead-like candidates (Teague, S J et al, 1999). They then underwent a diversity analysis to produce the final database. DOCK 6.1 (http://dock.compbio.ucsf.edu/DOCK 6/index.htm) was used in a virtual screening experiment to dock each of these compounds against the crystal structure of porcine complex II (1ZOY) and the top 1000 compounds based on interaction energy were identified. These final compounds were then subjected to a more rigorous docking experiment, once again using DOCK 6.1, and 10 compounds were identified using the visualization program Chimera (http://www.rbvi.ucsf.edu/chimera/), as being the most likely compounds to interact with porcine complex II.

Mouse tumor experiments. Nude mice were inoculated subcutaneously with MCF-7 cells ($2\times10^6$ cells/mouse). After tumors developed (diameter of 3-7 mm), mice were injected intraperitoneally with 10 μmoles α-TOS in DMSO every 3 days. Control mice were injected with an equal volume (100 μl) of DMSO only. Tumor size was estimated by measuring with digital calipers. A colony of transgenic $FVB/N_2O_2$ rat c-neu mice carrying the rat HER-2/neu protooncogene driven by the MMTV promoter on the $H-2^q$ FVB/N background (Guy et al, 1992) was established at the Griffith University Animal Facility and maintained under strict inbreeding conditions. The presence of the transgene was routinely confirmed by PCR. Approximately 70% of the female mice developed spontaneous mammary carcinomas with a mean latency time of 10 months. Female transgenic $FVB/N_2O_2$ rat c-neu mice bearing progressively growing tumors with a mean diameter of 10±5 mm were randomly assigned to control or treatment groups. Tumor size was measured using digital calipers. For α-TOS therapy, mice received treatment with corn oil/4% ethanol alone (control) or 10 μmoles α-TOS in corn oil/4% ethanol administered i.p. every 3 days. For 3-BP therapy, 0.2 μmoles daily of the drug was injected intratumorally. The 3-BP drug dosage used was based on a previous report (Ko et al, 2004) applying this drug to rats (average body mass ~300 g) and taking into account the lower body mass (~30 g) for mice.

Statistical analyses. The mean percentage of apoptosis, ATP and MTT reduction±SD were compared using the unpaired Student t test for between-group comparisons. The difference in the mean relative tumor size±SEM was examined using analyses of covariance (ANCOVA) with days as the covariate. Statistical analyses were performed using SPSS® 10.0 analytical software (SPSS, Chicago, USA). Differences were considered statistically significant when the value of $p<0.05$.

Example 1

3-BP, α-TOS or TRAIL Reduce Breast Cancer Cell ATP Levels

3-BP was previously reported as a highly active agent for depleting cellular ATP levels, occurring within several hours of treatment, depending on the particular dose of the drug used (Ko et al, 2004, Xu et al, 2005). In addition, the decrease in cellular ATP levels was shown to occur before the appearance of 3-BP drug-induced cancer cell death (Xu et al, 2005). The reduced ATP level correlated with the loss of pBad phosphorylation, which then allowed the pro-apoptotic Bax molecule to translocate to mitochondria, activating the apoptosis signaling pathway (Xu et al, 2005).

Therefore, the present inventors undertook a comparison of three drugs, α-TOS, 3-BP and TRAIL, for their effects on cellular ATP production in the human breast cancer MDA-MB-453 (erbB2-high) and MCF-7 (erbB2-low) cell lines. In addition, the drugs were tested on a murine breast cancer cell line, NeuTL, derived from the FVB/N rat c-neu transgenic mouse.

Figure 1:
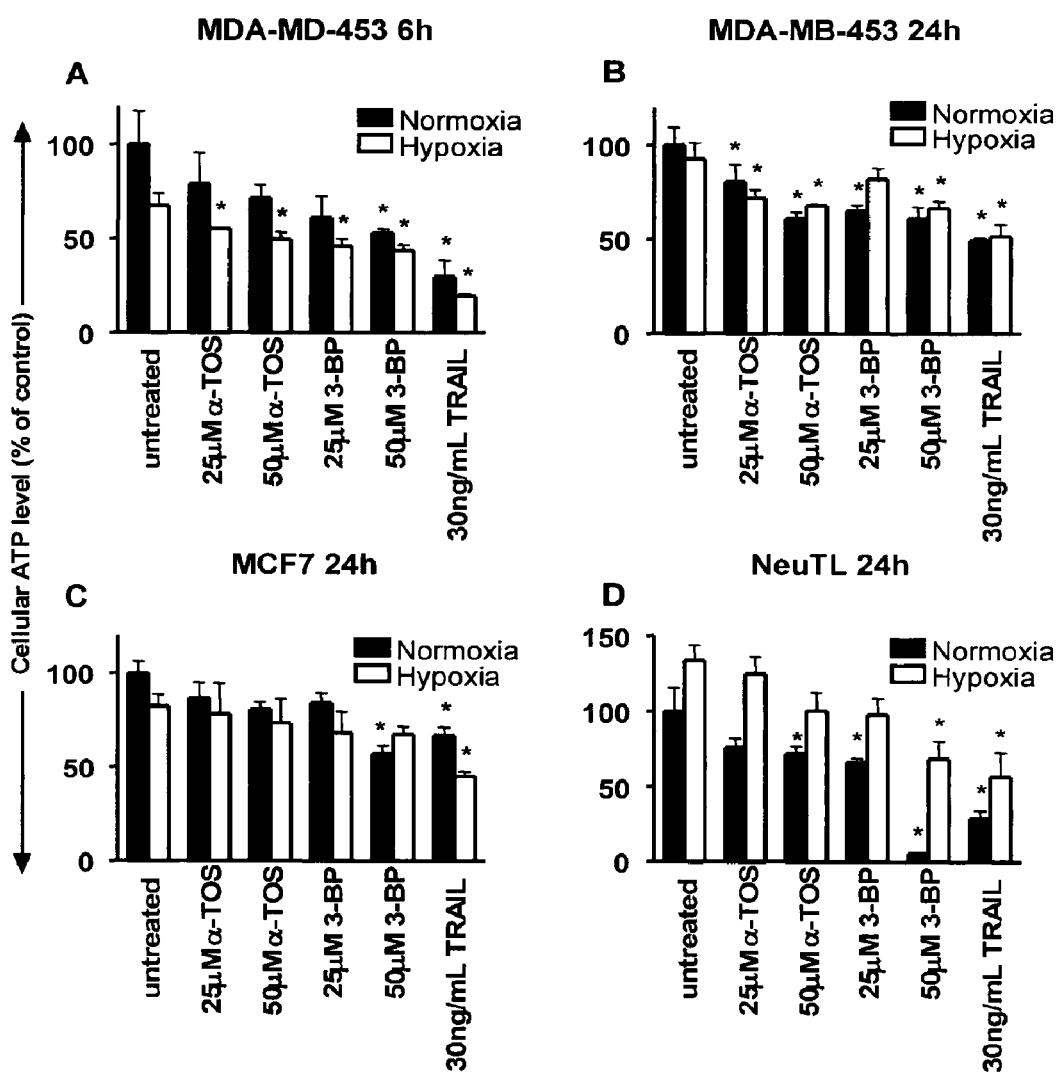
FIG. 1. α-TOS, 3-BP and TRAIL cause reduction of ATP in breast cancer cells. MDA-MB-453, MCF-7 and NeuTL breast cancer cells were treated with α-TOS, 3-BP or TRAIL at the indicated concentrations and for the time periods shown. ATP levels were then assessed using an ATP bioluminescence assay kit as described in General Materials and Methods. The data shown represent mean values±S.D. (n=5). The symbol denotes significant difference ($p<0.05$) in the level of ATP of cells compared with the untreated group.

The Results:

(FIG. 1A) reveal that within 6 h, MDA-MB-453 cells showed significantly reduced ATP levels. By 24 h, all three cell lines showed reductions in levels of ATP (FIG. 1B-D). 3-BP and TRAIL were found to be more potent inhibitors than α-TOS over the range of different concentrations tested. α-TOS only significantly reduced cellular ATP levels when applied at the higher concentration of 50 μM (FIG. 1). Cells were similarly responsive to the actions of the three drugs in depleting cellular ATP when incubated under either hypoxia or normoxia.

Example 2

Highly erbB2-positive breast cancer cells are resistant to apoptosis induced by 3-BP but not by α-TOS Breast cancer cells exhibiting high levels of erbB2 expression have an associated greater resistance to apoptosis induced by some cancer treatments (Burstein, 2005). In agreement with these findings, the present inventors have recently observed that the highly erbB2-positive MDA-MB-453 cell line was much more resistant to apoptosis induced by the death receptor activator, TRAIL, when compared to its effect on the weakly erbB2-positive MCF-7 cell line. However, MDA-MB-453 cells proved responsive to α-TOS-induced apoptosis (Wang et al, 2005). In this study, the inventors compared the two mitochondria-affecting drugs, α-TOS and 3-BP, for their relative efficacy as apoptosis inducers in the high and low erbB2-expressing breast cancer cell lines and under different conditions of $O_2$.

Figure 2:
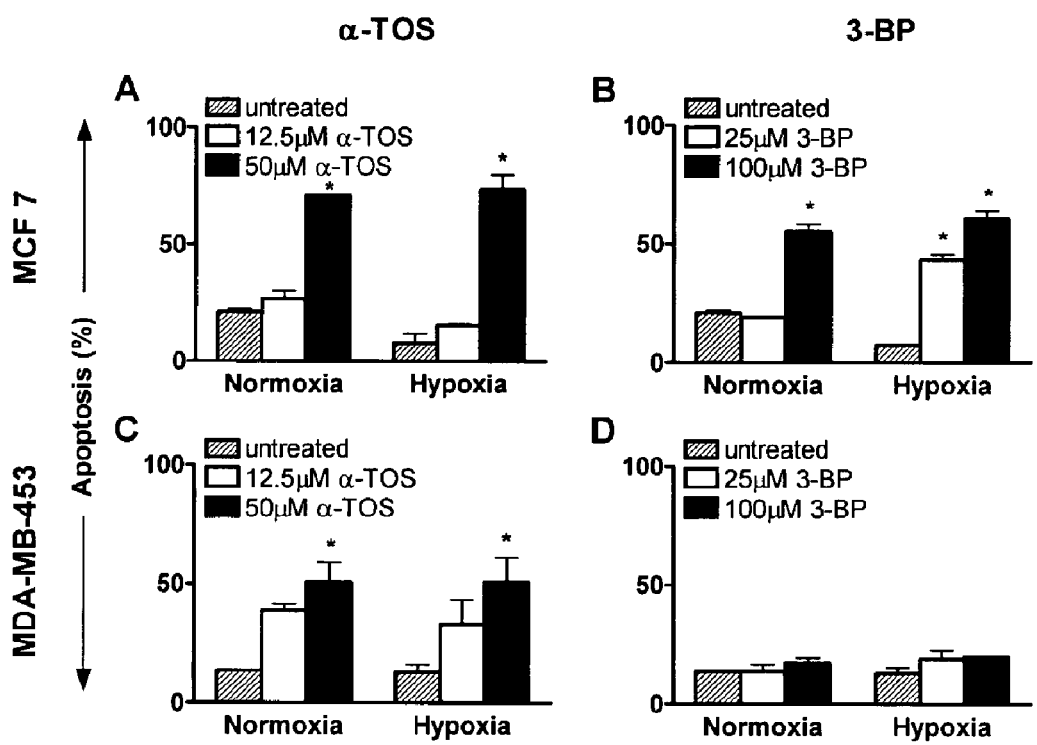
FIG. 2. Induction of apoptosis in breast cancer cell lines by α-TOS and 3-BP. MCF-7 (A, B) and MDA-MB-453 cells (C, D) were exposed to α-TOS or 3-BP at the concentrations shown for 24 h under either normoxia or hypoxia and assessed for apoptosis using the annexin V-FITC method. The data shown represent mean values±S.D. (n=3). The symbol "*" denotes significant difference ($p<0.05$) in the level of apoptosis of treated cells compared with the untreated group.

The results (FIG. 2) revealed that both the MDA-MB-453 and MCF-7 cell lines were sensitive to apoptosis induced by α-TOS under both normoxia and hypoxia. with MCF-7 cells slightly more susceptible. The MDA-MB-453 cells were found to be strikingly resistant to killing by 3-BP, even with concentrations as high as 100 μM. As for α-TOS, the responsive MCF-7 cells were found to be more sensitive to killing by 3-BP under hypoxia than normoxia (FIG. 2).

Example 3

Combination of 3-BP and α-TOS Enhances Apoptosis in Highly erbB2-Positive Cells

In this study, the present inventors determined whether α-TOS and 3-BP overlapped or whether they could enhance killing of the 3-BP-resistant MDA-MB-453 breast cancer cells. This experiment would help to provide insight into whether these drugs work via similar mechanisms or independently of one another. It was known that 3-BP acts as an inhibitor of complex II by binding to the active site of the Succinate Dehydrogenase (Sanborn et al 1971). Hence it was likely that they both might overlap each other.

Figure 3:
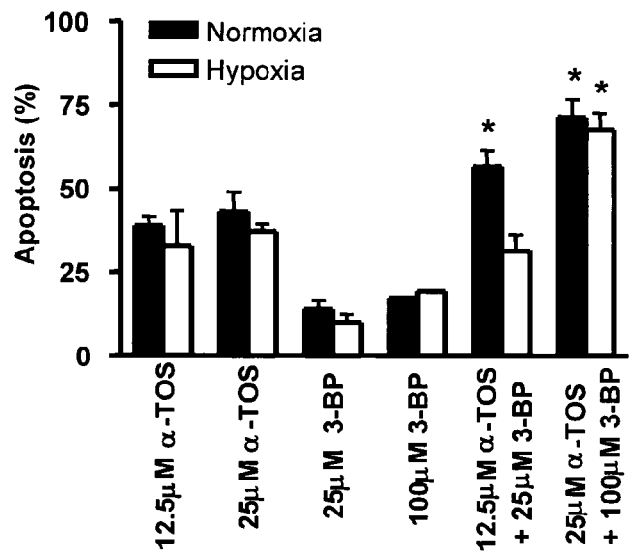
FIG. 3. Combined effects of α-TOS and 3-BP on apoptosis induction in MDA-MB-453 cells. MDA-MB-453 cells were treated for 24 h with α-TOS or 3-BP alone, or combination of α-TOS plus 3-BP at the concentrations indicated, under either normoxic or hypoxic conditions. Apoptosis was then assessed using the annexin V-FITC method. The data shown represent mean values±S.D. (n=3). The symbol denotes significant difference ($p<0.05$) in the level of apoptosis of cells treated by combination of α-TOS plus 3-BP compared with the corresponding single drug treatment.

FIG. 3 shows results of the combined effects of α-TOS and 3-BP for inducing apoptosis in MDA-MB-453 cells. Indeed, MDA-MB-453 cells were surprisingly rendered more sensitive to killing by the combination of α-TOS and 3-BP compared to either drug used alone with the extent of cancer cell apoptosis significantly enhanced ($p<0.05$) when the drug combination was used. In addition, the enhanced effects of the combination occurred regardless of whether the cell culture conditions were normoxic or hypoxic. Hence, from these results it appeared that the two different drugs were acting independently of each other and provided the unusual finding that α-TOS treatment sensitized 3-BP resistant MDA-MB-453 cells to the cytotoxic effects of 3-BP.

Example 4

Akt siRNA Restores Responsiveness of MIA-MB-453 Cells to 3-BP and Increases Sensitivity to α-TOS and TRAIL Previous studies have shown that high levels of erbB2 expression resulted in activation of Akt, which phosphorylates many different cellular targets, including Bad (Zhao et al, 2004) and caspase-9 (Cardone et al, 1998). In this manner, cancer cells exhibit increased survival and become resistant to apoptosis induced by drug treatment (West et al, 2002, Osaki et al, 2004, Fresno et al, 2004, Grandage et al, 2005). In fact, inhibiting cellular expression of Akt using the antisense RNA approach has been proposed as a general method for restoring sensitivity of cancer cells to drug therapy (Kim et al, 2004). In addition, siRNA against Akt has been used recently in several studies examining the effects of down-regulating Akt expression in cancer cells on their survival (Takeuchi et al, 2005, Yoeli-Lerner et al, 2005). Hence, the present inventors have made use of RNAi technology as a means for reducing Akt1 expression to determine whether this would render the erbB2-positive 3-BP- and TRAIL-resistant MDA-MB-453 cells responsive to the two agents and whether this would also make them more sensitive to α-TOS-mediated apoptosis.

Transfection of MDA-MB-453 cells with siRNAs was performed using OligofectAmine and OptiMEM. Briefly, cells were allowed to reach ~50% confluency and supplemented with 60 pmol/l siRNA pre-incubated with OligofectAmine and overlayed with OptiMEM. Cells were washed 24 h later with PBS, overlaid with complete DMEM, cultured for an additional 24 h, 48 h and transgene expression confirmed using Western blotting before they were used for further experiments.

Figure 4:
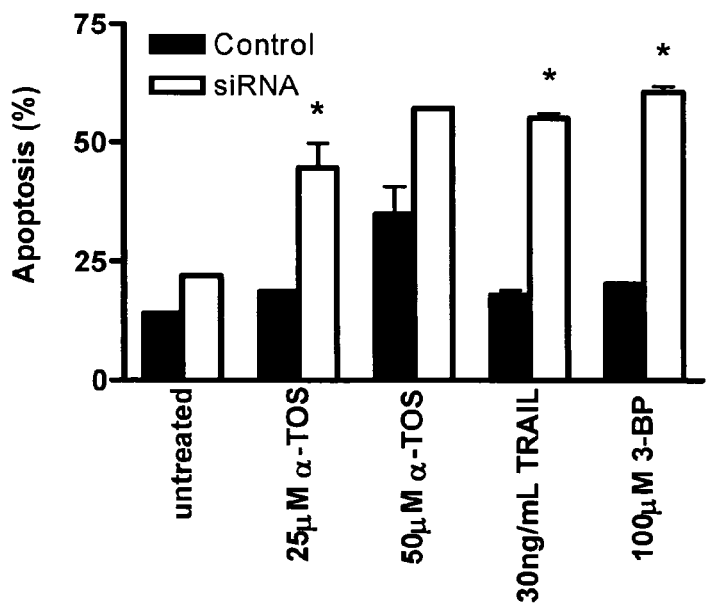
FIG. 4. Akt1 knock-down sensitizes MDA-MB-453 cells to α-TOS, 3-BP and TRAIL. MDA-MB-453 cells at 50% confluency were pre-treated with 60 pM Akt1 siRNA for 24 h before treatment with α-TOS, TRAIL or 3-BP at the concentrations shown for a further 24 h. Apoptosis was assessed using the annexin V-FITC method. Two independent experiments were conducted. Results are represented as mean±S.D.

The results (FIG. 4) revealed that pre-treatment of MDA-MB-453 cells with Akt1 siRNA was effective in sensitizing them to each of the three drugs tested, producing a particularly marked increase in cytotoxic responsiveness to 3-BP. This evidence suggests that breast cancers with high levels of Akt activity are predisposed to resistance to 3-BP treatment and this can be efficiently modulated by molecular manipulation.

The effect of Akt siRNA on cellular responsiveness to 3-BP and the increased apoptosis with the combined α-TOS/3-BP treatment raises the possibility that α-TOS may also affect Akt activity, thereby providing a similar increase in sensitivity of cancer cells to 3-BP as did Akt siRNA.

Example 5

α-TOS Targets the UbQ-Binding Pockets on Complex II

Previous studies by the present inventors (reviewed in Neuzil et al, 2004) showed that mitochondria were central to the mechanism of action of α-TOS in cancer cells and resulted in the activation of the mitochondrial apoptosis-signaling pathway. α-TOS has held an 'orphan drug' status until recently with the discovery of its Bcl-2/Bcl-$x_L$ inhibitory activity (Shiau et al, 2006). However, the specific mitochondrial target for this drug leading to ROS production as early as 1 h after addition of α-TOS to cancer cells and the ensuing initiation of the pro-apoptotic pathway (Weber et al, 2002, Stapelberg et al, 2005) has not been well defined (Zhang et al, 2001).

To this end, the present inventors investigated whether α-TOS interferes with UbQ binding in complex II. For specifically measuring complex II activity in whole cells, a short-term (1-2 h) assay was used based on the reduction of the tetrazolium salt, MTT (Maehara et al, 1988). Hence, special conditions were used ensuring that mitochondrial respiration was optimally proceeding in whole cells via complex II. For this, oxidative respiration of murine NeuTL breast cancer cells was sustained on high levels of succinate (20 mM), thereby promoting the SDH activity of complex II (Maehara et al, 1988). The cells were then assayed within 1-2 h for their ability to enzymatically reduce MTT, which under conditions of high succinate becomes a specific indicator of complex II/SDH-dependent activity (Maehara et al, 1988, Berridge and Tan, 1993).

Previous studies have shown that 3-BP (Sanborn et al, 1971) and 3NPA (Scallet et al, 2003) both acted as potent inhibitors of the SDH activity, with 3NPA having recently been shown to be a specific suicide inhibitor of SDH (Huang et al, 2006), capable of inhibiting MTT reduction relatively quickly within 4 h of addition to cells (Scallet et al, 2003). Initial experiments were carried out with the two SDH inhibitors, 3-BP and 3NPA, in the absence of added succinate that would otherwise compete with these inhibitors, in order to determine whether they directly inhibit MTT reduction in the NeuTL cells. The results (FIG. 5A) confirmed that 3-BP and 3NPA were both potent inhibitors of the complex II-mediated MTT reduction and that the assay was therefore suitable for our purposes to quantify effects of drugs on SDH activity.

Figure 5:
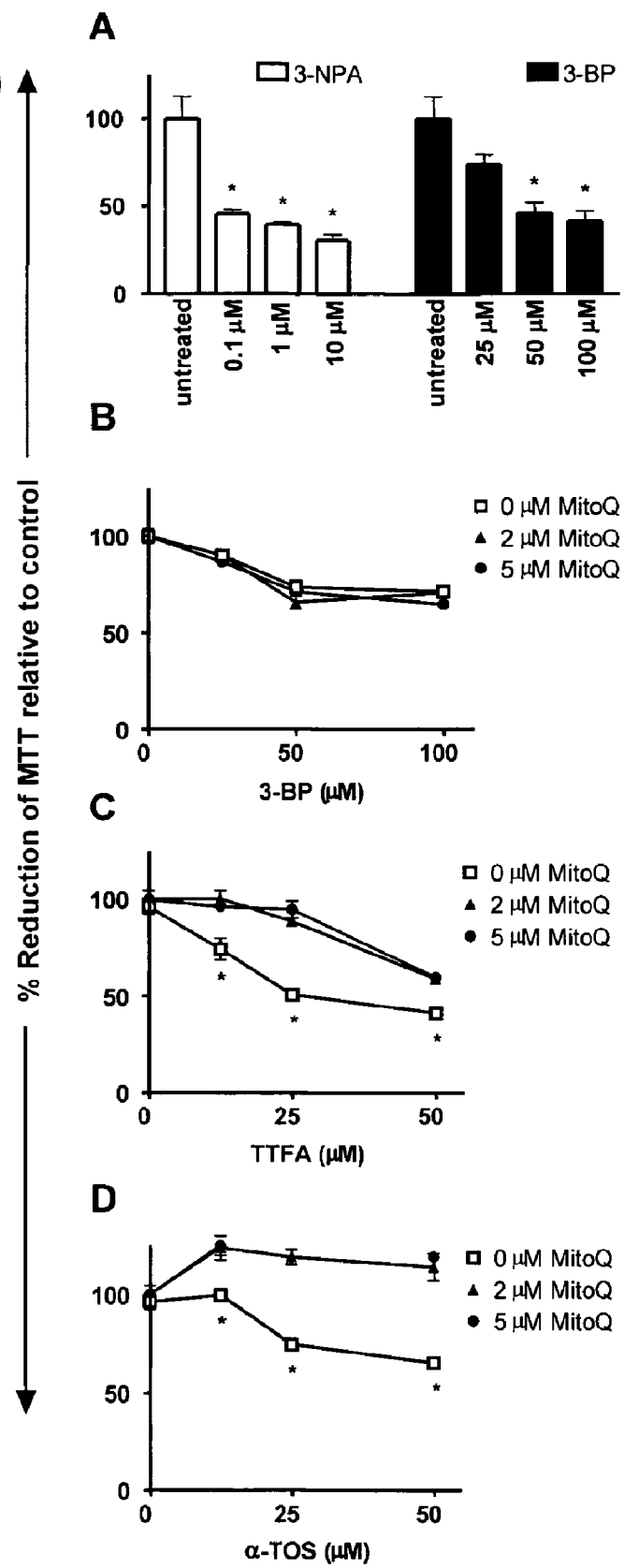
FIG. 5. The effect of 3NPA, BP, TTFA and α-TOS on the ability of NeuTL cells to reduce MTT. (A) MTT reduction in PBS was assessed after a 4 h co-incubation period in the presence of 3NPA or 3-BP used at the concentrations shown. (B) Cells were pre-incubated for 60 min with MitoQ before addition of 3-BP at the concentrations shown and assessed for their ability to reduce MTT in PBS after a 2 h incubation period. (C) In the presence of TTFA or (D) α-TOS at the indicated concentration, cells pre-incubated for 60 min with MitoQ were assessed for their ability to reduce MTT in RPMI containing 20 mM succinic acid (pH 7.4) after a 2 h incubation period. Results are presented as mean % reduction of MTT relative to control (untreated) ±S.D. The symbol denotes significant difference ($p<0.05$).

Thenoyltrifluoroacetone (TTFA) has been established as a specific inhibitor that targets the UbQ-binding sites involved in the electron transfer flow of complex II (Berridge and Tan, 1993, Sun et al, 2005). These sites lie beneath the SDH reaction centre, in the trans-membrane region of complex II, ready to transfer electrons to UbQ in order to relay them on to complex III. Interestingly, TTFA is toxic to all cells (Zhang et al, 2001b). As with the SDH enzyme inhibitors 3-BP and 3NPA, TTFA also significantly inhibited the enzymatic reduction of MTT by the breast cancer cells within a few hours (FIG. 5C). In fact, treatment with either of 3-BP, α-TOS or TTFA revealed dose-dependent changes as early as a few hours after treatment with significant decreases occurring in the levels of MTT reduction by these cells (FIG. 5B-D). However, pre-incubating the cells for 1 h with MitoQ. a mitochondrially targeted form of UbQ (Kelso et al, 2001, James et al, 2005), revealed that MitoQ was able to overcome the inhibition in MTT reduction caused by either TTFA (FIG. 5C) or α-TOS (FIG. 5D), but not by 3-BP (FIG. 5B). The rationale here was that if any of these drugs were acting by binding to the UbQ site of complex II, then loading cells with increased levels of the UbQ-active analogue, MitoQ, would reduce the extent of drug-mediated inhibition of MTT reduction by complex II. The inhibitory effect of 3-BP on the MTT reduction was not significantly different when the cells were treated in the presence or absence of different concentrations of MitoQ (FIG. 5B), in agreement with 3-BP acting by inhibiting the SDH head group and not via the downstream trans-membrane UbQ site of complex II. However, the inhibition caused by addition of TTFA (FIG. 5C) and α-TOS (FIG. 5D) was significantly overcome by pre-incubation of the cells with MitoQ. In particular, α-TOS was much less effective at inhibiting succinate-driven MTT reduction in the presence of MitoQ, which has also recently been shown to be specific for binding to complex II of the mitochondrial redox chain (James et al, 2005).

Example 6

Figure 6:
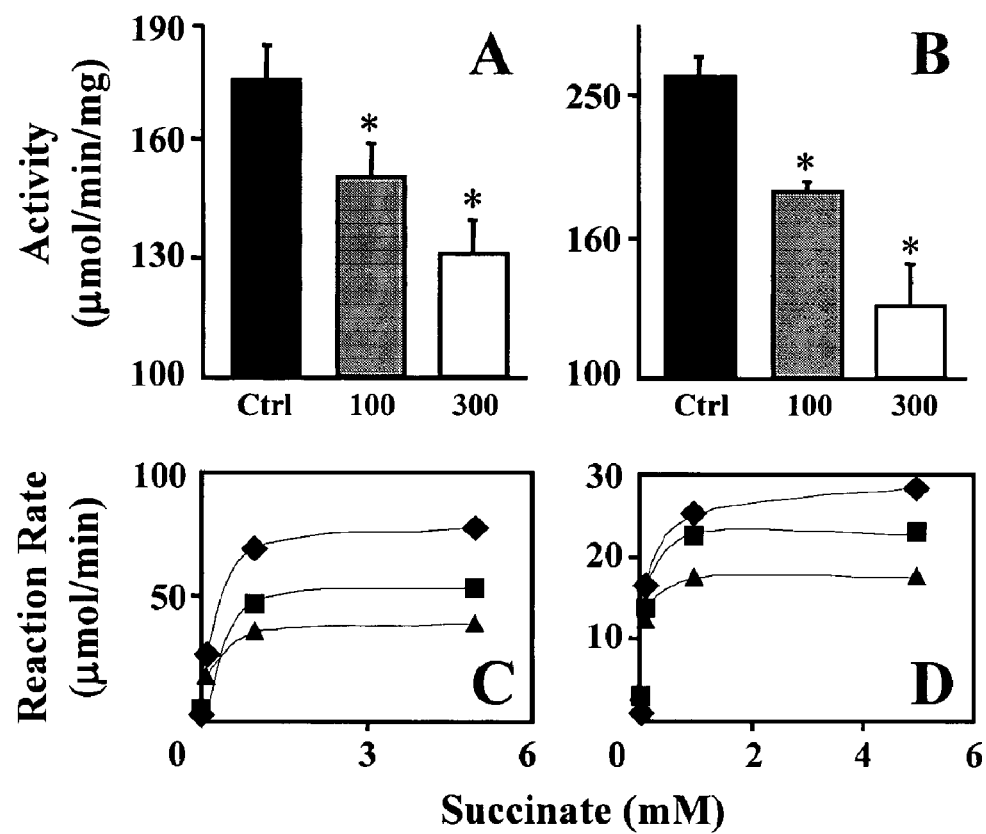
FIG. 6. Inhibition of SDH/Complex II activity in isolated rat liver mitochondria (A, C) or Paracoccus denitrificans (B, D) by α-TOS. Cells were fractionated as outlined in General Materials and Methods and preparations of mitochondria from rat liver or membranes from P. denitrificans were incubated in a reaction volume facilitating mitochondrial SDH/Complex II activity and containing the indicator dye DCIP PMS. Samples in A and B contained succinate and were either treated with 100 or 300 μM α-TOS as indicated. Control reactions received the equivalent addition of the diluent DMSO alone. Absorbance at 600 nm wavelength was measured and presented as changes in enzyme activity (μmol/min/ml). Results in the bar graphs A and B are represented as mean values±S.D. (n=3). The symbol '*' indicates values significantly different from the controls with $p<0.05$. Panels C and D display changes in the reaction rate (μmol/min) measured under different concentrations of succinate as indicated in the absence or presence of 100 or 300 μM α-TOS.

Validation that α-TOS Inhibits Mitochondrial Respiratory Complex II Activity Additional support for the role of α-TOS in inhibiting mitochondrial respiratory complex II activity was sought by isolating subcellular fractions containing mitochondrial preparations from rat liver as well as membranous fractions from P. denitrificans. For these studies, the assay method of SDH/Complex II activity was based on that of King (1967) using phenazine methosulphate (PMS) and the terminal electron acceptor, 2,6-dichloroindophenol (DCIP) as the indicator dye by following the decrease in absorbance at 600 nm as it was reduced by SDH driven under conditions of high succinate. The results (FIGS. 6A,B) revealed that with both the rat liver mitochondrial and the Paracoccus membrane preparations, the rates of reduction of DCIP compared to control samples decreased rapidly and significantly after treatment with α-TOS. Hence, the results strongly support α-TOS acting directly on the UbQ sites of complex II, interfering with the electron flow to PMS and DCIP. The selectivity of α-TOS for the SDH activity is supported by the result showing no effect of the vitamin E analogue on the NADH dehydrogenase (complex I) activity (data not shown).

Example 7

Figure 7:
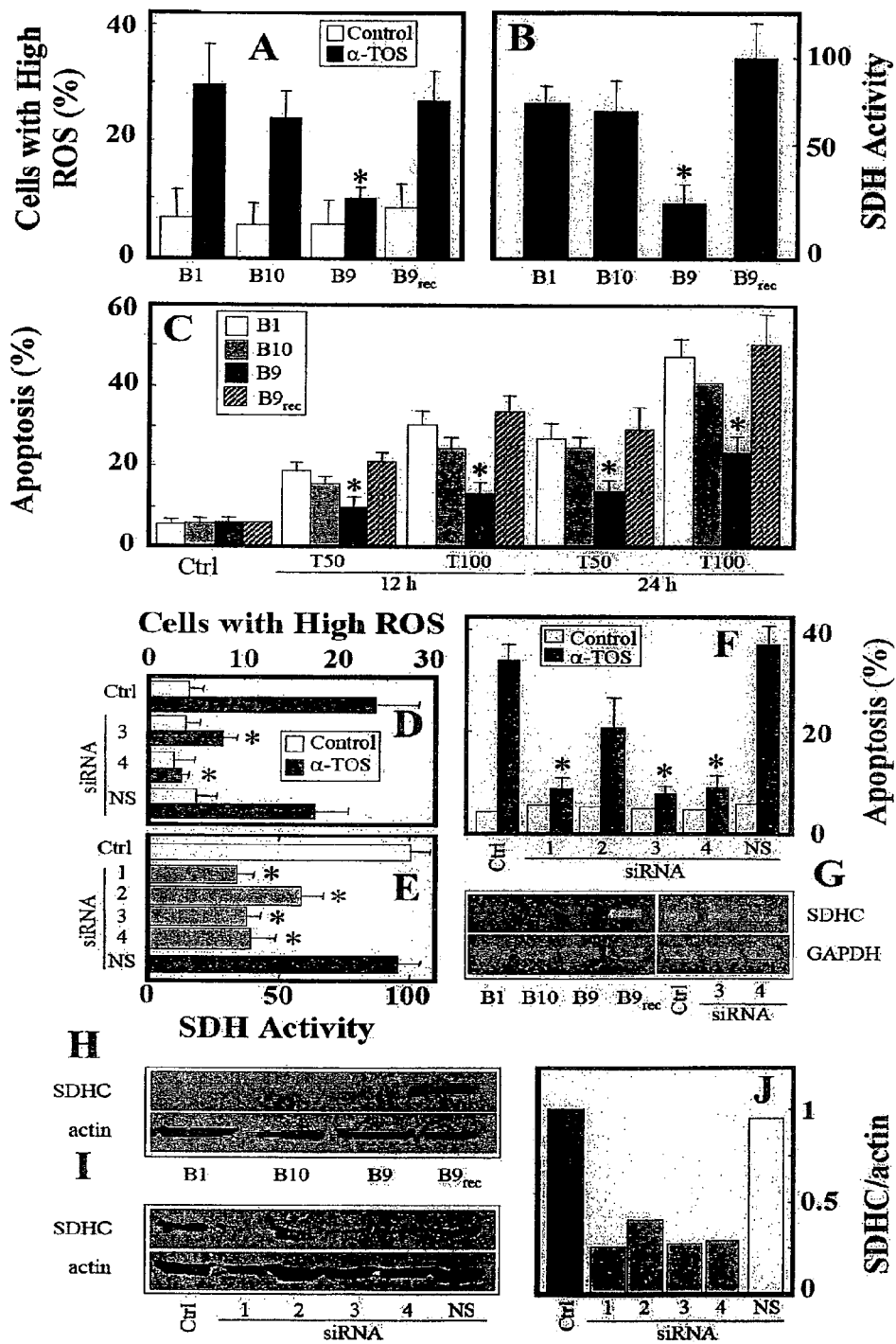
FIG. 7. Apoptosis induction by α-TOS is suppressed in CII dysfunctional cells. Parental (B1), CI-dysfunctional (B10), CII-dysfunctional (CybL-mutant; B9), and CybL-mutant cells following complex II reconstitution by transfection with human CybL (B9$_{rec}$) were exposed to α-TOS at concentrations and for times shown, harvested and assessed for ROS accumulation (A), SDH activity assessed in whole cells on the basis of MTT reduction with succinate as a substrate (B), and apoptosis (C). MCF7 cells were pre-treated with CybL or non-specific (NS) siRNA, exposed to α-TOS as shown, and assessed for ROS accumulation (D), SDH activity (E), and apoptosis induction (F). Panels G shows results of RT-PCR analysis of B1, B10, B9 or B9rec cells as well as SDHC siRNA-treated MCF cells using human SDHC primers. Panel H reveals results of Western blotting of B1, B10, B9 and B9$_{rec}$ cells using human monoclonal anti-SDHC IgG. Western blotting is also shown to document the levels of SDHC in MCF7 cells treated with different SDHC siRNA duplexes and with NS siRNA (I), which was evaluated relative to the actin band (J). Results are represented as mean values±S.D. (n=3), images are representative of three independent experiments. The symbol '*' indicates values significantly different from the controls with $p<0.05$.

Validation that α-TOS Inhibits Mitochondrial Respiratory Complex II Activity Using Complex I- and Complex II-Deficient Cells Complex I- and complex II-deficient cells were also used to confirm the above in vitro results of Example 6. CI-dysfunctional (B10 cells) (Seo, B. B. et al, 1998), CII-dysfunctional (B9 cells with mutant cytochrome b large, CybL), and the parental Chinese hamster lung fibroblasts (B1 cells) (Oostveen, F. G. et al, 1995) were grown in DMEM with 10% FCS, antibiotics, 10 mg/ml glucose and non-essential amino acids. α-TOS initiated apoptosis in parental Chinese hamster lung fibroblasts (B1 cells), CI dysfunctional cells (BIO cells) and CII-dysfunctional cells (B9 cells, with a mutation in the gene encoding the SDHC subunit, CybL). B9 cells were less responsive to α-TOS, with lower levels of ROS accumulation (FIG. 7A) and diminished SDH activity (FIG. 7B) compared to the parental (B1) or B10 cells. In line with these findings, B9 cells were relatively resistant to apoptosis induced by the VE analogue (FIG. 7C). Reconstitution of CII in CybL-mutant (B9) cells normalized the SDH activity (FIG. 7B), and also restored cell sensitivity to α-TOS-induced killing (FIG. 7C).

Data obtained with the CII-dysfunctional (B9) and the reconstituted B9 cells were independently verified by treatment of MCF7 cells with four different short-interfering RNAs (siRNA) against CybL. Duplexes 1, 3 and 4 substantially suppressed CII activity (FIG. 7D). Mutation in CybL inhibited ROS accumulation and SDH activity, and reduced the levels of apoptosis mediated by α-TOS (FIGS. 7D-F).

Using a human monoclonal SDHC antibody, B), B9 and B10, and the CII-reconstituted Chinese hamster lung fibroblasts (B9$_{rec}$) were probed for the presence of SDHC. Western blotting analysis (FIG. 7H, I) revealed the absence of human SDI-IC in the B1, B9 and B10 cells, and its low level in MCF-7 cells treated with the SDHC siRNAs. The B9 cells with reconstituted CII revealed re-appearance of SDHC. As revealed by densitometric evaluation, siRNA treatment of MCF7 cells lowered the level of the SDHC protein by 50-80% (FIG. 7J). These data are consistent with RT-PCR results showing presence of human SDHC mRNA in CII-reconstituted cells and low levels of the transcript in MCF7 cells treated with SDHC siRNA (FIG. 7G). The siRNA approach was specific for SDHC, since any changes in the level of the SDHB subunit protein in the SDHC-treated MCF7 cells were not observed (data not shown).

Example 8

Molecular Modeling Reveals Stronger Binding of α-TOS to the Complex II Active Site than for UbQ Itself To help rationalize the results above indicating that α-TOS interacts with mitochondrial complex II via the UbQ binding site/s, the present inventors undertook a molecular modelling study of this system using AutoDock (Morris et al., 1998). The crystal structure of porcine heart mitochondrial complex II has been reported recently (Sun et al, 2005), and because of its high sequence identity with human mitochondrial complex II the present inventors decided to use this structure (1ZOY) as the basis for their AutoDock study. The structure shows clearly the proximal UbQ binding site ($Q_P$) and the related structure (1ZP0) with the inhibitor TTFA bound suggests the position of the proposed distal UbQ binding site ($Q_D$).

To test the feasibility of using AutoDock to study this system they first used it to dock UbQ5 to both the $Q_P$ and the proposed $Q_D$ binding sites. UbQ5 was chosen as it was a similar size to α-TOS (FIG. 8) and also contains a similar number of rotatable bonds (16 and 17 respectively). UbQ5 docked in $Q_P$, to a slightly deeper position than that observed for the portion of UbQ resolved in the crystal structure published by Sun et al (2005). Interestingly, this deeper docking position was observed in a recent study where the docking program GOLD was used to dock UbQ2 to the crystal structure of complex II from E. coli (Horsefield et al, 2006). UbQ5 was also found to dock into the proposed $Q_D$ site, with the UbQ ring sitting in front of the binding site and the hydrophobic tail located inside the site. The interaction energies calculated by AutoDock (FIG. 8) suggest that UbQ5 interacts with the $Q_P$ site to a greater degree than with the proposed $Q_D$ site. This correlated well with the fact that no UbQ binding was observed in the proposed $Q_D$ site and suggested that the $Q_P$ site provides the strongest interaction with UbQ5.

Figure 8A:
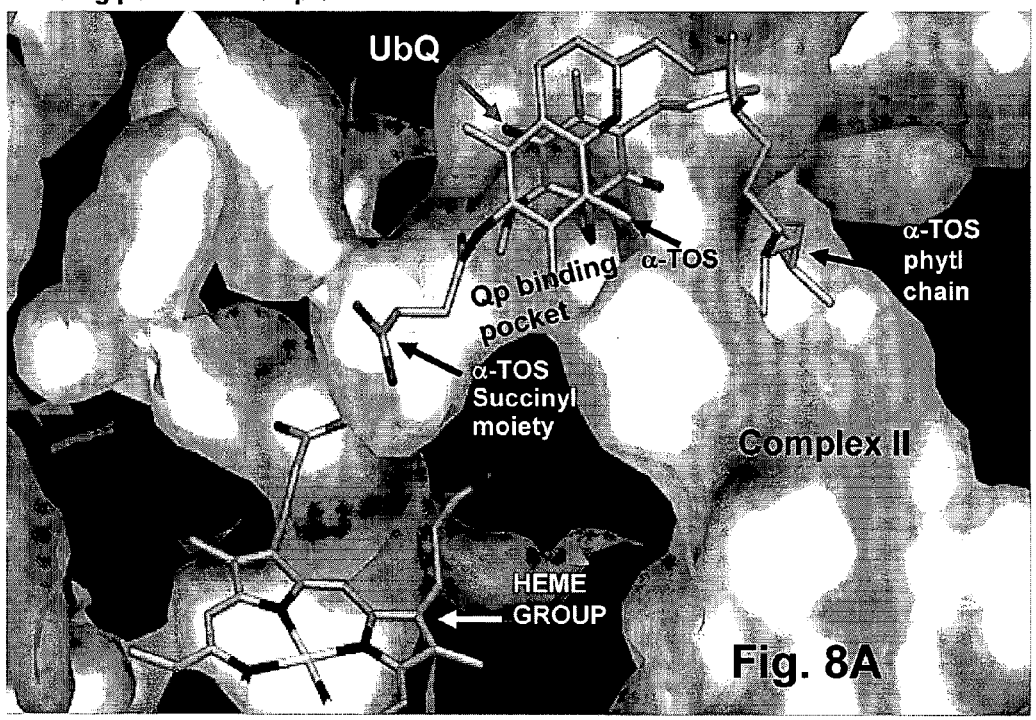
FIG. 8. Molecular modeling (A) The best ranked docking pose of a UbQ molecule compared to the α-TOS structure bound to the $Q_P$ binding site in the complex II crystal structure. The image is presented as a cut-away cross section/relief of complex II in space filling mode with the bound drugs presented as stick figures. The various components are labeled for identification. (B) The best ranked docking pose of α-TOS to the $Q_P$ binding site compared with the related UbQ structure for this site extracted from the complex II crystal structure in stick figure format. The important amino acid residues of complex II involved in binding are identified and coded according to their subunit chain and residue number for each. α-TOS structure is highlighted and labeled as the darker stick figure. (C) Stereo images derived from (B) providing 3-dimensional visualization of the spatial distribution of important amino acid residues and their side groups involved in the interaction of the Complex II $Q_P$ binding pocket with alpha-TOS. Surprisingly it can be seen that alpha-TOS penetrates much deeper into the pocket than the UbQ molecule and co-ordinates linkage to Serine 42 of the SDHC (CybL) subunit providing hydrogen bonding. (D) A Ligplot diagram showing the major interactions between the best docked conformation of α-TOS and the $Q_P$ binding site amino acid residues important for binding. (E) The best ranked docking pose of α-TOS to the $Q_D$ binding site; Binding of α-TOS compared to UbQ wrapped around inside the pocket, showing a bridge (in translucent format) formed by part of Complex II extending across the front of the pocket.
Figure 8D:
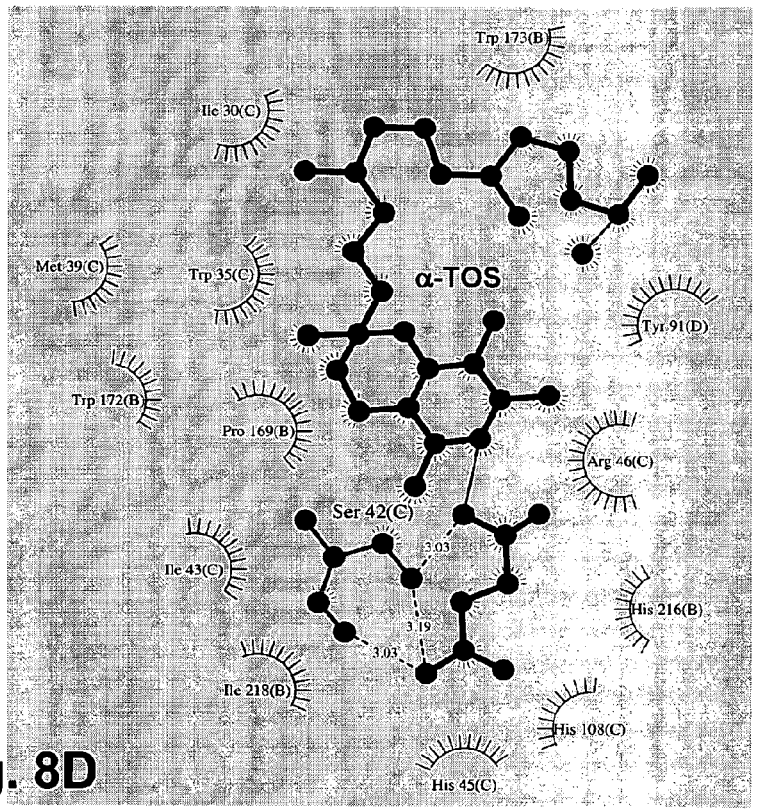
Figure 8E:
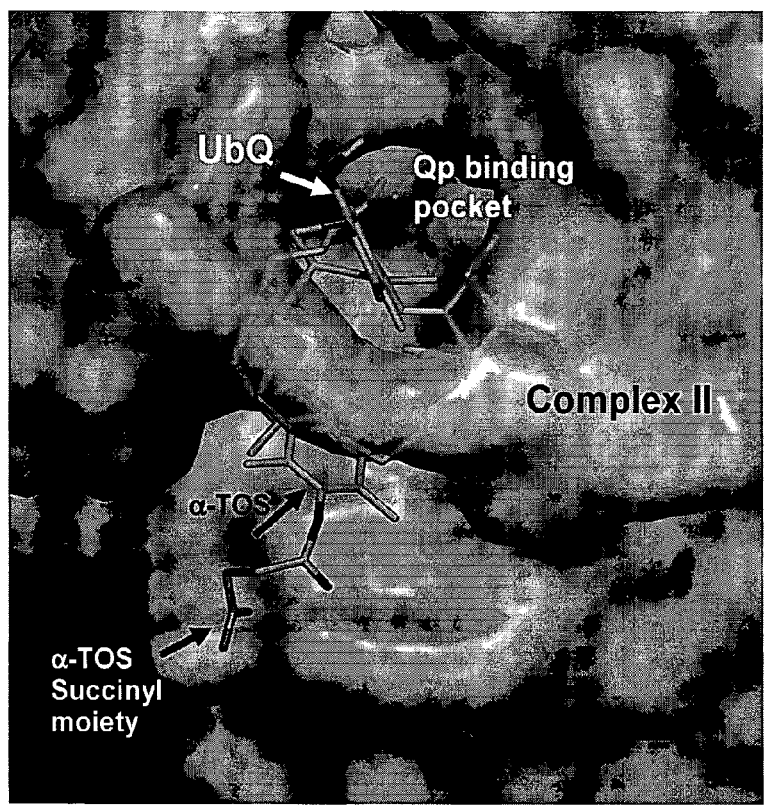
Figure 8F:
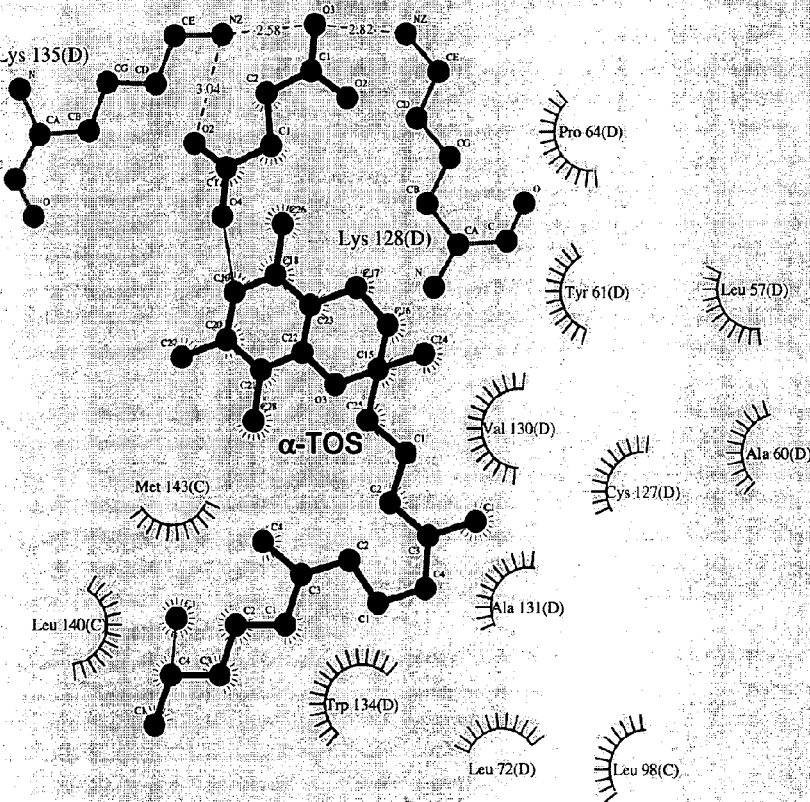

AutoDock revealed α-TOS binding in both the $Q_P$ and $Q_D$ site as seen in FIGS. 8A-D. In the $Q_P$ site the ring system of α-TOS sits in the same binding pocket as the UbQ ring but is tilted away to the other side. Surprisingly, the succinate ester moiety was found to extend deeper down into the binding pocket and extends down towards the location of the prosthetic heme group. The carboxyl group fits neatly into this pocket and is involved in a bidentate hydrogen bond with Ser42(C) (FIG. 8B,C,D). Ser42(C) also interacts with the ester oxygen of α-TOS. As befits the hydrophobic nature of the rest of the α-TOS molecule all the other interactions with the protein are hydrophobic. The hydrocarbon side chain loops around and extends out of the $Q_P$ site and along the same channel where the isoprenoid side chain of UbQ5 was shown to dock. In the $Q_D$ site the ring system of α-TOS sits towards the bottom of the binding site with the succinate ester moiety extending out the bottom of the site in a similar way to that observed for the head group of the phospholipid visible in the crystal structure. The succinate moiety is seen to hydrogen bond to Lys135(D) and Lys128(D) (FIG. 8E) while the hydrocarbon side chain loops around the inside of the binding site.

The calculated energy of interaction for the docked conformations of α-TOS (FIG. 8F) suggested that it can bind at either $Q_P$ or $Q_D$ sites, but there is a preference for binding at the $Q_D$ site. While the binding energy of α-TOS at the $Q_P$ site is slightly less than UbQ5, α-TOS would certainly be able to compete with UbQ5. At the $Q_D$ site α-TOS shows a much better binding energy than UbQ5 and should be able to displace it from this binding site.

Collectively, these findings indicate that α-TOS interferes with ubiquinone (UbQ) binding and blocks reduction of UbQ by the membrane domain of complex II in the respiratory chain. As a result, electrons are no longer transferred down the succinate dehydrogenase hydrophilic head on to FAD and relayed via the [4Fe-4S] to UbQ, but instead leak into the mitochondria, producing increased levels of ROS that ultimately induces apoptosis of the cancer cell.

Autodocking of the vitamin E analogues shown below in Tables 4 and 5 was performed using the same protocol as described above and the predicted interaction energies are presented in the last column of each table.

TABLE 4

Interaction energy of vitamin E analogues at proximal coenzyme Q-binding site ($Q_p$). Compounds are sorted by the Signaling Domain.

| Nr. | Functional Domain I (R1) | Signalling Domain II | Hydrophobic Domain III (R2) | Interaction energy at $Q_p$ (kcal/mol) |
|---|---|---|---|---|
| 1 | $^-O_2CCH_2CH_2COO-$ | (chromanol structure with R1, H₃C, CH₃, CH₃, R2, O) | (isoprenoid side chain, n=3) | −15.04 |
| 2 | $CH_3COO-$ | | | −14.7 |
| 3 | $^-O_2CCH=CHCOO-$ | | | −13.71/−14.55[a] |
| 4 | $^-O_2CCH_2CH(CH_3)COO-$ | | | −13.57/−14.1[b] |
| 5 | $^-O_2CCH_2(CH_2)_2COO-$ | | | −14.64 |
| 6 | $^-O_2CCH_2CH(CH_3)CH_2COO-$ | | | −13.86/−14.84[b] |
| 7 | $^-O_2CCH_2C(CH_3)CH_2COO-$ | | | −13.39 |
| 8 | $^-O_2CC(CH_3)_2CH_2CH_2COO-$ | | | −13.34 |
| 9 | $H_3COOCCH_2CH_2COO-$ | | | −14.76 |
| 10 | $^-O_2CCOO-$ | | | −13.63 |
| 11 | $^-O_2CCH_2COO-$ | | | −13.91 |
| 12 | $^-O_2CCH_2CH_2CONH-$ | | | −14.38 |
| 13 | $^-O_2CCH=CHCONH-$ | | | −14.09/−14.34[a] |
| 14 | $H_3COOCCH_2CH_2CONH-$ | | | −14.73 |
| 15 | $^+NH_3-CH_2COO-$ | | | −14.96 |
| 16 | $^+NH_3Lys(NH_3)COO-$ | | | −13.89 |
| 17 | $Lys-Lys(Lys)COO-$ | | | −15.27 |
| 18 | $CH_3O-$ | | | −11.89 |
| 19 | $CH_3CH_2COO-$ | | | −13.11 |
| 20 | $^-O_2CCH_2CH_2CH_2O-$ | | | −13.93 |
| 21 | $^-O_2CCH_2O-$ | | | −12.56 |
| 22 | $^-O_2CCH_2-$ | | | −14.23 |
| 23 | $(PEG)O_2CCH_2CH_2COO-$ | | | |
| 24 | $^-O_2C(CH_2)_5COO-$ | | | −14.5 |
| 25 | $C_2H_5OOCCH_2CH_2COO-$ | | | −13.93 |
| 26 | nicotinic acid | | | |
| 27 | $^-O_2CCH_2CH(SePh)COO-$ | | | |
| 28 | all-trans retinoic acid | | | |
| 29 | 9-cis retinoic acid | | | |
| 30 | $HOPO_2O-$ | | | |
| 31 | $Toc-OPO_2O-$ | | | |
| 32 | $^-O_2CCH_2CH_2COO-$ | (chromanol structure with R1, CH₃, CH₃, R2, O, CH₃) | | −14.58 |

TABLE 4-continued

Interaction energy of vitamin E analogues at proximal coenzyme Q-binding site ($Q_p$). Compounds are sorted by the Signaling Domain.

| Nr. | Functional Domain I (R1) | Signalling Domain II | Hydrophobic Domain III (R2) | Interaction energy at $Q_p$ (kcal/mol) |
|---|---|---|---|---|
| 33 | $^-O_2CCH_2CH_2COO-$ | chroman with R1 at 6-position, H$_3$C at 7, CH$_3$ at 8, R2 and CH$_3$ at 2 | | −14.68 |
| 34 | $^-O_2CCH_2CH(SePh)COO-$ | | | |
| 35 | $^-O_2CCH_2CH_2COO-$ | chroman with R1 at 6-position, CH$_3$ at 8, R2 and CH$_3$ at 2 | | −14.64 |
| 36 | $^-O_2CCH=CHCOO-$ | | | −14.46/−15.08[a] |
| 37 | $^-O_2CCH_2CH_2CONH-$ | | | −14.71 |
| 38 | $^-O_2CCH=CHCONH-$ | | | −14.67/−15.01[a] |
| 39 | $H_3COOCCH_2CH_2COO-$ | | | −14.53 |
| 40 | HO— | | | −12.33 |

[a] The first value is for the cis- and the second for the trans-configuration.
[b] The two values refer to the two enantiomers tat the chiral carbon.

TABLE 5

Interaction energy of vitamin E analogues at proximal coenzyme Q-binding site ($Q_p$) with a modified Hydrophobic Domain.

| Nr. | Functional Domain I (R1) | Signalling Domain II | Hydrophobic Domain III (R2) | Interaction energy at $Q_p$ (kcal/mol) |
|---|---|---|---|---|
| 41 | $^-O_2CCH_2CH_2COO-$ | chroman with R1 at 6, H$_3$C at 7, CH$_3$ at 8, R2 and CH$_3$ at 2 | COO$^-$ | −11.13 |
| 42 | HO— | | isoprenoid chain (n=2) | −11.63 |
| 43 | $^-O_2CCH_2CH_2COO-$ | | | −13.67 |
| 44 | $^-O_2CCH_2CH_2O-$ | | | −12.89 |
| 45 | $^-O_2CCH_2CH_2COO-$ | | isoprenoid chain (n=1) | −12.28 |
| 46 | | | CH$_3$ | −10.97 |
| 47 | $^+NH_3Lys(NH_3)COO-$ | | CH$_2$—OH | −12.24 |
| 48 | | | CH$_2$—O-nC$_5$H$_{11}$ | −12.29 |
| 49 | | | CH$_2$—OC(O)nC$_4$H$_9$ | −12.75 |
| 50 | | | CH$_2$—O-cholic acid | |
| 51 | HO— | | CH$_2$CH$_2$COO$^-$ | −8.66 |

TABLE 5-continued

Interaction energy of vitamin E analogues at proximal coenzyme Q-binding site ($Q_p$) with a modified Hydrophobic Domain.

| Functional Nr. | Domain I (R1) | Signalling Domain II | Hydrophobic Domain III (R2) | Interaction energy at $Q_p$ (kcal/mol) |
|---|---|---|---|---|
| 52 | HO— | R1, H3C, CH3, O, CH3, R2 (chromanol structure) | $CH_2CH_2COO^-$ | −8.48 |

The above vitamin E analogues where docked to the crystal structure of porcine complex II (proximal ubiquinone binding site) using AutoDock 3.0.5 and the same protocol as has been described earlier. By comparing the predicted energy of interaction and the number of conformations generated, the following observations are made regarding changes to the α-TOS template that are important in binding:

1. Terminal charge. The α-TOS template has a negative charge due to its terminal carboxylic acid, abolition of this charge decreased the interaction energy while replacing it with a positive charge maintained a similar interaction energy. The area where this charged group docks is surrounded by polar amino acid residues (Histidine and Serine) but no charged residues. The closest charge comes from the carboxy group of the nearby Heme group. This allows the accommodation of either positive or negative charged groups.

2. Ester linkage. The ester linkage joining the succinate moiety to the original Vitamin E backbone can be replaced by an amide linkage with little change in interaction energy.

3. The succinate moiety can be replaced by a fumarate moiety (as long as the configuration at the double bond is maintained as trans) and still retain a good interaction energy.

4. The methyl groups on the aromatic ring of α-TOS are important for positioning the entity within the proximal unbiquinone binding site. Removal of them reduces the energy of interaction.

In FIG. 9, the inventors analysed the correlation between the binding affinities of the vitamin E analogues for the ubiquinone site and their biological activity in causing apoptosis of cancer cells. The result indicates a direct relationship between the binding affinity to the site and their ability to kill cancer cells. The differences observed between the docking and the list of results reflects the biological accessibility of the compounds reaching the complex II target site. Thus, the IC50 reflects not only the ability of the analogues to bind to the site, but also their ability to enter across the cell membrane and gain access to the mitochondrial matrix. For the IC50 measurements, the inventors used a cell based assay and hence, it cannot be assessed whether some of the compounds make it into the mitochondria to interact with complex II. The best comparison would be made by comparing the Autodock results with an enzyme assay using purified complex II kits commercially available (MS201 COMPLEX II IMMUNO-CAPTURE KIT MitoScience LLC, 1850 Millrace Drive, Suite 3A, Eugene, Oreg. 97403, USA, http://www.mitosciences.com).

This kit can be used to isolate purified complex II from human, mouse, rat and bovine tissues and cell lines which can then be screened for activity and inhibition by the analogues using the DCPIP and PMS assay reaction outlined (King T E, 1967) or using competitive radioactive ubiquinone binding assays.

Example 9

Molecular Modeling Reveals Chemical Entities Capable of Binding to the Complex II Qp Site In this example computer modeling studies were used to identify chemical entities potentially capable of binding with great affinity to a ubiquinone $Q_p$ binding site and disrupting electron transfer. Such an entity would potentially be capable of killing a cancerous cell.

A virtual library of 65,000 commercially available compounds was downloaded from the ZINC Database project and a subset having desirable properties was docked against the crystal structure of porcine complex II (IZOY). The top 1000 compounds based on interaction energy were subjected to a more rigorous docking experiment and a final 10 compounds were identified as being the most likely compounds to interact with porcine complex II. Those compounds are shown in FIG. 10.

Based on the list of compounds and binding data from molecular modeling and biological assay, the desired/advantageous chemical entities for best binding into the Q sites of complex II include hydrophobic compounds with oxygen containing side groups where the oxygen may or may not be capable of becoming ionized. The core hydrophobic groups include tocopherols and its homologues, pyridoxal derivatives, ubiquinone derivatives, quininoline derivatives, benzyl groups including benzosulfonamides, pyridyl/pyridines, purines and pyrimidines, parthenolides, retinamides, sesquiterpene lactones. Substituted modifications to the side groups of the hydrophobic core compounds include sulphates, phosphates, phosphinic acids, sulfonamides, sulfonyl groups, propanoic acids, carboxylate and, methoxy, dioxy or propoxy substitutions.

Example 10

Peptide Conjugate LTVSPWY-α-TOS Suppresses Breast Carcinomas

This example describes the targeting of an α-TOS pro-drug to cancer cells over-expressing the receptor tyrosine kinase erbB2. An adduct of α-TOS was linked to the heptapeptide LTVSPWY (SEQ ID NO 1), which peptide is known for targeting cancer cells over-expressing erbB2. It was found that following binding to the receptor, the pro-drug was endocytosed and hydrolyzed by acidic peptidases to yield the apoptogenic α-TOS. As seen in FIG. 11, the adduct efficiently suppressed breast carcinomas in FVB/N MMTV rat c-neu transgenic mice featuring spontaneous breast tumors as a result of high erbB2 expression. In fact, there was an unexpected 90% relative reduction in size of treated tumors compared to the untreated control. Hence, this pro-drug/adduct may be particularly useful in treating cancer.

Example 11

α-TOS Inhibits Tumor Growth Irrespective of ErbB2 Status

For in vivo studies, the present inventors first determined whether α-TOS could suppress tumor growth in an animal model of breast cancer with low erbB2 expression, given that up to a third of human breast cancers express high levels of this receptor tyrosine kinase (Slamon et al, 1989). For this study, nude mice were xenotransplanted with the erbB2 low-expressing MCF-7 cells, which were then allowed to become established as tumors of about 5 mm in diameter before treatment with α-TOS (FIG. 12A). The results revealed that whereas tumors in the control mice progressed to grow up to 5-times their initial size to the point that euthanasia became necessary, α-TOS repressed the growth of tumors in the treated group of mice with an overall reduction in tumor size.

Next, the present inventors were interested in the response to treatment of erbB2 highly positive breast carcinomas using the spontaneously developing transgenic mouse model, FVB/N MMTV-rat c-neu, displaying clearly discernible breast cancers of ~10 mm in diameter at greater than 7 months of age (Guy et al, 1992). The two drugs, 3-BP and α-TOS, were compared for their relative efficacy as repressors of tumor growth. The results (FIG. 12B) revealed that compared to the control animals, the tumors in the treated mice showed either growth arrest or partial regression. α-TOS was found to be statistically more effective ($p<0.05$ by analysis of covariance) than 3-BP at inducing regression of the growth of breast tumors in these animals, resulting in a reduction in the average size of tumors by about 30-40% over the 2 weeks of treatment.

The effects of α-TOS and 3-BP on the growth of breast tumors in the xenotransplant and transgenic mice (cf FIG. 12) support their proposed application in clinical trials in human patients. However, the instant studies revealed resistance of erbB2 high-expressing cells to 3-BP. Since this receptor is commonly expressed at elevated levels in human breast cancer (Slamon et al, 1989), this presents a problem for the treatment of erbB2 highly positive patients. It is proposed that this problem may be overcome by simultaneously administering Akt siRNA or, alternatively, by combining 3-BP with α-TOS.

The benefit of using α-TOS and similar agents for treating breast cancer is as follows: α-TOS is efficient against both HER2-low (70% of breast cancer patients) and HER2-high breast tumors (30% breast cancer patients) i.e. irrespective of HER-2 expression. At this stage, the current approaches to treating HER2-low breast cancer patients are not very effective and α-TOS, as indicated above and throughout this specification, is selective and very efficient in pre-clinical models of cancer. With regard to HER2-high cancer patients, only the one treatment exists that complements current chemotherapeutic regimens and this is application of the humanized antibody against HER2, Herceptin. Again, α-TOS holds great promise over Herceptin for several reasons: Herceptin only is efficient against breast cancers with very high level of HER2 expression (3+ by fluorescent in situ hybridization), while α-TOS kills breast tumor cells and causes significant reduction of experimental breast carcinomas whether exhibiting high or low levels of HER2 expression; Herceptin is cardiotoxic, while α-TOS is not, since cardiac myocytes (heart muscle cells) have the propensity of hydrolyzing α-TOS into the apoptosis-silent vitamin E; Herceptin is forbiddingly expensive: treatment of one patient per year costs AUS50,000, while α-TOS is relatively inexpensive; finally, Herceptin does not cause extensive apoptosis of breast cancer cells and, rather, only halts tumor cell growth so that after cessation of treatment with Herceptin, the tumors can reoccur. By contrast, experiments with α-TOS using pre-clinical models of breast cancer revealed significant shrinkage of the tumors and consequently it can be anticipated that, upon prolonged treatments and using optimized dosing regimens with the appropriate formulation of TOS analogue, complete therapy of breast carcinoma may possibly be achieved.

Example 12

Use of α-TOS in Treating Mesothelioma

α-TOS was used to treat mesothelioma in a human cancer patient. Despite previous failed attempts with a range of different chemotherapies and other drugs, α-TOS worked very effectively and this patient has now regained their quality of life. The blood plasma levels were monitored and levels of α-TOS in the plasma attained 50 μM over prolonged periods during continual application. This is more than sufficient to kill the cancer cells based on in vitro analysis.

Summary of Clinical Study:

A 60 year old female patient with "terminal" mesothelioma that had previously received and failed to show improvement using 5 different cytotoxic agents. The patient was originally receiving high dose opiate medications, neuropathic pain medications, home oxygen, and was predicted to have a life expectancy of 6-8 weeks. After treatment with α-TOS, the patient no longer required analgesia or oxygen. The patient before starting α-TOS had a palpable anterior chest wall mass that on therapy with α-TOS shrunk dramatically. α-TOS therapy was non-toxic with no observable side-effects and was well tolerated.

Medical History:

The patient initially developed chest pains in July 2001 and was diagnosed with mesothelioma by biopsy in early May 2002. The patient was referred to palliative care for severe pain management and received deep X-ray radiotherapy (DXRT) to a right paraspinal mass in June 2002. In July 2002, started chemotherapy with concurrent Cisplatin, Gemcitabine and Thalidomide.

Treatment ceased in February 2003 due to toxicity problems with severe peripheral neuropathy, and ongoing nausea. In February 2003, treatment with Alimta and Carboplatin was started. Treatment was ceased in September 2003 due to severe toxicity with bone marrow suppression, and nausea and vomiting. In September 2003, treatment was started with phenoxodiol oral low dose (Novogen SAS drug) and remained stable until March 2005. However, treatment was again ceased due to ongoing severe neuropathy associated with phenoxodiol.

The mesothelioma advanced again as it showed further progression in March 2005. The patient started therapy with 2 doses of Gemcitabine, but again producing unacceptable levels of toxicity. In August 2005, the patient started therapy with 2 doses of Vinorelbine, which showed severe exacerbation of peripheral neuropathy.

In December 2005, the patient started receiving transdermal delivery of α-TOS, prepared in a base cream and solubilised with dimethyl sulfoxide (DMSO). The patient kept applying the formulation for about 8 weeks of treatment but developed major skin reaction problems secondary to DMSO (burns which took 4 weeks to heal). The mesothelioma showed clinical response but treatment had to cease because of the skin reaction.

In March 2006, the cancer showed rapid progression with a paraspinal mass causing nerve root compression. The patient underwent further DXRT, before further treatment with Coramsine (SAS drug Soblec WA). The cancer showed a stable response for 6 months, but then progressed again.

In November 2006, the patient was recommenced on Alimta-Avastin combination therapy, but after 4 months of therapy there were complications with severe side effects including nausea, uncontrolled diarrhoea and increased neuropathy, and treatment was ceased.

In April 2007, therapy with α-TOS was commenced using a modified formulation mixed in a lipodermal cream (see below). At this time, the mesothelioma showed spread of disease to be encasing the right lung and multiple metastases were visible by CT scan throughout both lungs. In addition, a palpable lesion was visible growing out between the ribs and the right anterior chest wall. The patient was in very poor condition with a low ECOG- no CT scan could be performed at the time of commencing the α-TOS treatment because the patient was too moribund.

After 4 weeks of applying the lipodermal preparation, the patient showed recovery with much improved anterior chest wall mass by CT scan with a decrease clinically by 50% and with ongoing α-TOS therapy, the patient continued to improve clinically.

α-TOS formulation: 500 gms of Lipoderm cream plus 60 gms α-TOS compounded by the hospital pharmacy. About 30 gms of compounded mix was administered every few days, and the upper body was wrapped in plastic film ("saran wrap") to improve absorption.

Side effects: There were no obvious side-effects from the α-TOS therapy apart from a mild itch which improved with an anti-histamine. All laboratory tests for blood markers and other signs for neuropathology or other adverse reactions have remained normal.

The foregoing embodiments are illustrative only of the principles of the invention, and various modifications and changes will readily occur to those skilled in the art. The invention is capable of being practiced and carried out in various ways and in other embodiments. It is also to be understood that the terminology employed herein is for the purpose of description and should not be regarded as limiting.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

Any reference to publications cited in this specification is not an admission that the disclosures constitute common general knowledge in Australia or elsewhere.

LIST OF REFERENCES

Albayrak T, Scherhammer V, Schoenfeld N, Braziulis E, Mund T, Bauer M K, Scheffler I E, Grimm S. (2003) The tumor suppressor cybL, a component of the respiratory chain, mediates apoptosis induction. *Mol Biol Cell.* August; 14(8):3082-96.

Allen F H (2002) The Cambridge Structural Database: a quarter of a million crystal structures and rising. *Acta Cripstallogr B* 58(Pt 3 Pt I):380-388.

Allen R G, Balin A K (2003) Effects of oxygen on the antioxidant responses of normal and transformed cells. *Exp Cell Res* 289:307-316.

Alleva R, Tomasetti M, Andera L, Gellert N, Borghi B, Weber C, Murphy M P, Neuzil J (2003) Coenzyme Q blocks chemical but not receptor-mediated apoptosis by increasing mitochondrial antioxidant protection. *FEBS Lett* 503: 46-50.

Aratri E, Spycher S E, Breyer I and Azzi A (1999) Modulation of α-tropomyosin expression by α-tocopherol in rat vascular smooth muscle cells. *FEBS Lett* 447:91-94.

Armstrong J S (2006) Mitochondria: a target for cancer therapy. *Br J Pharmacol* 147:239-48.

Arya P, Alibhai N, Qin H, Burton G W, Batist G, You S X and Alaoui-Jamali M A (1998) Design and synthesis of analogues of vitamin E: antiproliferative activity against human breast adenocarcinoma cells. *Bioorg Med Chem Lett* 8:2433-2438.

Astuti D, Hart-Holden N, Latif F, Lalloo F, Black G C, Lim C, Moran A, Grossman A B, Hodgson S V, Freemont A. Ramsden R, Eng C, Evans D G, Maher E R. (2003) Genetic analysis of mitochondrial complex II subunits SDHD, SDHB and SDHC in paraganglioma and phaeochromocytoma susceptibility. *Clin Endocrinol* (Oxf). December; 59(6):728-33

Azzi A, Ricciarelli R and Zingg J M (2002) Non-antioxidant molecular functions of α-tocopherol (vitamin E). *FEBS Lett* 519:8-10.

Barnett K T, Fokum F D, Malafa M P (2002) Vitamin E succinate inhibits colon cancer liver metastases. *J Surg Res* 106:292-298.

Bayley J P, van Minderhout I, Weiss M M, Jansen J C, Oomen P H, Menko F H, Pasini B, Ferrando B, Wong N, Alpert L C, Williams R, Blair E, Devilee P, Taschner P E. (2006) Mutation analysis of SDHB and SDHC: novel germline mutations in sporadic head and neck paraganglioma and familial paragangliorna and/or pheochromocytoma. *BMC Med Genet.* January 11; 7:1

Berridge M V, Herst P M, Tan A S. (2005) Tetrazolium dyes as tools in cell biology: new insights into their cellular reduction. *Biotechnol Annu Rev.* 11:127-52

Berridge M V and Tan A S (1993) Characterization of the cellular reduction of 3-(4,5-dimethylthiazol-2-yl)-2,5-diphenyl tetrazolium bromide (MTT): subcellular localization, substrate dependence, and involvement of mitochondrial electron transport in MTT reduction. *Arch Biochem Biophys* 303:474-478.

Birringer M, Drogan D and Brigelius-Ftohe R (2001) Tocopherols are metabolized in HepG2 cells by side chain co-oxidation and consecutive β-oxidation. *Free Radic Biol Med* 31:226-232.

Birringer M, EyTina J H, Salvatore B A and Neuzil J (2003) Vitamin E analogues as inducers of apoptosis: Structure-function relationship. *Br J Cancer* 88:1948-1955.

Birringer M, Pfluger P, Kluth D, Landes N and Brigelius-Flohe R (2002) Identities and differences in the metabolism of tocotrienols and tocopherols in HepG2 cells. *J Nutr* 132:3113-3118.

Boersma A W, Nooter K, Oostrum R G., Stoter G (1996) Quantification of apoptotic cells with fluorescein isothiocyanate-labeled annexin V in Chinese hamster ovary cell cultures with cisplatin. *Cytometry* 24:123-130

Breen G A, Scheffler I E. (1979) Respiration-deficient Chinese hamster cell mutants: biochemical characterization. *Somatic Cell Genet.* July; 5(4):441-51.

Briere J J, Schlemmer D, Chretien D. Rustin P. (2004) Quinone analogues regulate mitochondrial substrate competitive oxidation. *Biochem Biophys Res Commun*. April 16; 316(4): 1138-42.

Burstein H J (2005) The distinctive nature of HER2-positive breast cancers. *N Engl J Med* 353:1652-1654.

Bumrnell J N, John P, Whatley F R (1975) The reversibility of active sulphate transport in membrane vesicles of *Paracoccus* denitrificans. *Biochem J*. 150: 527-536.

Cardone M H, Roy N, Stennicke H R, Salvesen G S, Franke T F, Stanbridge E, Frisch S, Reed J C (1998) Regulation of cell death protease caspase-9 by phosphorylation. *Science* 282:1318-1321.

Cheeseman K H, Holley A E, Kelly F J, Wasil M, Hughes L and Burton G (1995) Biokinetics in humans of RRR-α-tocopherol: the free phenol, acetate ester, and succinate ester forms of vitamin E. *Free Radic Biol Med* 19:591-598

Choudhry Z M, Gavrikova E V, Kotlyar A B, Tushurashvili P R and Vinogradov A D. (1985) Pyridoxal phosphate-induced dissociation of the succinate: ubiquinone reductase. *FEBS Lett*. March 11; 182(1):171-5.

Choudhry Z M, Kotlyar A B and Vinogradov A D. (1986) Studies on the succinate dehydrogenating system. Interaction of the mitochondrial succinate-ubiquinone reductase with pyridoxal phosphate. *Biochim Biophys Acta*. June 10; 850(1):131-8.

Christen S, Woodall A A, Shigenaga M K, Southwel-Keely P T, Duncan M W, Ames B N. (1997) gamma-tocopherol traps mutagenic electrophiles such as NO(X) and complements alpha-tocopherol: physiological implications. *Proc Natl Acad Sci USA*. April 1; 94(7):3217-22.

Church S L, Grant J W, Ridnour L A, Oberley L W, Swanson P E, Meltzer P S, Trent J M (1993) Increased manganese superoxide dismutase expression suppresses the malignant phenotype of human melanoma cells. *Proc Natl Acad Sci USA* 90:3113-3117.

DeFrancesco L, Scheffler I E, Bissell M J. (1976) A respiration-deficient Chinese hamster cell line with a defect in NADH-coenzyme Q reductase. *J Biol. Chem*. August 10; 251(15):4588-95.

Devaraj S, Hugou I and Jialal 1 (2001) α-Tocopherol decreases CD36 expression in human monocyte-derived macrophages. *J Lipid Res* 42:521-527.

Don A S, Hogg P J (2004) Mitochondria as cancer drug targets. *Trends Mol Med* 10:372-378.

Dong L F, Wang X F, Zhao Y, Tomasetti M, Wu K, Neuzil J (2006) Vitamin E analogues as anti-cancer agents: the role of modulation of apoptosis signaling pathways. *Cancer Therapy* 4:35-46.

Esposti M D, Ngo A, Ghelli A, Benelli B, Carelli V, McLennan H, Linnane A W (1996) The interaction of Q analogs, particularly hydroxydecyl benzoquinone (idebenone), with the respiratory complexes of heart mitochondria. *Arch Biochem Biophys*. June 15; 330(2):395-400.

Fariss M W, Nicholls-Grzemski F A, Tirmenstein M A, Zhang J G (2001) Enhanced antioxidant and cytoprotective abilities of vitamin E succinate is associated with a rapid uptake advantage in rat hepatocytes and mitochondria. *Free Radic Biol Med* 31:530-541.

Fresno Vara J A, Casado E, de Castro J, Cejas P, Belda-Iniesta C, Gonzalez-Baron M (2004) PI3K/Akt signaling pathway and cancer. *Cancer Treat Rev* 30:193-204.

Galli F, Stabile A M, Betti M, Conte C, Pistilli A, Rende M, Floridi A and Azzi A (2004) The effect of α- and γ-tocopherol and their carboxyethyl hydroxychroman metabolites on prostate cancer cell proliferation. *Arch Biochemn Biophys* 423:97-102.

Geschwind J F, Ko Y H, Torbenson M S, Magee C, Pedersen P L (2002) Novel therapy for liver cancer: direct intraarterial injection of a potent inhibitor of ATP production. *Cancer Res* 62:3909-3913.

Gottlieb E, Tomlinson I P. (2005) Mitochondrial tumor suppressors: a genetic and biochemical update. *Nat Rev Cancer*. November; 5(11):857-66

Grandage V L, Gale R E, Linch D C, Khwaja A (2005) PI3-kinase/Akt is constitutively active in primary acute myeloid leukemia cells and regulates survival and chemoresistance via NF-κB, MAP kinase and p53 pathways. *Leukemia* 19:586-594.

Gu L Q, Yu L, Yu C A. (1990) Effect of substituents of the benzoquinone ring on electron-transfer activities of ubiquinone derivatives. *Biochim Biophys Acta*. February 22; 1015(3):482-92.

Guthrie N, Gapor A, Chambers A F and Carroll K K (1997) Inhibition of proliferation of estrogen receptor-negative MDA-MB-435 and -positive MCF-7 human breast cancer cells by palm oil tocotrienols and tamoxifen, alone and in combination. *J Nutr* 127: 544S-548S.

Guy C T, Webster M A, Schalier M, Parsons T J, Cardiff R D, Muller W J (1992) Expression of the neu protooncogene in the mammary epithelium of transgenic mice induces metastatic disease. *Proc Natl Acad Sci USA* 89:10578-10582.

Hartshorn M J (2002) AstexViewer™: An aid for structure-based drug design. *J Computer Aided Mol Des* 16: 871-881.

He L, Mo H, Hadisusilo S, Qureshi A A and Elson C E (1997) Isoprenoids suppress the growth of murine B16 melanomas in vitro and in vivo. *J Nutr* 127:668-674.

He D Y, Yu L, Yu C A. (1994) Protein ubiquinone interaction. Synthesis and biological properties of 5-alkyl ubiquinone derivatives. *J Biol. Chem*. November 11; 269(45):27885-8.

Hosomi A, Arita M, Sato Y, Kiyose C, Ueda T, Igarashi O, Arai H and Inoue K (1997) Affinity for α-tocopherol transfer protein as a determinant of the biological activities of vitamin E analogs. *FEBS Lett* 409:105-108.

Huang L S, Sun G, Cobessi D, Wang A C, Shen J T, Tung E Y, Anderson V E, Berry E A (2006) 3-nitropropionic acid is a suicide inhibitor of mitochondrial respiration that, upon oxidation by complex II, forms a covalent adduct with a catalytic base arginine in the active site of the enzyme. *J Biol Chem* 281:5965-5972

James A M, Cocheme H M, Smith R A, Murphy M P (2005) Interactions of mitochondria-targeted and untargeted ubiquinones with the mitochondrial respiratory chain and reactive oxygen species. Implications for the use of exogenous ubiquinones as therapies and experimental tools. *J Biol Chem* 280:21295-212312.

Kelso G F, Porteous C M, Coulter C V, Hughes G, Porteous W K, Ledgerwood E C, Smith R A, Murphy M P (2001) Selective targeting of a redox-active ubiquinone to mitochondria within cells: antioxidant and antiapoptotic properties. *J Biol Chem* 276:4588-4596.

Kim R, Tanabe K, Emi M, Uchida Y, Toge T (2004) Potential roles of antisense therapy in the molecular targeting of genes involved in cancer. *Int Oncol* 24:5-17

King A, Selak M A, Gottlieb E. (2006) Succinate dehydrogenase and fumarate hydratase: linking mitochondrial dysfunction and cancer. *Oncogene*. August 7; 25(34):4675-82

King T E (1967). Preparation of succinate dehydrdogenase and reconstitution of succinate oxidase. *Methods Enzymol* 10: 322-331.

King, T. S. (1967) Preparations of succinate-cytochrome c reductase and the cytochrome b-$c_1$ particle, and reconstitution of succinate-cytochrome c reductase. *Methods in Enzymology*, 10, 216-225

Ko Y H, Smith B L, Wang Y, Pomper M G, Rini D A, Torbenson M S, Hullihen J, Pedersen P L (2004) Advanced cancers: eradication in all cases using 3-bromopyruvate therapy to deplete ATP. *Biochem Biophys Res Commun* 324:269-275.

Kogure K, Hama S, Kisaki M, Takemasa H, Tokumura A, Suzuki I and Fukuzawa K (2004) Structural characteristic of terminal dicarboxylic moiety required for apoptogenic activity of α-tocopheryl esters. *Biochim Biophys Acta* 1672: 93-99.

Kogure K, Manabe S, Suzuki I, Tokumura A and Fukuzawa K (2005) Cytotoxicity of α-tocopheryl succinate, malonate and oxalate in normal and cancer cells in vitro and their anti-cancer effects on mouse melanoma in vivo. *J Nutr Sci Vitaminol* 51:392-397.

Kunisaki M, Bursell S E, Clermont A C, Ishii H, Ballas L M, Jirousek MR Umeda F, Nawata H and King G L (1995) Vitamin E prevents diabetes-induced abnormal retinal blood flow via the diacylglycerol-protein kinase C pathway. *Am J Physiol* 269:E239-246.

Maehara Y, Kusumoto T, Kusumoto H, Anai H, Sugimachi K (1988) Sodium succinate enhances the colorimetric reaction of the in vitro chemosensitivity test: MTT assay. *Oncology* 5:434-436.

Makishima M, Umesono K, Shudo K, Naoe T, Kishi K and Honma Y (1998) Induction of differentiation in acute promyelocytic leukemia cells by 9-cis retinoic acid α-tocopherol ester (9-cis tretinoin tocoferil). *Blood* 91:4715-4726.

Malafa M P, Fokum F D, Mowlavi A, Abusief M, King M (2002) Vitamin E inhibits melanoma growth in mice. *Surgery* 131:85-91.

Malafa M P, Neitzel L T. Vitamin E succinate promotes breast cancer tumor dormancy. *J Surg Res* 93:163-170.

Martin-Nizard F, Boullier A, Fruchart J C and Duriez P (1998) α-Tocopherol but not 13-tocopherol inhibits thrombin-induced PKC activation and endothelin secretion in endothelial cells. *J Cardiovasc Risk* 5:339-345.

Morris G M, Goodsell D S, Halliday R S, Huey R, Hart W E, Belew R K, Olson A J (1998) Automated docking using a Lamarckian genetic algorithm and empirical binding free energy function. *J Comp Chem* 19: 1639-1662.

Morton L W, Ward N C, Croft K D, and Puddey I B. (2002) Evidence for the nitration of gamma-tocopherol in vivo: 5-nitro-gamma-tocopherol is elevated in the plasma of subjects with coronary heart disease. *Biochem J*. June 15; 364(Pt 3):625-8.

Munteanu A, Zingg J M, Ogru E, Libinaki R, Gianello R, West S, Negis Y and Azzi (2004) AModulation of cell proliferation and gene expression by α-tocopheryl phosphates: relevance to atherosclerosis and inflammation. *Biochem Biophys Res Conunun* 318:311-316.

Negis Y, Zingg J M, Ogru E, Gianello R, Libinaki R and Azzi A (2005) On the existence of cellular tocopheryl phosphate, its synthesis, degradation and cellular roles: a hypothesis. *IUBMB Life* 57:23-25.

Nesaretnam K, Stephen R, Dils R and Darbre P (1998) Tocotrienols inhibit the growth of human breast cancer cells irrespective of estrogen receptor status. *Lipids* 33:461-469.

Neuzil J, Dong L F, Ramanathapuram L, Hahn T, Chladova M, Wang X F, Zobalova R, Prochazka L, Gold M, Freeman R, Turanek J, Akporiaye E T, Dyason J C, Ralph S J. (2007) Vitamin E analogues as a novel group of mitocans: Anti-cancer agents that act by targeting mitochondria. *Mol Aspects Med*. February 23.

Neuzil J, Massa H (2005) Hepatic processing determines dual activity of vitamin E succinate. *Biochem Biophys Res Conmnun* 327:1024-1027.

Neuzil J, Tomasetti M, Mellick A S, Alleva R, Salvatore B A, Birringer M, Fariss M W (2004) Vitamin E analogues: A new class of inducers of apoptosis with selective anti-cancer effects. *Curr Cancer Drug Targets* 4:355-372.

Neuzil J, Tomasetti M, Zhao Y, Dong L F, Birringer M, Wang X F, Low P, Wu K, Salvatore B A, Ralph S J. (2007) Vitamin E analogs, a novel group of "mitocans," as anticancer agents: the importance of being redox-silent. *Mol. Pharmacol*. May; 71(5):1185-99.

Neuzil J, Weber T, Gellert N, Weber C (2001) Selective cancer cell killing by α-tocopheryl succinate. *Br J Cancer* 84:87-89.

Neuzil J, Weber T, Schroder A, Lu M, Ostermann G, Gellert N, Mayne G C, Olejnicka B, Negre-Salvayre A, Sticha M, Coffey R J, Weber C (2001) Induction of apoptosis in cancer cells by α-tocopheryl succinate: Molecular pathways and structural requirements. *FASEB J* 15:403-415.

Nishikawa K, Satoh H, Hirai A, Suzuki K, Asano R, Kumadaki I, Hagiwara K and Yano T (2003) α-Tocopheryloxybutyric acid enhances necrotic cell death in breast cancer cells treated with chemotherapy agent. *Cancer Lett* 201:51-56

Oostveen F G, Au H C, Meijer P J, Scheffler I E. (1995) A Chinese hamster mutant cell line with a defect in the integral membrane protein CII-3 of complex II of the mitochondrial electron transport chain. *J Biol. Chem*. November 3; 270(44):26104-8.

Osaki M, Oshimura M, Ito H (2004) PI3K-Akt pathway: its functions and alterations in human cancer. *Apoptosis* 9:667-676.

Pham D Q and Plakogiannis R (2005) Vitamin E supplementation in cardiovascular disease and cancer prevention: Part 1. *Ann Pharmacother* 39:1870-8

Pollard P J, Briere J J, Alam N A, Barwell J, Barclay E, Wortham N C, Hunt T, Mitchell M, Olpin S, Moat S J, Hargreaves I P, Heales S J, Chung Y L, Griffiths J R, Dalgleish A, McGrath J A, Gleeson M J, Hodgson S V, Poulsom R, Rustin P, Tomlinson I P. (2005) Accumulation of Krebs cycle intermediates and over-expression of HIF1alpha in tumors which result from germline FH and SDH mutations. *Hum Mol Genet*. August 1; 14(15):2231-9.

Quin J, Engle D, Litwiller A, Peralta E, Grasch A, Boley T, Hazelrigg S (2005) Vitamin E succinate decreases lung cancer tumor growth in mice. *J Surg Res* 127:139-143.

Qureshi A A, Mo H, Packer L and Peterson D M (2000) Isolation and identification of novel tocotrienols from rice bran with hypocholesterolemic, antioxidant, and antitumor properties. *J Agric Food Chem* 48:3130-3140.

Ralph S J, Dong L F, Low P, Lawen A, and Neuzil J (2006) Mitocans: mitochondria targeted anti-cancer drugs as improved therapies and related patents. *Recent Pat Anti-cancer Drug Discov* 1:305-326.

Ricciarelli R, Zingg J M and Azzi A (2000) Vitamin E reduces the uptake of oxidized LDL by inhibiting CD36 scavenger receptor expression in cultured aortic smooth muscle cells. *Circulation* 102:82-87.

Safford S E, Oberley T D, Urano M, St Clair D K (1994) Suppression of fibrosarcoma metastasis by elevated expression of manganese superoxide dismutase. *Cancer Res* 54:4261-4265.

Sanborn B M, Felberg N T, Hollocher T C (1971) The inactivation of succinate dehydrogenase by bromopyruvate. *Biochim Biophys Acta* 227:219-231.

Sanner M F (1999) Python: a programming language for software integration and development, *J Mol Graphic Mod* 17: 57-61.

Sanders G., et al (2001) Preparation of tocopherols, tocotrienols, other chromnan and side chain derivatives that induce cell apoptosis for therapeutic use as antiproliferative agents. 2001: PCT Int. Appl. WO 2001058889. p. 120.

Scallet A C, Haley R L, Scallet D M, Duhart H M, Binienda Z K (2003) 3-nitropropionic acid inhibition of succinate dehydrogenase (complex II) activity in cultured Chinese hamster ovary cells: antagonism by L-carnitine. *Ann NY Acad Sci* 993:305-312.

Scheffler I E, Yadava N, Potluri P. (2004) Molecular genetics of complex I-deficient Chinese hamster cell lines. *Biochim Biophys Acta*. December 6; 1659(2-3):160-71. Review.

Seo, B. B., Kitajima-Ihara, T., Chan, E. K., Scheffler, I.E., Matsuno-Yagi, A., and Yagi, T. (1998) *Proc. Natl. Acad. Sci. USA* 95, 9167-9171

Shah S J and Sylvester P W (2005) γ-Tocotrienol inhibits neoplastic mammary epithelial cell proliferation by decreasing Akt and nuclear factor κB activity. *Exp Biol Med* 230: 235-241.

Shiau C W, Huang J W, Wang D S, Weng J R, Yang C C, Lin C H, Li C, Chen C S (2006) alpha-Tocopheryl succinate induces apoptosis in prostate cancer cells in part through inhibition of Bcl-xL/Bcl-2 function. *J Biol Chem* 281: 11819-11825.

Shun M C, Yu W, Gapor A, Parsons R, Atkinson J, Sanders B G and Kline K (2004) Pro-apoptotic mechanisms of action of a novel vitamin E analog (α-TEA) and a naturally occurring form of vitamin E (δ-tocotrienol) in MDA-MB-435 human breast cancer cells. *Nutr Cancer* 48:95-105.

Slamon D J, Godolphin W, Jones L A, Holt J A, Wong S G, Keith D E, Levin W J, Stuart S G, Udove J, Ullrich A, et al (1989) Studies of the HER-2/neu proto-oncogene in human breast and ovarian cancer. *Science* 244:707-712.

Stapelberg M, Gellert N, Swettenham E, Tomasetti M, Witting P K, Procopio A, Neuzil J (2005) α-Tocopheryl succinate inhibits malignant mesothelioma by disruption of the FGF autocrine signaling loop: Mechanism and the role of oxidative stress. *J Biol Chem* 280:25369-25376.

Sugawara M, Huang W, Fei Y-J, Leibach F H, Ganaphthy V and Ganaphthy M E (2000) Transport of valgancyclovir, a gancyclovir prodrug, via peptide transporters PEPT1 and PEPT2. *J Pharm Sci* 89:781-789.

Sun F, Huo X, Zhai Y, Wang A, Xu J, Su D, Bartlam M, Rao Z. Crystal structure of mitochondrial respiratory membrane protein complex II. *Cell* 121:1043-1057.

Swettenham E, Witting P K, Salvatore B A, Neuzil J (2005) α-Tocopheryl succinate selectively induces apoptosis in neuroblastoma cells: Potential therapy of malignancies of the nervous system?*J Neurochem* 94:1448-1456.

Takeuchi H, Kim J, Fujimoto A, Umetani N, Mori T, Bilchik A, Turner R, Tran A, Kuo C, Hoon D S (2005) X-Linked inhibitor of apoptosis protein expression level in colorectal cancer is regulated by hepatocyte growth factor/C-met pathway via Akt signaling. *Clin Cancer Res* 11:7621-7628.

Tan A K, Ramsay R R, Singer T P, Miyoshi H. (1993) Comparison of the structures of the quinone-binding sites in beef heart mitochondria. *J Biol. Chem*. September 15; 268 (26):19328-33.

Tasinato A, Boscoboinik D, Bartoli G M, Maroni P and Azzi A (1995) d-α-Tocopherol inhibition of vascular smooth muscle cell proliferation occurs at physiological concentrations, correlates with protein kinase C inhibition, and is independent of its antioxidant properties. *Proc Natl Acad Sci USA* 92:12190-12194.

Teague, S. J.; Davis, A. M.; Leeson, P. D.; Oprea, T. (1999) The Design of Leadlike Combinatorial Libraries. *Angew Chem Int Ed Engl*, 38, 3743-3748

Tomasetti M, Gellert N, Procopio A, Neuzil J (2004) A vitamin E analogue suppresses malignant mesothelioma in a pre-clinical model: A prototype of a future drug against a fatal neoplastic disease?*Int J Cancer* 109:641-642.

Tomic-Vatic A, EyTina J H, Chapmann J M, Mahdavian E, Neuzil J and Salvatore B A (2005) Vitamin E amides, a new class of vitamin E analogues with enhanced pro-apoptotic activity. *Int J Cancer* 117:118-193.

van Nederveen F H, Korpershoek E, Lenders J W, de Krijger R R, Dinjens W N. (2007) Somatic SDHB mutation in an extraadrenal pheoclromocytoma. *N Engl J Med*. July 19; 357(3):306-8.

Vraka P S, Drouza C, Rikkou M P, Odysseos A D and Keramidas A D (2006) Synthesis and study of the cancer cell growth inhibitory properties of α-, γ-tocopheryl and γ-tocotrienyl 2-phenylselenyl succinates. Bioorg Med Chem 14: 2684-2696.

Wallace, A. C., Laskowski, R. A. and Thornton, J. M. (1995). LIGPLOT: a program to generate schematic diagrams of protein-ligand interactions. Protein Eng 8, 127-134.

Wang X F, Dong L F, Zhao Y, Tomasetti M, Wu K, Neuzil J (2006) Vitamin E analogues as anti-cancer agents: Lessons from studies with α-tocopheryl succinate. *Mol Nutr Food Res* 50:675-685.

Wang X F, Witting P K, Salvatore B A, Neuzil J (2005) α-Tocopheryl succinate induces apoptosis in HER2/erbB2-overexpressing breast cancer cells by signalling via the mitochondrial pathway. *Biochemn Biophvs Res Conmmun* 326:282-289.

Weber T, Dalen H, Andera L, Negre-Salvayre A, Auge N, Sticha M, Lloret A, Terman A, Witting P K, Higuchi M, Plasilova M, Zivny J, Gellert N, Weber C, Neuzil J (2003) Mitochondria play a central role in apoptosis induced by α-tocopheryl succinate, an agent with anticancer activity. Comparison with receptor-mediated pro-apoptotic signaling. *Biochemistry* 42:4277-4291.

Weber T, Lu M, Andera L, Lahm H, Gellert N, Fariss M W, Korinek V, Sattler W, Ucker D S, Terman A, Schroder A, Erl W. Brunk U T, Coffey R J, Weber C, Neuzil J (2002) Vitamin E succinate is a potent novel anti-neoplastic agent with high tumor selectivity and cooperativity with tumor necrosis factor-related apoptosis-inducing ligand (TRAIL, Apo2L) in vivo. *Clin Cancer Res* 8:863-869.

West K A, Castillo S S, Dennis P A (2002) Activation of the PI3K/Akt pathway and chemotherapeutic resistance. *Drug Resist Updat* 5:234-248.

Wu Y, Zu K, Ni J, Yeh S, Kasi D, James N S, Chemler S and Ip C (2004) Cellular and molecular effects of α-tocopheryloxybutyrate: lessons for the design of vitamin E analog for cancer prevention. *Anticancer Res* 24:3795-3802.

Xu R H, Pelicano H, Zhou Y, Carew J S, Feng L, Bhalla K N, Keating M J, and Huang P (2005) Inhibition of glycolysis in cancer cells: a novel strategy to overcome drug resistance associated with mitochondrial respiratory defect and hypoxia. *Cancer Res* 65:613-621.

Yabunaka H, Kenmochi A, Nakatogawa Y, Sakamoto K, Miyoshi H. (2002) Hybrid ubiquinone: novel inhibitor of mitochondrial complex I. *Biochim Biophys Acta*. December 2; 1556(2-3):106-12.

Yamauchi J, Iwamoto T, Kida S, Masushige S, Yamada K and Esashi T (2001) Tocopherol-associated protein is a ligand-dependent transcriptional activator. *Biochem Biophys Res Comnun* 285:295-299.

Yang F, Yu L, He D Y, Yu C A. (1991) Protein-ubiquinone interaction in bovine heart mitochondrial succinate-cytochrome c reductase. Synthesis and biological properties of fluorine substituted ubiquinone derivatives. *J Biol Chew*. November 5; 266(31):20863-9.

Yankovskaya V, Sablin S O, Ramsay R R, Singer T P, Ackrell B A, Cecchini G, Miyoshi H. (1996) Inhibitor probes of the quinone binding sites of mammalian complex II and *Escherichia coli* fiumarate reductase. *J Biol Chem*. August 30; 271(35):21020-4.

Yano Y, Satoh H, Fukumoto K, Kumadaki I, Ichikawa T, Yamada K, Hagiwara K and Yano T (2005) Induction of cytotoxicity in human lung adenocarcinoma cells by 6-O-carboxy-propyl-α-tocotrienol, a redox-silent derivative of α-tocotrienol. *Int J Cancer* 115:839-846.

Yoeli-Lerner M, Yiu G K, Rabinovitz I, Erhardt P, Jauliac S, Toker A (2005) Akt blocks breast cancer cell motility and invasion through the transcription factor NFAT. *Mol Cell* 20:539-550.

Youk H J, Lee E, Choi M K, Lee Y J, Chung J H, Kim S H, Lee C H and Lim S J (2005) Enhanced anticancer efficacy of α-tocopheryl succinate by conjugation with polyethylene glycol. *J Control Release* 107:43-52.

Zhang J G, Nicholls-Grzemski F A, Tirmenstein M A, Fariss M W (2001a) Vitamin E succinate protects hepatocytes against the toxic effect of reactive oxygen species generated at mitochondrial complexes I and III by alkylating agents. *Chem Biol Interact* 138:267-284.

Zhang J G, Tirmenstein M A, Nicholls-Grzemski F A, Fariss M W (2001b) Mitochondrial electron transport inhibitors cause lipid peroxidation-dependent and -independent cell death: protective role of antioxidants. *Arch Biochem Biophys* 393:87-96.

Zhao S, Konopleva M, Cabreira-Hansen M, Xie Z, Hu W, Milella M, Estrov Z, Mills G B, Andreeff M (2004) Inhibition of phosphatidylinositol 3-kinase dephosphorylates BAD and promotes apoptosis in myeloid leukemias. *Leukemia* 18:267-27.

---

The invention claimed is:

1. A method of testing whether a subject having cancer is likely to respond to therapy comprising the administration of a pro-oxidant compound, said method comprising the steps of: (i) introducing the pro-oxidant compound into mitochondria of a cancerous cell sourced from said subject; (ii) assaying for the binding of the pro-oxidant compound to a ubiquinone-binding site of complex II of the mitochondria, wherein said assay of step (ii) is selected from the group consisting of assaying for actual binding of the pro-oxidant compound with the ubiquinone-binding site of complex II, or assaying for an effect caused by the binding of the pro-oxidant compound with the ubiquinone-binding site of complex II wherein said effect is not death of the cancerous cell; and (iii) assaying for death of the cancerous cell, wherein the binding of the pro-oxidant compound and the death of the cancerous cell by the pro-oxidant compound indicates that the subject is likely to respond to the therapy.

2. The method of claim 1, wherein said pro-oxidant compound is a pro-oxidant vitamin E analogue.

3. The method of claim 2, wherein said pro-oxidant vitamin E analogue is a-TOS.

* * * * *